(12) United States Patent
Carusillo et al.

(10) Patent No.: US 11,896,239 B2
(45) Date of Patent: Feb. 13, 2024

(54) SURGICAL HANDPIECE SYSTEM FOR DEPTH MEASUREMENT AND RELATED ACCESSORIES

(71) Applicant: Stryker Corporation, Kalamazoo, MI (US)

(72) Inventors: Steven J. Carusillo, Kalamazoo, MI (US); Trevor Jonathan Lambert, Portage, MI (US); Joseph O. Marietta, Kalamazoo, MI (US); Stephen Frederick Peters, Hickory Corners, MI (US)

(73) Assignee: Stryker Corporation, Kalamazoo, MI (US)

( * ) Notice: Subject to any disclaimer, the term of this patent is extended or adjusted under 35 U.S.C. 154(b) by 108 days.

(21) Appl. No.: 17/576,248

(22) Filed: Jan. 14, 2022

(65) Prior Publication Data
US 2022/0211391 A1  Jul. 7, 2022

Related U.S. Application Data

(63) Continuation of application No. 16/639,690, filed as application No. PCT/IB2018/056251 on Aug. 17, (Continued)

(51) Int. Cl.
*A61B 17/16* (2006.01)
*A61B 17/14* (2006.01)

(52) U.S. Cl.
CPC ........ *A61B 17/1615* (2013.01); *A61B 17/162* (2013.01); *A61B 17/1622* (2013.01);
(Continued)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 2,763,935 A  9/1956 Whaley et al.
3,837,661 A  9/1974 Phillippi
(Continued)

FOREIGN PATENT DOCUMENTS

AU  2015312037 A1  3/2017
AU  2014346458 B2  11/2018
(Continued)

OTHER PUBLICATIONS

English language abstract for CN 106163427 A extracted from espacenet.com database on Nov. 16, 2022, 2 pages.
(Continued)

*Primary Examiner* — Eric S Gibson
(74) *Attorney, Agent, or Firm* — Howard & Howard Attorneys PLLC

(57) ABSTRACT

A surgical handpiece system for performing measurement functions and surgical operations. The system includes a handpiece assembly. The handpiece has a handpiece housing and a drive cannula rotatably coupled to the handpiece housing. The drive cannula extends along an axis and is configured to receive torque from a motor. A surgical attachment module has an attachment housing removably coupleable to the handpiece housing. The surgical attachment module has a drive shaft rotatably coupled to the surgical attachment housing and configured to receive torque from the drive cannula to operate an end effector. A measurement module has a measurement housing removably coupleable to the handpiece housing. The measurement module is configured to perform measurement functions associated with operation of the handpiece assembly.

20 Claims, 68 Drawing Sheets

Related U.S. Application Data 2018, now Pat. No. 11,317,927, which is a continuation-in-part of application No. 15/887,507, filed on Feb. 2, 2018, now Pat. No. 10,159,495.

(60) Provisional application No. 62/618,134, filed on Jan. 17, 2018, provisional application No. 62/548,357, filed on Aug. 21, 2017, provisional application No. 62/546,760, filed on Aug. 17, 2017.

(52) U.S. Cl.
CPC ........ *A61B 17/1637* (2013.01); *A61B 17/142* (2016.11); *A61B 17/1624* (2013.01); *A61B 17/1626* (2013.01)

(58) Field of Classification Search
CPC ............ A61B 17/1622; A61B 17/1624; A61B 17/1626; A61B 17/1628
See application file for complete search history.

(56) References Cited

U.S. PATENT DOCUMENTS

| | | | |
|---|---|---|---|
| 3,897,166 | A | 7/1975 | Adams |
| 4,310,269 | A | 1/1982 | Neu et al. |
| 4,359,906 | A | 11/1982 | Cordey |
| 4,688,970 | A | 8/1987 | Eckman |
| 4,705,038 | A | 11/1987 | Sjostrom et al. |
| 4,752,161 | A | 6/1988 | Hill |
| 4,820,962 | A | 4/1989 | Millauer |
| 5,071,293 | A | 12/1991 | Wells |
| 5,200,747 | A | 4/1993 | Betz et al. |
| 5,257,531 | A | 11/1993 | Motosugi et al. |
| 5,269,794 | A | 12/1993 | Rexroth |
| RE34,556 | E | 3/1994 | Sjostrom et al. |
| 5,499,984 | A | 3/1996 | Steiner et al. |
| 5,667,509 | A | 9/1997 | Westin |
| 5,785,522 | A | 7/1998 | Bergstrom et al. |
| 5,838,222 | A | 11/1998 | Al-Rawi |
| 5,895,389 | A | 4/1999 | Schenk et al. |
| 6,033,409 | A * | 3/2000 | Allotta .................... B25F 5/003 606/80 |
| 6,096,042 | A * | 8/2000 | Herbert .............. A61B 17/8891 606/80 |
| 6,223,137 | B1 | 4/2001 | McCay et al. |
| 6,336,931 | B1 | 1/2002 | Hsu et al. |
| 6,382,977 | B1 | 5/2002 | Kumar |
| 6,391,005 | B1 | 5/2002 | Lum et al. |
| 6,394,806 | B1 | 5/2002 | Kumar |
| 6,514,258 | B1 | 2/2003 | Brown et al. |
| 6,562,055 | B2 | 5/2003 | Walen |
| 6,565,293 | B2 | 5/2003 | Desmoulins |
| 6,591,698 | B1 | 7/2003 | Carlsson et al. |
| 6,620,101 | B2 | 9/2003 | Azzam et al. |
| 6,665,948 | B1 * | 12/2003 | Kozin .................... A61B 90/06 175/45 |
| 6,719,962 | B2 | 4/2004 | Day et al. |
| 6,748,273 | B1 | 6/2004 | Obel et al. |
| 6,783,533 | B2 | 8/2004 | Green et al. |
| 6,786,683 | B2 | 9/2004 | Schaer et al. |
| 6,863,136 | B2 | 3/2005 | Bar-Cohen et al. |
| 7,060,071 | B2 | 6/2006 | Steiger |
| 7,141,074 | B2 | 11/2006 | Fanger et al. |
| 7,163,542 | B2 | 1/2007 | Ryan |
| 7,188,431 | B2 | 3/2007 | Herrmann et al. |
| 7,258,546 | B2 | 8/2007 | Beier et al. |
| 7,431,682 | B2 | 10/2008 | Zeiler et al. |
| 7,482,819 | B2 | 1/2009 | Wuersch |
| 7,517,351 | B2 | 4/2009 | Culp et al. |
| 7,580,743 | B2 | 8/2009 | Bourlion et al. |
| 7,681,659 | B2 * | 3/2010 | Zhang .................... B25B 21/00 173/4 |
| 7,740,425 | B2 | 6/2010 | Zeiler et al. |
| 7,748,273 | B2 | 7/2010 | Halevy-Politch et al. |
| 7,771,143 | B2 | 8/2010 | Bharadwaj et al. |
| 7,848,799 | B2 | 12/2010 | Herndon |
| 8,092,457 | B2 | 1/2012 | Oettinger et al. |
| 8,241,229 | B2 | 8/2012 | Herndon |
| 8,249,696 | B2 | 8/2012 | Fisher et al. |
| 8,402,829 | B2 | 3/2013 | Halevy-Politch et al. |
| 8,419,746 | B2 | 4/2013 | Bourlion et al. |
| 8,460,297 | B2 | 6/2013 | Watlington et al. |
| 8,463,421 | B2 | 6/2013 | Brett et al. |
| 8,480,682 | B2 | 7/2013 | Howlett et al. |
| 8,486,119 | B2 | 7/2013 | Bourlion |
| 8,511,945 | B2 * | 8/2013 | Apkarian ................ B23B 49/00 408/112 |
| 8,535,342 | B2 | 9/2013 | Malackowski et al. |
| 8,603,148 | B2 | 12/2013 | Raven, III et al. |
| 8,641,674 | B2 | 2/2014 | Bobroff et al. |
| 8,821,493 | B2 | 9/2014 | Anderson |
| 8,876,444 | B1 | 11/2014 | Chanturidze |
| 8,894,654 | B2 * | 11/2014 | Anderson ............... B23B 49/02 173/176 |
| D719,594 | S | 12/2014 | Leugers |
| 8,936,468 | B2 | 1/2015 | Ranck et al. |
| D722,627 | S | 2/2015 | Leugers |
| 8,970,207 | B2 | 3/2015 | Baumgartner |
| 8,974,227 | B2 | 3/2015 | Magnusson et al. |
| D727,985 | S | 4/2015 | Leugers |
| 9,033,707 | B2 | 5/2015 | Dricot |
| D732,364 | S | 6/2015 | Rinaldis et al. |
| 9,204,885 | B2 * | 12/2015 | McGinley ............ A61B 17/162 |
| 9,256,988 | B2 | 2/2016 | Wenger et al. |
| 9,289,219 | B2 | 3/2016 | Kumar |
| 9,326,832 | B2 | 5/2016 | Zuker et al. |
| 9,345,487 | B2 | 5/2016 | Herndon et al. |
| D759,244 | S | 6/2016 | Leugers |
| D759,245 | S | 6/2016 | Leugers |
| 9,358,016 | B2 * | 6/2016 | McGinley ............ A61B 17/162 |
| 9,370,372 | B2 | 6/2016 | McGinley et al. |
| 9,468,445 | B2 | 10/2016 | McGinley et al. |
| 9,492,181 | B2 * | 11/2016 | McGinley ............ A61B 17/162 |
| 9,526,511 | B2 | 12/2016 | Anderson |
| 9,554,807 | B2 | 1/2017 | McGinley et al. |
| 9,566,121 | B2 | 2/2017 | Staunton et al. |
| 9,649,141 | B2 | 5/2017 | Raven, III et al. |
| 9,826,984 | B2 * | 11/2017 | McGinley ............ A61B 17/142 |
| 9,877,734 | B2 * | 1/2018 | Anderson ............ B23B 45/008 |
| 9,914,192 | B2 | 3/2018 | Rola et al. |
| 10,149,686 | B2 * | 12/2018 | Anderson ............... A61B 17/17 |
| 10,159,495 | B1 | 12/2018 | Lambert |
| 10,278,712 | B2 | 5/2019 | Edwards et al. |
| 10,321,920 | B2 * | 6/2019 | McGinley .......... A61B 17/1633 |
| 10,398,453 | B2 * | 9/2019 | McGinley ............... A61B 90/30 |
| 10,661,428 | B2 | 5/2020 | Baskar et al. |
| 10,736,643 | B2 * | 8/2020 | Anderson .......... A61B 17/1624 |
| 10,736,644 | B2 * | 8/2020 | Windolf ............. A61B 17/1626 |
| 10,925,619 | B2 * | 2/2021 | Anderson .......... A61B 17/1628 |
| 11,058,436 | B2 * | 7/2021 | McGinley ............ A61B 17/142 |
| 11,317,927 | B2 * | 5/2022 | Carusillo ............ A61B 17/162 |
| 2003/0199856 | A1 | 10/2003 | Hill et al. |
| 2004/0059317 | A1 | 3/2004 | Hermann |
| 2004/0215395 | A1 * | 10/2004 | Strasser ................ B23B 49/006 702/9 |
| 2005/0116673 | A1 * | 6/2005 | Carl .................... A61B 17/1626 318/432 |
| 2005/0131415 | A1 * | 6/2005 | Hearn .................. B25B 23/147 606/80 |
| 2005/0131416 | A1 | 6/2005 | Jansen et al. |
| 2005/0171553 | A1 | 8/2005 | Schwarz et al. |
| 2006/0241628 | A1 * | 10/2006 | Parak .................. A61B 17/1626 606/80 |
| 2007/0206996 | A1 | 9/2007 | Bharadwaj et al. |
| 2009/0221922 | A1 | 9/2009 | Lec et al. |
| 2009/0245956 | A1 * | 10/2009 | Apkarian ................ B23B 49/00 408/11 |
| 2009/0297284 | A1 * | 12/2009 | Brown ............... G05B 19/4163 700/170 |
| 2009/0326537 | A1 * | 12/2009 | Anderson ................ A61B 17/17 606/80 |
| 2010/0034605 | A1 | 2/2010 | Huckins et al. |

(56) References Cited

U.S. PATENT DOCUMENTS

| | | |
|---|---|---|
| 2010/0063524 A1 | 3/2010 | McCombs |
| 2010/0167233 A1 | 7/2010 | Dricot |
| 2011/0020084 A1 | 1/2011 | Brett et al. |
| 2011/0089248 A1 | 4/2011 | Deng et al. |
| 2011/0230886 A1 | 9/2011 | Gustilo et al. |
| 2011/0245833 A1* | 10/2011 | Anderson ............... B23B 49/02 606/80 |
| 2012/0123417 A1 | 5/2012 | Smith |
| 2012/0283706 A1 | 11/2012 | Blust |
| 2012/0310247 A1 | 12/2012 | Hsieh |
| 2012/0316591 A1 | 12/2012 | Thorne et al. |
| 2013/0138106 A1 | 5/2013 | Kumar |
| 2013/0307529 A1 | 11/2013 | Baumgartner |
| 2013/0338669 A1 | 12/2013 | Brianza et al. |
| 2014/0018810 A1 | 1/2014 | Knape et al. |
| 2014/0046332 A1 | 2/2014 | Premanathan et al. |
| 2014/0114316 A1 | 4/2014 | Xu et al. |
| 2014/0148808 A1 | 5/2014 | Inkpen et al. |
| 2014/0222003 A1 | 8/2014 | Herndon et al. |
| 2014/0275955 A1 | 9/2014 | Crawford et al. |
| 2014/0324050 A1 | 10/2014 | Masson |
| 2014/0371751 A1 | 12/2014 | Thomas |
| 2014/0371752 A1 | 12/2014 | Anderson |
| 2015/0066030 A1 | 3/2015 | McGinley et al. |
| 2015/0066035 A1 | 3/2015 | McGinley et al. |
| 2015/0066036 A1 | 3/2015 | McGinley et al. |
| 2015/0066037 A1 | 3/2015 | McGinley et al. |
| 2015/0066038 A1 | 3/2015 | McGinley et al. |
| 2015/0080966 A1 | 3/2015 | Anderson |
| 2015/0134010 A1 | 5/2015 | Zlotolow |
| 2015/0141999 A1 | 5/2015 | McGinley et al. |
| 2015/0148805 A1 | 5/2015 | McGinley et al. |
| 2015/0148806 A1 | 5/2015 | McGinley et al. |
| 2015/0272608 A1 | 10/2015 | Gladstone |
| 2016/0051265 A1 | 2/2016 | Jones et al. |
| 2016/0120553 A1 | 5/2016 | Xie |
| 2016/0128704 A1 | 5/2016 | McGinley et al. |
| 2016/0192974 A1 | 7/2016 | Clain |
| 2016/0206328 A1 | 7/2016 | Lo et al. |
| 2016/0278802 A1 | 9/2016 | Cihak et al. |
| 2017/0007289 A1 | 1/2017 | McGinley et al. |
| 2017/0128081 A1 | 5/2017 | McGinley |
| 2017/0143396 A1 | 5/2017 | McGinley et al. |
| 2017/0143440 A1 | 5/2017 | McGinley et al. |
| 2017/0290602 A1 | 10/2017 | Germain et al. |
| 2017/0303990 A1 | 10/2017 | Benamou et al. |
| 2017/0340374 A1 | 11/2017 | Xie et al. |
| 2018/0221032 A1 | 8/2018 | Garcia et al. |
| 2021/0085340 A1 | 3/2021 | Schornagel et al. |
| 2021/0186524 A1* | 6/2021 | Carusillo ............... A61B 90/06 |
| 2022/0211391 A1* | 7/2022 | Carusillo ........... A61B 17/1622 |

FOREIGN PATENT DOCUMENTS

| | | |
|---|---|---|
| AU | 2014315652 B2 | 5/2019 |
| CN | 101530341 A | 9/2009 |
| CN | 204394613 U | 6/2015 |
| CN | 106163427 A | 11/2016 |
| DE | 4324134 C1 | 1/1995 |
| EP | 1330192 A2 | 7/2003 |
| EP | 1374784 A1 | 1/2004 |
| EP | 2800531 A1 | 11/2014 |
| EP | 3041419 B1 | 1/2019 |
| EP | 3065650 B1 | 1/2019 |
| FI | 110840 B | 4/2003 |
| JP | 1559620 S | 9/2016 |
| JP | 2018516036 A | 6/2018 |
| KR | 20100050763 A | 5/2010 |
| WO | 0166024 A1 | 9/2001 |
| WO | 03013372 A2 | 2/2003 |
| WO | 2007002230 A1 | 1/2007 |
| WO | 2009158115 A1 | 12/2009 |
| WO | 2010028046 A1 | 3/2010 |
| WO | 2013029582 A1 | 3/2013 |
| WO | 2013098555 A1 | 7/2013 |
| WO | 2013173138 A1 | 11/2013 |
| WO | 2015006296 A1 | 1/2015 |
| WO | 2015034562 A1 | 3/2015 |
| WO | 2015070159 A1 | 5/2015 |
| WO | 2016036756 A1 | 3/2016 |
| WO | 2016049467 A1 | 3/2016 |
| WO | 2016199152 A1 | 12/2016 |
| WO | 2017040783 A1 | 3/2017 |
| WO | 2017075044 A1 | 5/2017 |
| WO | 2017075060 A1 | 5/2017 |
| WO | 2017075224 A1 | 5/2017 |
| WO | 2017078754 A1 | 5/2017 |
| WO | 2017083992 A1 | 5/2017 |
| WO | 2018140646 A1 | 8/2018 |
| WO | 2018169565 A1 | 9/2018 |
| WO | 2018183002 A1 | 10/2018 |
| WO | 2019035096 A1 | 2/2019 |
| WO | 2019040381 A1 | 2/2019 |

OTHER PUBLICATIONS

English language abstract for FI 110840 B extracted from espacenet.com database on Nov. 21, 2022, 2 pages.

English language abstract and machine-assisted English translation for JP 2018-516036 A extracted from espacenet.com database on Nov. 18, 2021, 80 pages.

International Search Report for Application No. PCT/US2020/033288 dated Dec. 11, 2020, 4 pages.

Partial International Search Report for Application No. PCT/US2020/033288 dated Sep. 10, 2020, 2 pages.

U.S. Appl. No. 17/611,481, filed Nov. 15, 2021.

English language abstract and machine-assisted English translation for DE 4 324 134 C1 extracted from espacenet.com database on Mar. 30, 2022, 9 pages.

Demsey, Daniel et al., "Feasibility of Using Opticat Sensing to Measure Bore Depth in Surgical Bone Drilling", 17th Annual Meeting of the International Society for Computer Assisted Orthopaedic Surgery, CAOS 2017, 7 pages.

English language abstract and machine-assisted English translation for CN 101530341 extracted from espacenet.com database on Apr. 15, 2020, 7 pages.

English language abstract and machine-assisted English translation for CN 204394613 extracted from espacenet.com database on Apr. 15, 2020, 7 pages.

English language abstract and machine-assisted English translation for KR 20100050763 extracted from espacenet.com database on Apr. 15, 2020, 6 pages.

English language abstract and machine-assisted English translation for WO 2013/029582 extracted from espacenet.com database on Apr. 15, 2020, 10 pages.

English language abstract for EP 1 330 192 extracted from espacenet.com database on Apr. 15, 2020, 1 page.

English language abstract for WO 01/66024 extracted from espacenet.com database on Mar. 1, 2018, 2 pages.

English language abstract not found for JP 1559620; however, see English language equivalent U.S. Pat. No. D. 732,364. Original document unavailable, 1 page.

International Search Report for Application No. PCT/IB2018/056251 dated Jan. 3, 2019, 4 pages.

McGinley Orthopaedic Innovations, "IntelliSense Drill Brochure", 2015, 4 pages.

Stryker, "Cordless Driver 3 Accessories Brochure", 2017, 2 pages.

* cited by examiner

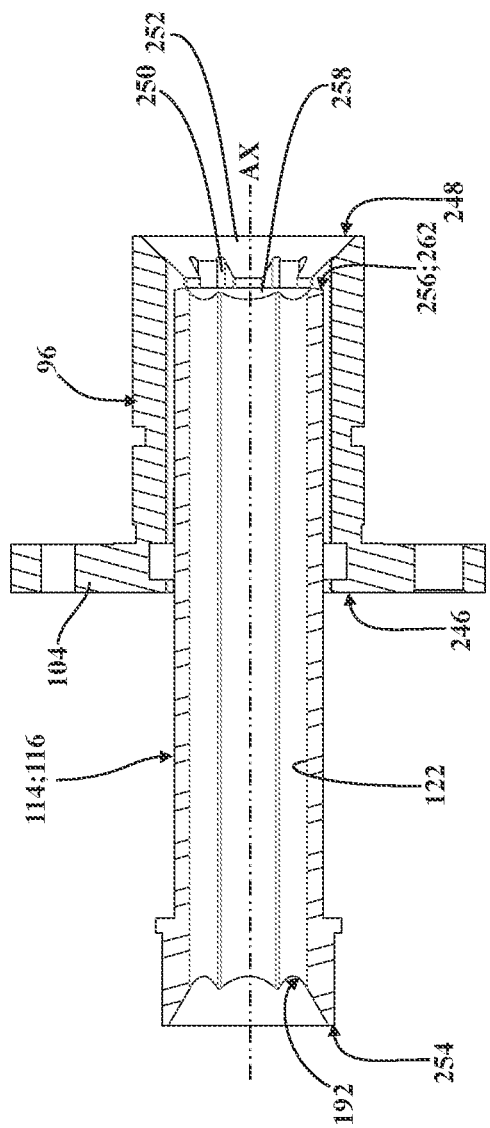
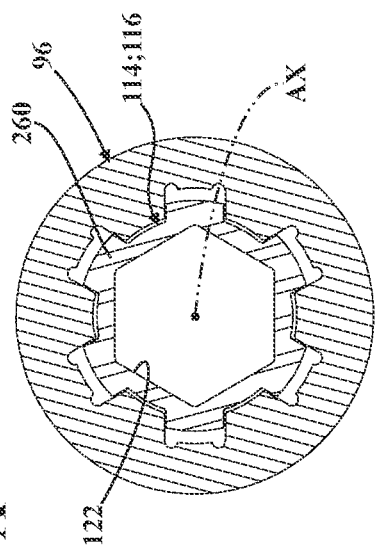
FIG. 17A
FIG. 18A
FIG. 19A

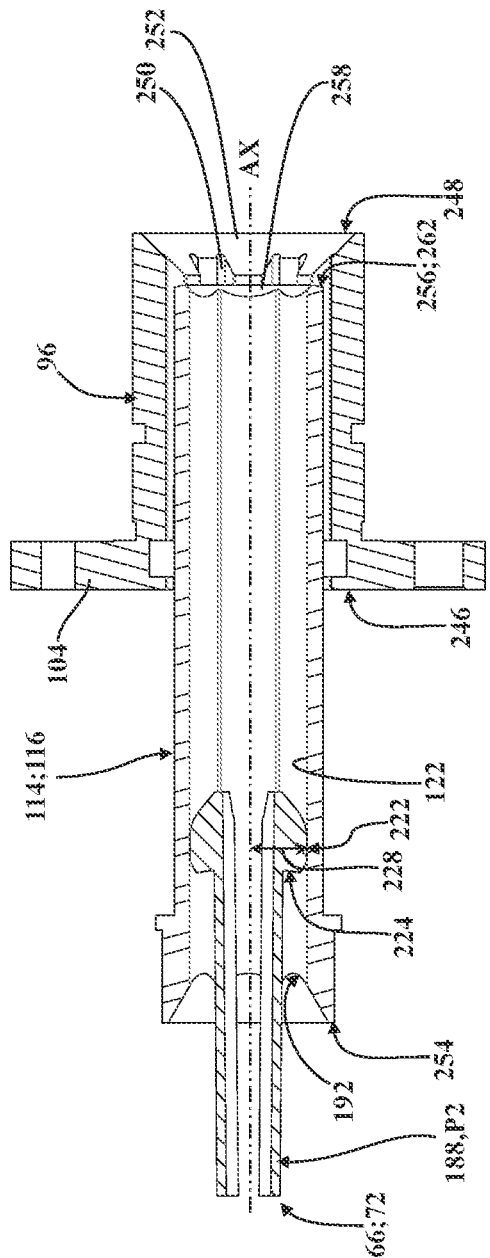
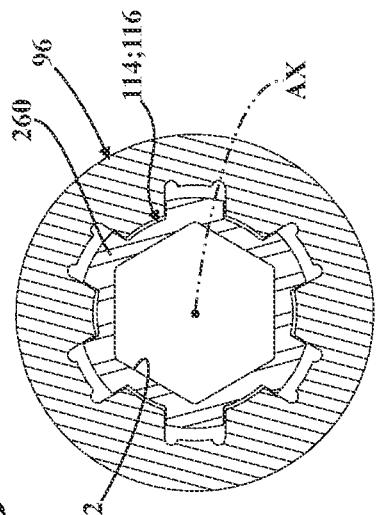
FIG. 17B
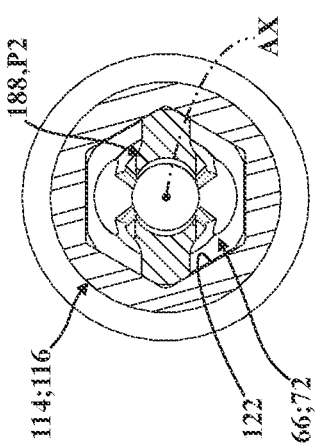
FIG. 18B
FIG. 19B

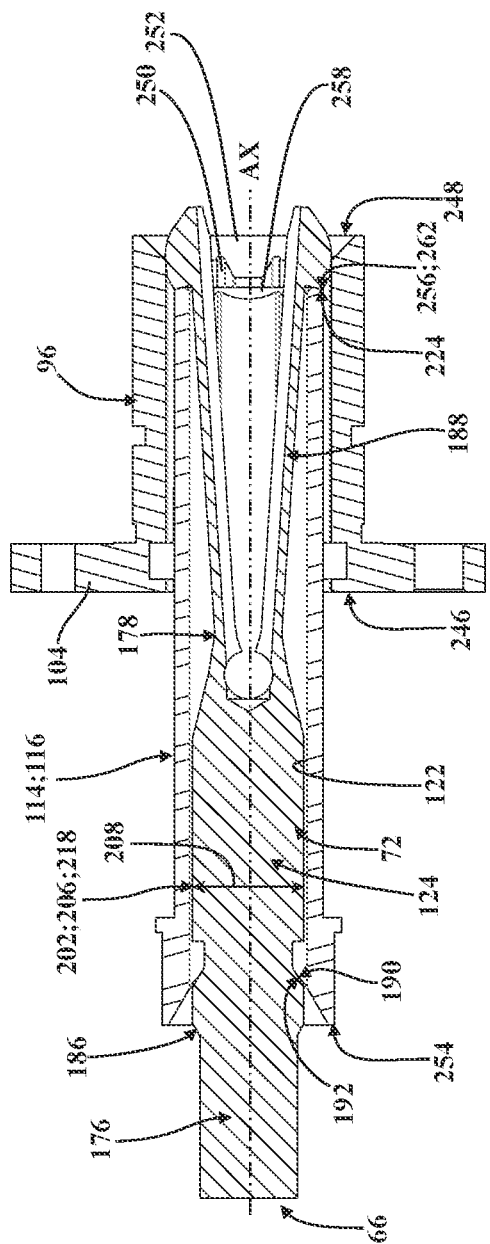
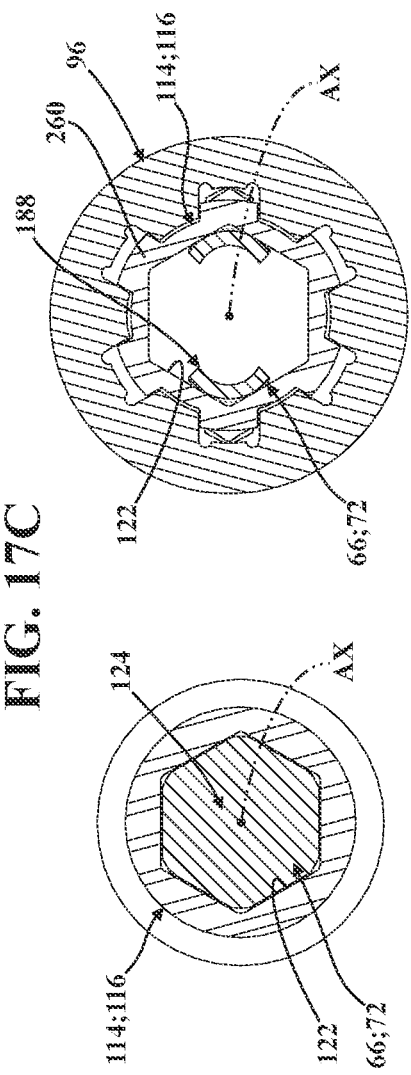
FIG. 17C
FIG. 18C
FIG. 19C

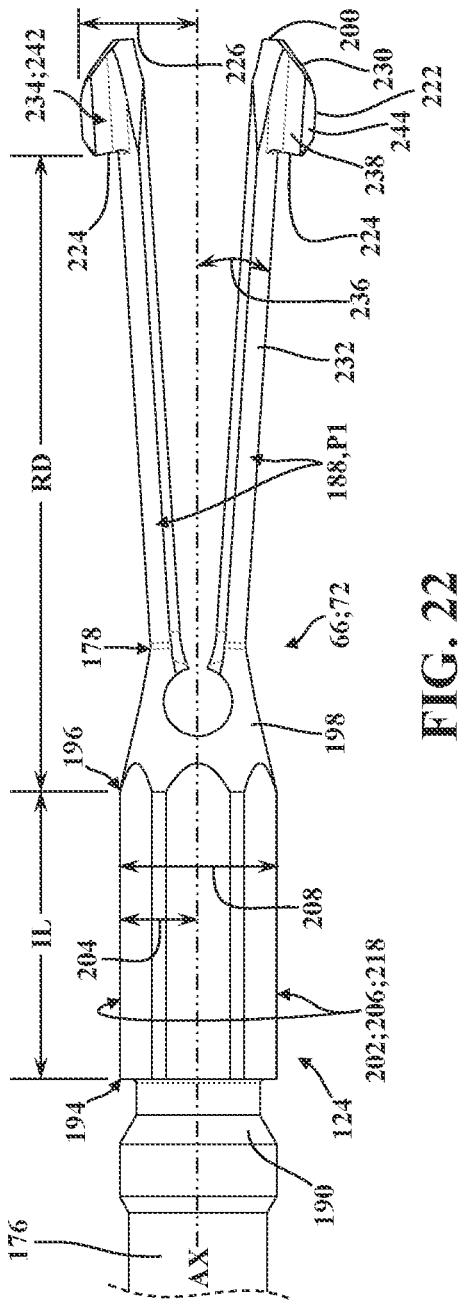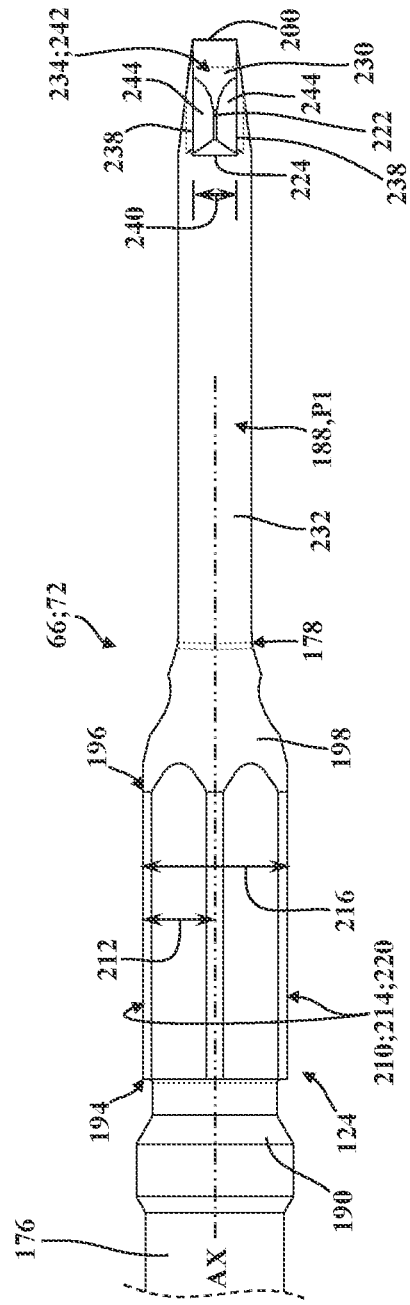

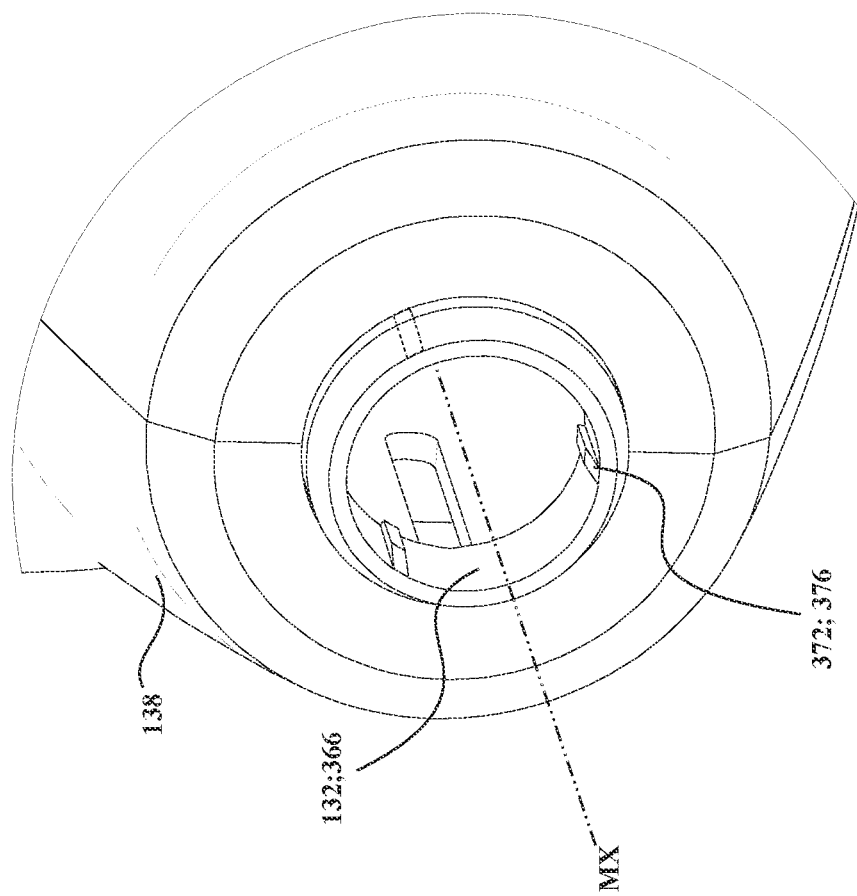

SURGICAL HANDPIECE SYSTEM FOR DEPTH MEASUREMENT AND RELATED ACCESSORIES

CROSS-REFERENCE TO RELATED APPLICATION

The subject patent application is a U.S. Continuation patent application of U.S. Ser. No. 16/639,690 filed on Feb. 17, 2020, which claims priority to International Patent Application No. PCT/IB2018/056251, filed on Aug. 17, 2018, which is a continuation-in-part patent application of U.S. patent application Ser. No. 15/887,507 filed on Feb. 2, 2018; now U.S. Pat. No. 10,159,495 issued Dec. 25, 2018, which claims priority to and all the benefits of U.S. Provisional Patent Application No. 62/618,134 filed on Jan. 17, 2018, U.S. Provisional Patent Application No. 62/548,357 filed on Aug. 21, 2017, and U.S. Provisional Patent Application No. 62/546,760 filed on Aug. 17, 2017, the disclosures of which are hereby incorporated by reference in their entirety.

TECHNICAL FIELD

The present disclosure relates, generally, to a surgical handpiece and related accessories for measuring depth of bore holes.

BACKGROUND

Conventional medical and surgical procedures routinely involve the use of surgical tools and instruments which allow surgeons to approach and manipulate surgical sites. By way of non-limiting example, rotary instruments such as handheld drills are commonly utilized in connection with orthopedic procedures to address various musculoskeletal conditions, such as trauma, sports injuries, degenerative diseases, joint reconstruction, and the like. In procedures where handheld drills or similar surgical instruments are employed, rotational torque selectively generated by an actuator (e.g., an electric motor) is used to rotate a releasably-attachable drill bit or other surgical attachments at different speeds. Drill bits utilized in connection with medical and surgical procedures are typically realized as single-use components that are replaced between procedures.

While handheld surgical instruments and drill bits are routinely utilized to assist in the performance of a variety of different types of medical and/or surgical procedures, there is a need in the art to continuously improve such drill bits and handheld surgical instruments.

BRIEF DESCRIPTION OF THE DRAWINGS

FIG. 17A is a sectional view taken along line 17-17 in FIG. 16, depicting the proximal portion of the drive cannula disposed within the output hub as illustrated in FIG. 15B.

FIG. 17B is another sectional view of the proximal portion of the drive cannula and the output hub of FIG. 17A, shown with the resilient arms of the drill bit of FIGS. 1-2, 4-5, 7B-7I, and 15B-15C disposed within the bore of the proximal portion of the drive cannula.

FIG. 17C is another sectional view of the proximal portion of the drive cannula, the output hub, and the drill bit of FIG. 17B, shown with the resilient arms of the drill bit disposed in abutment with the lock surfaces of the proximal portion of the drive cannula as illustrated in FIG. 15C.

FIG. 18A is a sectional view taken along line 18-18 in FIG. 16, depicting the profile of the bore of the proximal portion of the drive cannula.

FIG. 18B is another sectional view of the proximal portion of the drive cannula of FIG. 18A, shown with the resilient arms of the drill bit of FIGS. 1-2, 4-5, 7B-7I, and 15B-15C disposed within and abutting against the bore of the proximal portion of the drive cannula, the drill bit being arranged as illustrated in FIG. 17B.

FIG. 18C is another sectional view of the proximal portion of the drive cannula and the drill bit of FIG. 18B, shown with the interface disposed within the bore of the proximal portion of the drive cannula.

FIG. 19A is a sectional view taken along line 19-19 in FIG. 16, depicting splined engagement between the proximal portion of the drive cannula and the output hub adjacent to the lock surfaces of the proximal portion of the drive cannula.

FIG. 19B is another sectional view of the proximal portion of the drive cannula and the output hub.

FIG. 19C is another sectional view of the proximal portion of the drive cannula and the output hub of FIGS. 19A-19B, shown with portions of the resilient arms of the drill bit disposed within and abutting against the bore of the proximal portion of the drive cannula, the drill bit being arranged as illustrated in FIG. 17C.

FIG. 22 is a left-side view of the portions of the drill bit illustrated in FIGS. 20-21.

FIG. 23 is a top-side view of the portions of the drill bit illustrated in FIGS. 20-22.

FIG. 66 is a perspective view of the measurement module of FIGS. 55-64 showing protrusions extending from distal portion of the bushing into a bore of the bushing.

DETAILED DESCRIPTION

Figure 1:
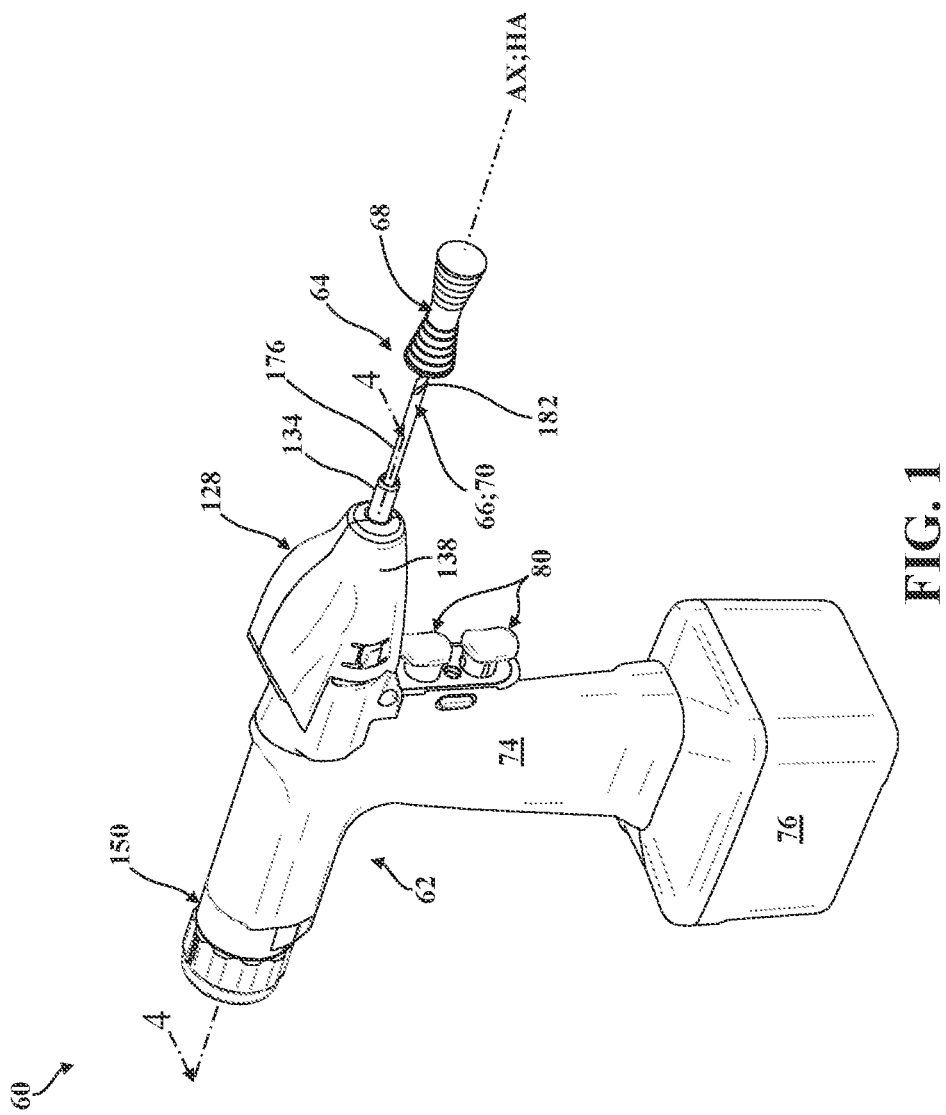
FIG. 1 is perspective view of a surgical handpiece system comprising a surgical handpiece assembly and a measurement module, the surgical handpiece assembly shown having a drill bit and a tip protector according to one configuration.
Figure 2:
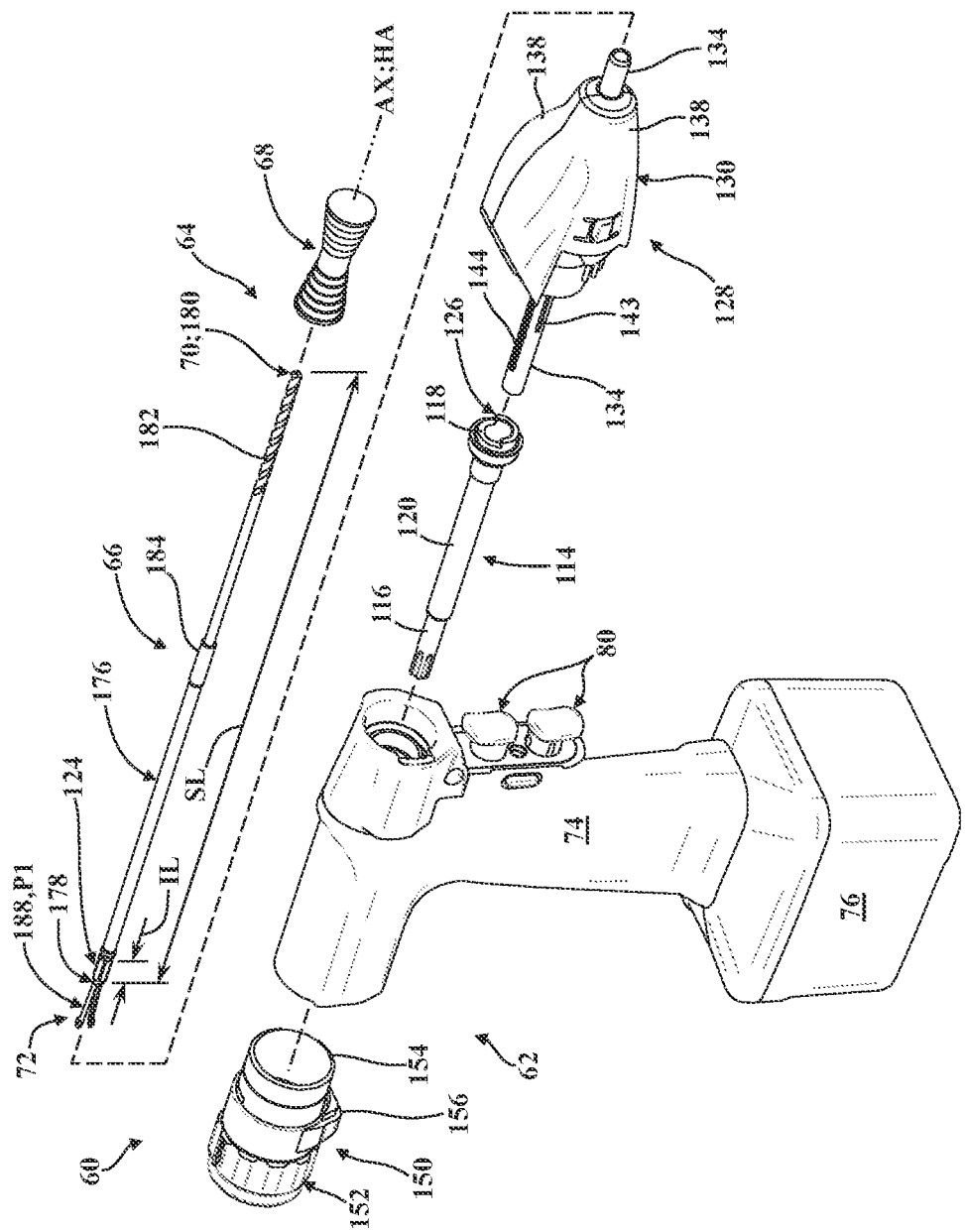
FIG. 2 is a partially-exploded perspective view of the surgical handpiece system of FIG. 1, with the surgical handpiece system shown having a measurement module, a drive cannula, and a release assembly spaced from a handpiece housing assembly, and with the end effector assembly removed from the surgical handpiece assembly and shown with the tip protector spaced from a distal cutting tip portion of the drill bit.

With reference to the drawings, where like numerals are used to designate like structure throughout the several views, a surgical handpiece system is shown at 60 in FIGS. 1-2 for performing an operational function associated with medical and/or surgical procedures. In the representative configuration illustrated herein, the surgical handpiece system 60 is employed to facilitate penetrating tissue of a patient, such as bone. To this end, the illustrated configuration of the surgical handpiece system 60 comprises a surgical handpiece assembly 62 and an end effector assembly, generally indicated at 64. The end effector assembly 64, in turn, comprises a drill bit 66 and a tip protector 68. As is best depicted in FIG. 2, the drill bit 66 extends generally longitudinally along an axis AX between a cutting tip portion, generally indicated at 70, and an insertion portion, generally indicated at 72. As is described in greater detail below, the cutting tip portion 70 is configured to engage tissue, and the insertion portion 72 is configured to facilitate releasable attachment of the drill bit 66 to the surgical handpiece assembly 62.

In order to help facilitate attachment of the drill bit 66 to the surgical handpiece assembly 62, in some configurations, the tip protector 68 is configured to releasably secure to the cutting tip portion 70 of the drill bit 66 while concealing at least a portion of the cutting tip portion 70 of the drill bit 66, thereby allowing a user (e.g., a surgeon) of the surgical handpiece system 60 to handle and position the drill bit 66 safely during attachment to the surgical handpiece assembly 62. Once the end effector assembly 64 has been attached to the surgical handpiece assembly 62, the tip protector 68 is subsequently removed from the cutting tip portion 70 of the drill bit 66, and the surgical handpiece system 60 can then be utilized to penetrate tissue. Configurations of the tip protector 68 are described in greater detail below in connection with FIGS. 34-46.

While drill bits are described about, it should be appreciated that the coupling geometry described throughout with respect to the drill bit may be used in conjunction with any other type of surgical end effector, especially rotary surgical end effectors, such as a cannulated drill bit, a rongeur, etc.

Referring now to FIGS. 1-19C, in the representative configuration illustrated herein, the surgical handpiece assembly 62 is realized as a handheld drill with a pistol-grip shaped handpiece housing assembly 74 which releasably attaches to a battery 76 (battery attachment not shown in detail). However, it is contemplated that the handpiece housing assembly can have any suitable shape with or without a pistol grip. While the illustrated surgical handpiece assembly 62 employs a battery 76 which is releasably attachable to the handpiece housing assembly 74 to provide power to the surgical handpiece assembly 62 utilized to rotate the drill bit 66, it will be appreciated that the surgical handpiece assembly 62 may be configured in other ways, such as with an internal (e.g., non-removable) battery, or with a tethered connection to an external console, power supply, and the like. Other configurations are contemplated.

The handpiece housing assembly 74 has a proximal region adjacent the release assembly 150 (described in greater detail further below) and a distal region opposite the proximal region. Unless otherwise specified "Proximal" is understood to mean toward a user holding the handpiece housing assembly. "Distal" is understood to mean away from the user holding the handpiece housing assembly.

Figure 3:
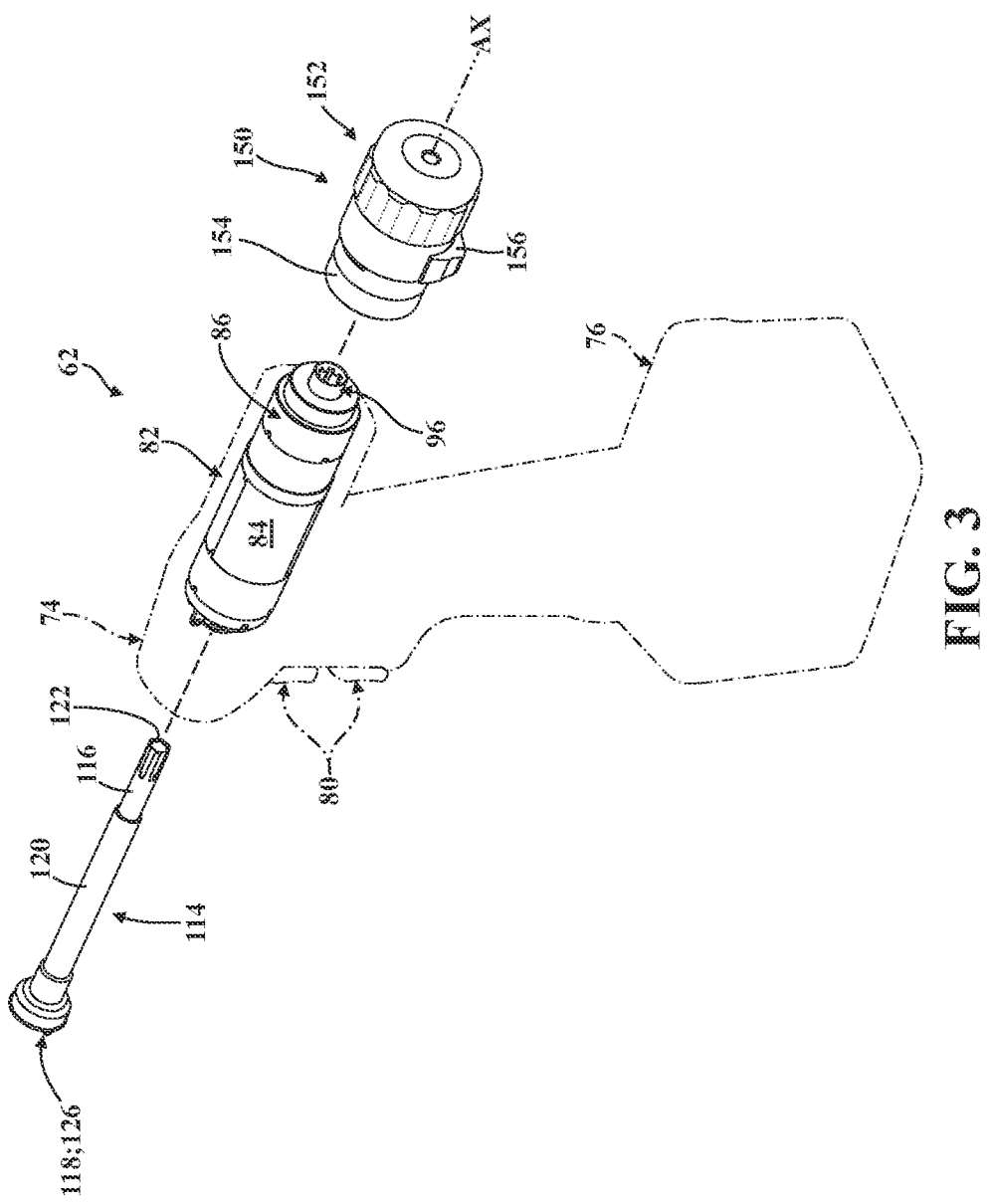
FIG. 3 is a partially-exploded perspective view of portions of the surgical handpiece assembly of FIGS. 1-2, shown with the drive cannula and the release assembly spaced from a phantom outline of the handpiece housing assembly to depict an actuator assembly.

In the illustrated configuration, the battery 76 or other power source provides power to a controller 78 (depicted schematically in FIG. 6) which, in turn, is disposed in communication with a user input device 80 and an actuator assembly 82 (see also FIG. 3). The user input device 80 and the actuator assembly 82 are each supported by the handpiece housing assembly 74. The controller 78 is generally configured to facilitate operation of the actuator assembly 82 in response to actuation of the user input device 80. The user input device 80 has a trigger-style configuration in the illustrated configuration, is responsive to actuation by a user (e.g., a surgeon), and communicates with the controller 78, such as via electrical signals produced by magnets and Hall effect sensors. Thus, when the surgeon actuates the user input device 80 to operate the surgical handpiece assembly 62, the controller 78 directs power from the battery 76 to the actuator assembly 82 which, in turn, generates rotational torque employed to rotate the drill bit 66 or other surgical end effector, as described in greater detail below. Those having ordinary skill in the art will appreciate that the handpiece housing assembly 74, the battery 76, the controller 78, and the user input device 80 could each be configured in a number of different ways to facilitate generating rotational torque without departing from the scope of the present disclosure.

Figure 6:
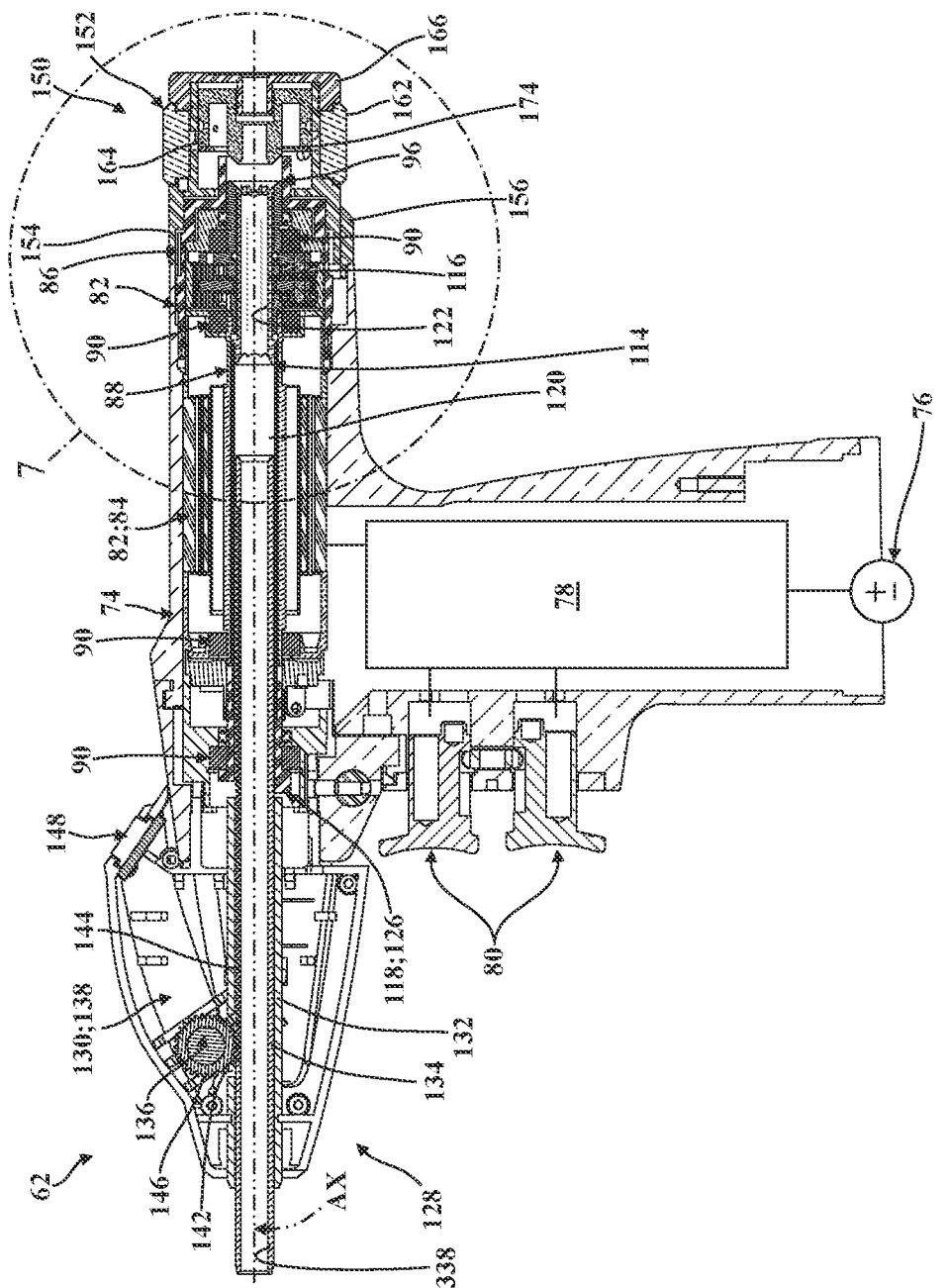
FIG. 6 is a sectional view taken longitudinally through the surgical handpiece assembly of FIGS. 1-5, with the end effector assembly removed from the surgical handpiece assembly.
Figure 9:
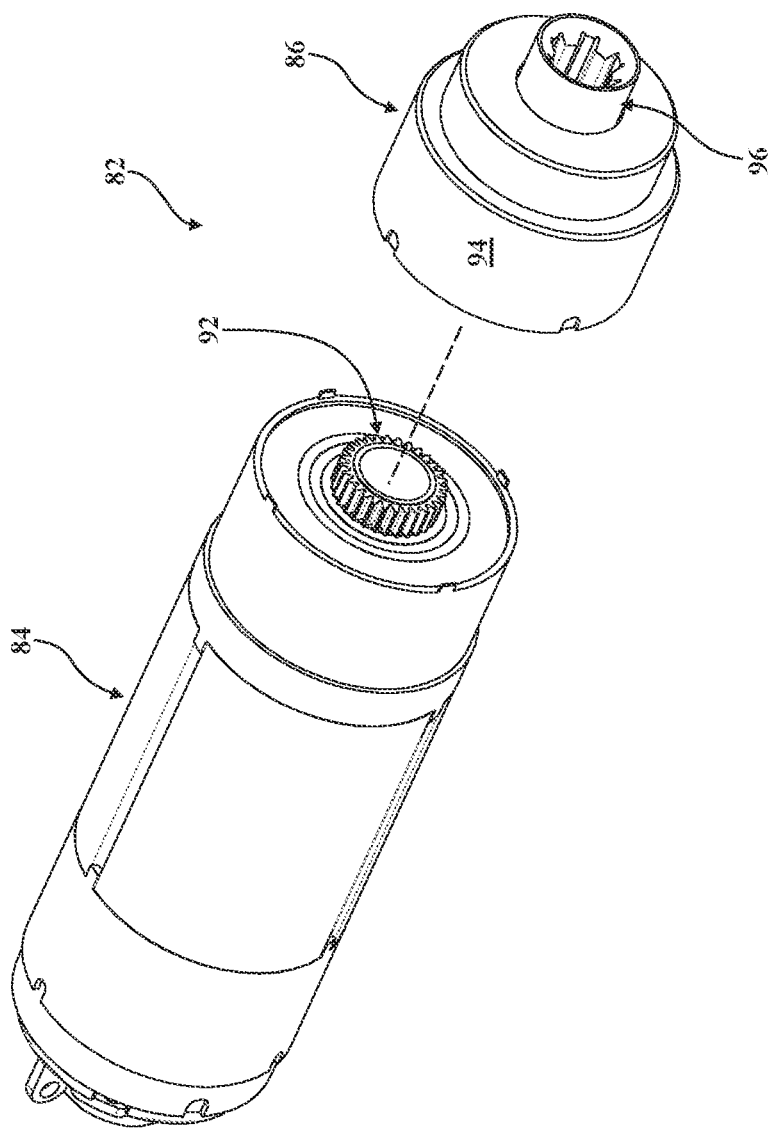
FIG. 9 is a partially-exploded view of the actuator assembly of FIGS. 3-7I, shown having a motor with a drive gear, and a gearset with an output hub.
Figure 10:
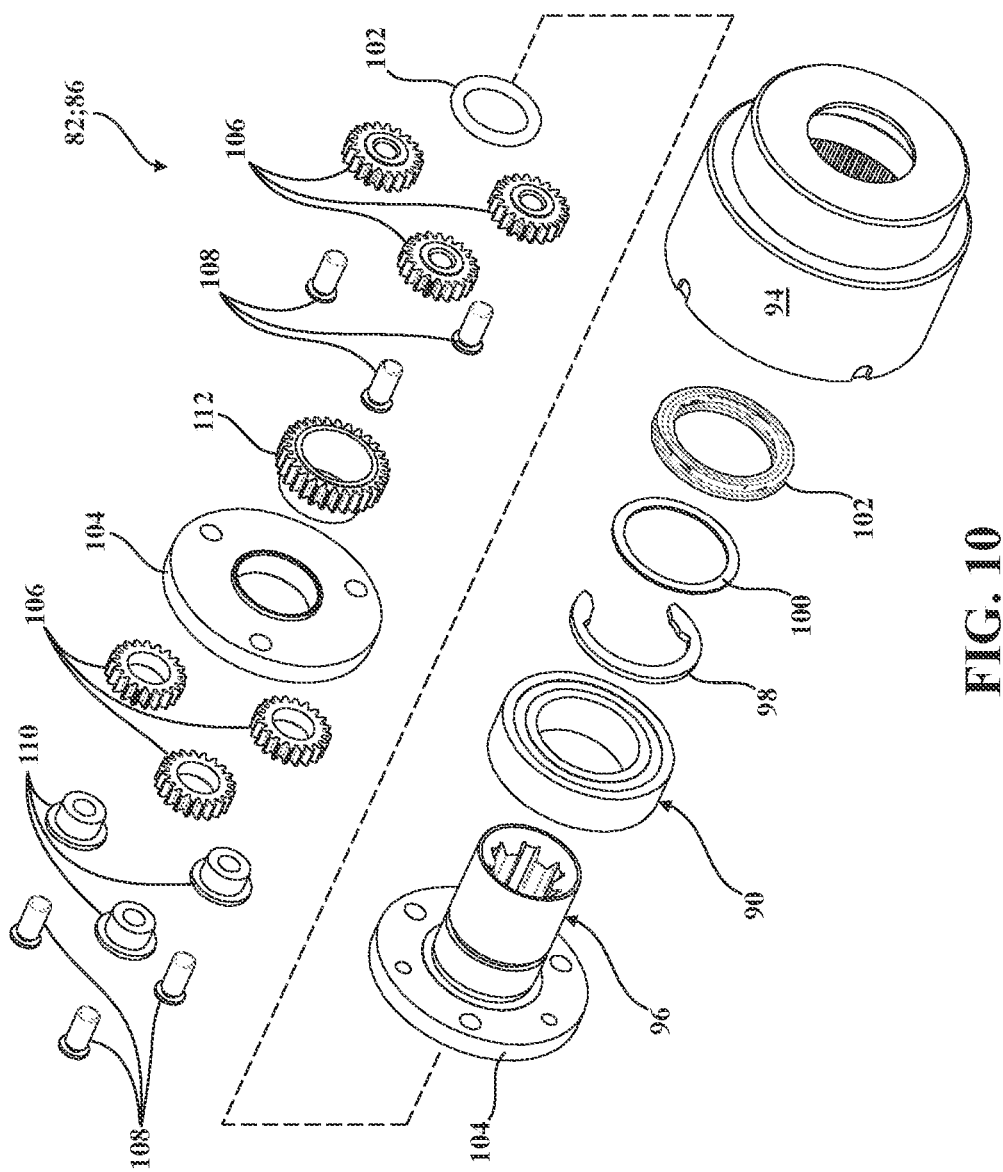
FIG. 10 is an exploded perspective view of the gearset of FIG. 9.
Figure 11:
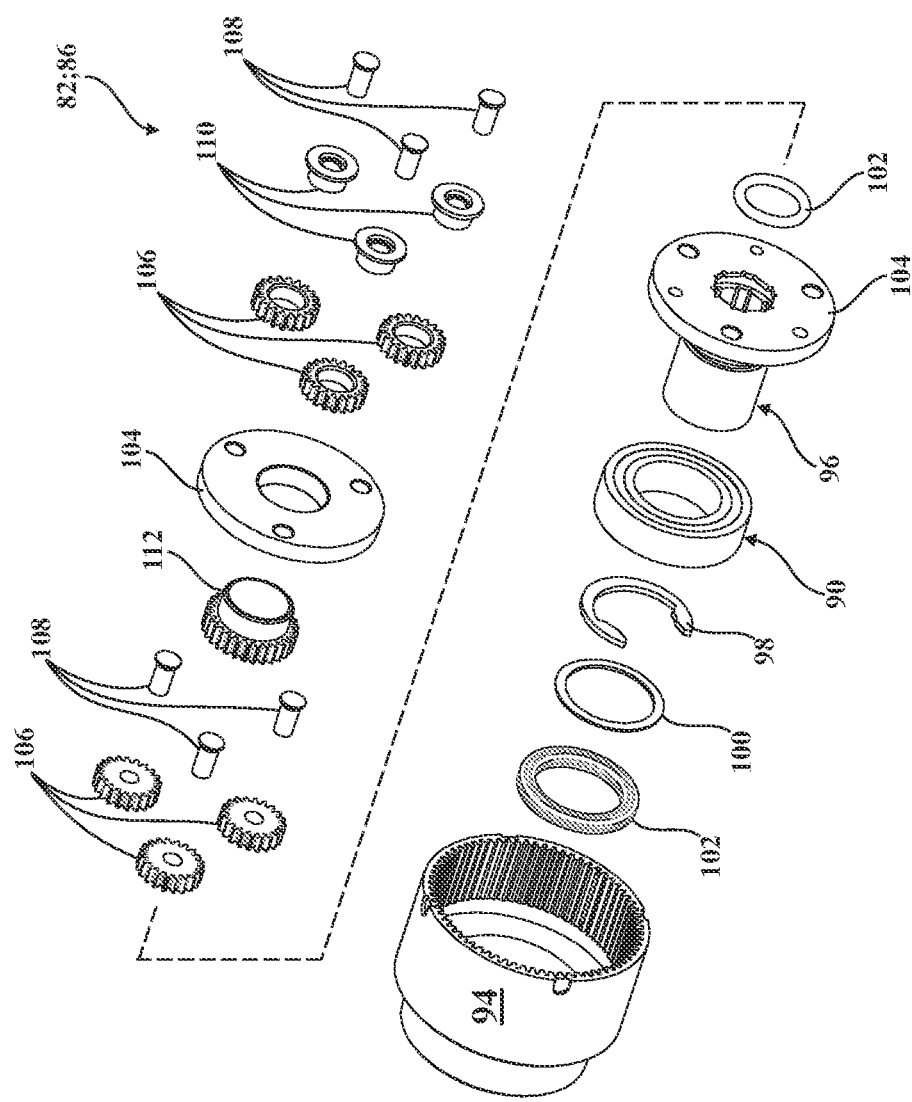
FIG. 11 is another exploded perspective view of the gearset of FIGS. 9-10.

As is best shown in FIG. 9, the actuator assembly 82 generally comprises an electric motor 84 and a gearset 86 which are each supported within the handpiece housing assembly 74. The motor 84 is configured to selectively generate rotational torque in response to commands, signals, and the like received from the controller 78. As is best shown in FIG. 6, the motor 84 comprises a rotor cannula 88 supported for rotation about the axis AX by a pair of bearings 90. A drive gear 92 arranged adjacent to the gearset 86 (see FIG. 9) is coupled to and rotates concurrently with the rotor cannula 88, and is employed to transmit rotational torque to the gearset 86. To this end, in the illustrated configuration, and as is shown in FIGS. 10-11, the gearset 86 is realized as two-stage compound planetary arrangement and generally comprises a ring gear housing 94 which, among other things, rotationally supports an output hub 96 via a bearing 90, as well as one or more retaining clips 98, washers 100, and/or seals 102. The ring gear housing 94 is coupled to a motor housing 85 of the motor 84. However, other configurations of the gearset 86 are contemplated. For example, the motor and/gear set shown in International Patent Publ. No. WO 2007/002230 entitled "Surgical Handpiece with Compact Clutch and Anti-Wobble Coupling Head" and filed on Jun. 20, 2006, is hereby incorporated by reference in its entirety, may be used for the surgical handpiece assembly.

With continued reference to FIGS. 10-11, in the illustrated configuration, the output hub 96 of the gearset 86 comprises an integrated carrier 104 to which three planet gears 106 are supported via an arrangement of shafts 108 and, in some configurations, bushings 110 interposed between the shafts 108 and the planet gears 106. The planet gears 106 are disposed in meshed engagement with the ring gear housing 94 and also with a sun gear 112. The sun gear 112 rotates concurrently with a second carrier 104 which, in turn, supports an additional three planet gears 106 via respective shafts 108 and bushings 110. These additional planet gears 106 are likewise disposed in meshed engagement with the ring gear housing 94, and are disposed in meshed engagement with the drive gear 92 of the motor 84. Thus, rotation of the drive gear 92 via actuation of the motor 84 effects concurrent rotation of the output hub 96. As is described in greater detail below in connection with FIGS. 15A-15C and 17A-19C, the output hub 96 rotates concurrently with the drill bit 66. Those having ordinary skill in the art will appreciate that the actuator assembly 82 could be configured in other ways without departing from the scope of the present disclosure. By way of non-limiting example, while the illustrated actuator assembly 82 employs a compound planetary arrangement to adjust rotational speed and torque between the drive gear 92 of the motor 84 and the output hub 96, other types of gearsets 86 could be utilized in some configurations. Moreover, while the illustrated actuator assembly 82 employs an electrically-powered brushless DC motor to generate rotational torque, other types of prime movers could be utilized. Other configurations are contemplated.

As noted above, rotational torque generated by the motor 84 effects rotation of the output hub 96 which, in turn, rotates concurrently with the drill bit 66. To this end, and as is best shown in FIGS. 2-5 and 8, the surgical handpiece assembly 62 further comprises a drive cannula 114 which generally extends through the various cannulated components of the actuator assembly 82 into splined engagement with the output hub 96 of the gearset 86. As is described in greater detail below, the drive cannula 114 is configured to facilitate releasable attachment between the drill bit 66 and the surgical handpiece assembly 62. The drive cannula 114 generally comprises a proximal portion 116, a distal portion 118, and a body portion 120. The proximal portion 116, distal portion 118, and the body portion 120 of the drive cannula 114 are supported for rotation about the axis AX concurrently. In some configurations, the portions 116, 118, 120 of the drive cannula 114 are integrally formed. In other configurations, the portions 116, 118, 120 of the drive cannula 114 may be formed separately from and subsequently attached to each other via welding, brazing, adhering, bonding, or any suitable process sufficient to operatively attach the portions 116, 118, 120 of the drive cannula 114 together. In some Figures shown herein, the body portion 120 and the distal portion 118 are removed to best illustrate the relationship of the proximal portion 116 of the drive cannula 114 to other components of the surgical handpiece assembly 62. It is appreciated that the body portion 120 and the distal portion 118 are coupled to the proximal portion 116 of the drive cannula 114 as illustrated in FIG. 2. Furthermore, it should be appreciated that the drive cannula may take other forms other than described above, and may simply be a drive element that transfers torque without including a lumen.

Figure 8:
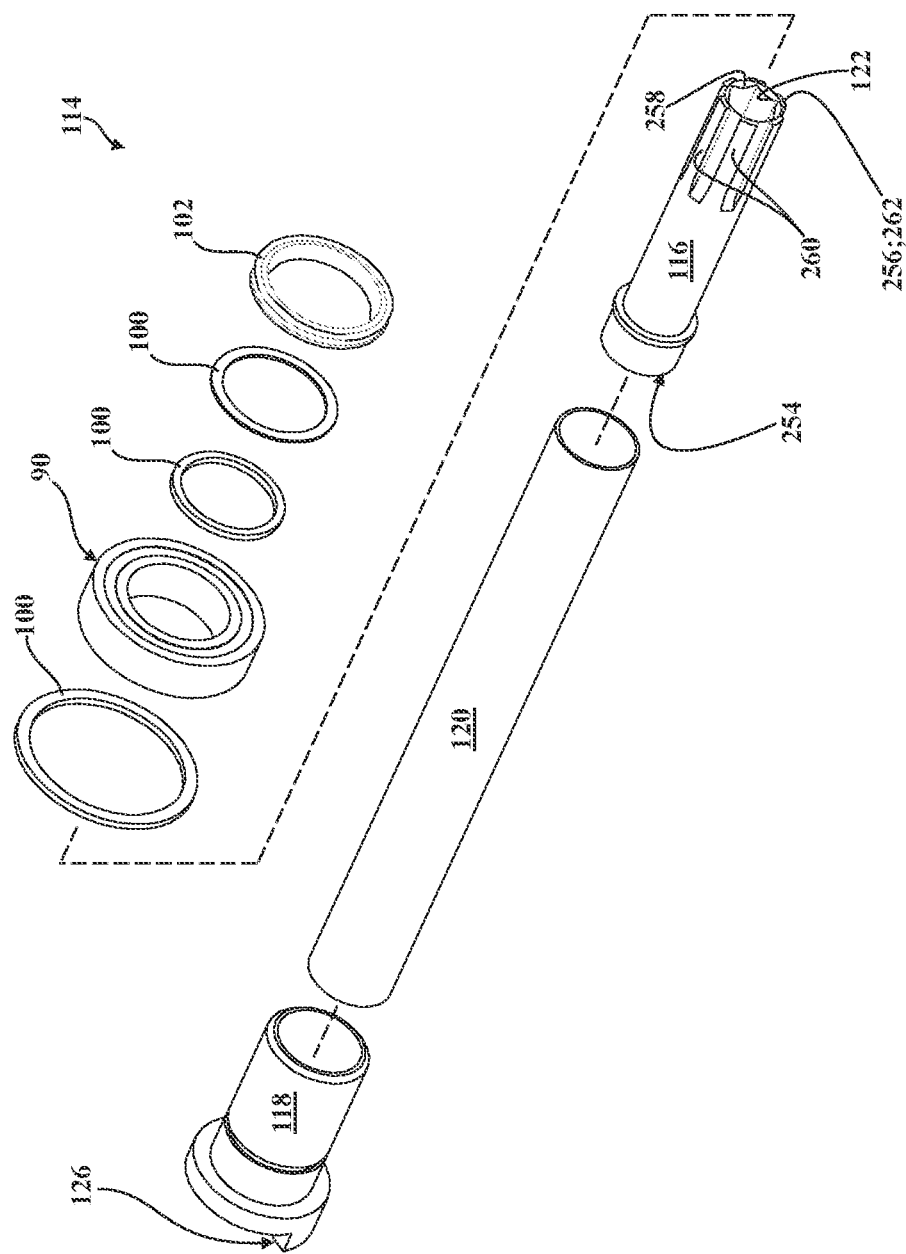
FIG. 8 is an exploded perspective view of the drive cannula of FIGS. 2-7I.

The drive cannula 114 is supported for rotation about the axis AX within the handpiece housing assembly 74 via splined engagement with the output hub 96 adjacent the proximal portion 116 of the drive cannula 114, and via an arrangement of bearings 90, snap rings 100, and seals 102 adjacent the distal portion 118 of the drive cannula 114 (see FIGS. 6 and 8). As is described in greater detail below in connection with FIGS. 15A-33, the proximal portion 116 of the drive cannula 114 comprises a generally hexagonal bore 122 which is employed to receive an interface 124 of the drill bit 66 (see FIG. 2) so as to facilitate concurrent rotation between the drill bit 66 and the drive cannula 114. As will be appreciated from the subsequent description below, the interface 124 is defined by physical structure extending outwardly from the axis AX such that the interface 124 is configured to be driven externally. As is best shown in FIG. 8, the body portion 120 of the drive cannula 114 and the distal portion 118 of the drive cannula 114 each have cylindrical bores. However, other configurations of the body portion 120 of the drive cannula 114 and the distal portion 118 of the drive cannula 114 can have non-cylindrical bores, such as polygonal or oval bore profiles. Other configurations of the bearings, snap-rings and seals are also contemplated. Similarly, the engagement of the output member to the drive cannula/drive element may take any suitable form so long as torque gets transferred from the motor to the drive cannula/drive element.

As noted above, the proximal portion 116 of the drive cannula 114 is configured to engage the drill bit 66 to rotate the drill bit 66 about the axis AX. The internal surface defining the bore 122 of the proximal portion 116 of the drive cannula 114 comprises a first driving portion for transmitting torque to the drill bit 66. As will be described in greater detail below the distal portion 118 of the drive cannula 114 comprises a distal protrusion, generally indicated at 126, comprising a second driving portion which is provided to facilitate transmitting rotational torque when the surgical handpiece assembly 62 is utilized in connection with other applications besides rotating the drill bit 66. In the illustrated configurations, as best shown in FIGS. 2 and 8, the distal protrusion 126 extends distally and generally parallel to the axis AX and defines the distal end of the drive cannula 114. In other configurations, the distal protrusion 126 extends perpendicular to the axis AX. In still other configurations, the distal protrusion 126 extends at an oblique angle between perpendicular and parallel to the axis AX. In one configuration, the distal protrusion 126 operates as a drive dog/torque transmission geometry to transmit torque via interference coupling. More specifically, in the aforementioned configurations, the drive cannula 114 is configured such that the surgical handpiece assembly 62 can rotate, drive, or otherwise actuate a number of different types of surgical attachments, tools, modules, end effectors, and the like, which can be configured to engage and rotate concurrently with the distal protrusion 126 of the distal portion 118 of the drive cannula 114. It will be appreciated that this allows the same surgical handpiece assembly 62 to be utilized in a broad number of medical and/or surgical procedures. Details relating to the distal portion 118 of the drive cannula 114 will be discussed further below. However, it is contemplated that the drive cannula 114 could be configured differently in some configurations, such as to omit a distal protrusion 126 at the distal portion 118 of the drive cannula 114 in configurations where the surgical handpiece assembly 62 is configured for dedicated use with the drill bit 66 of the present disclosure.

Figure 4:
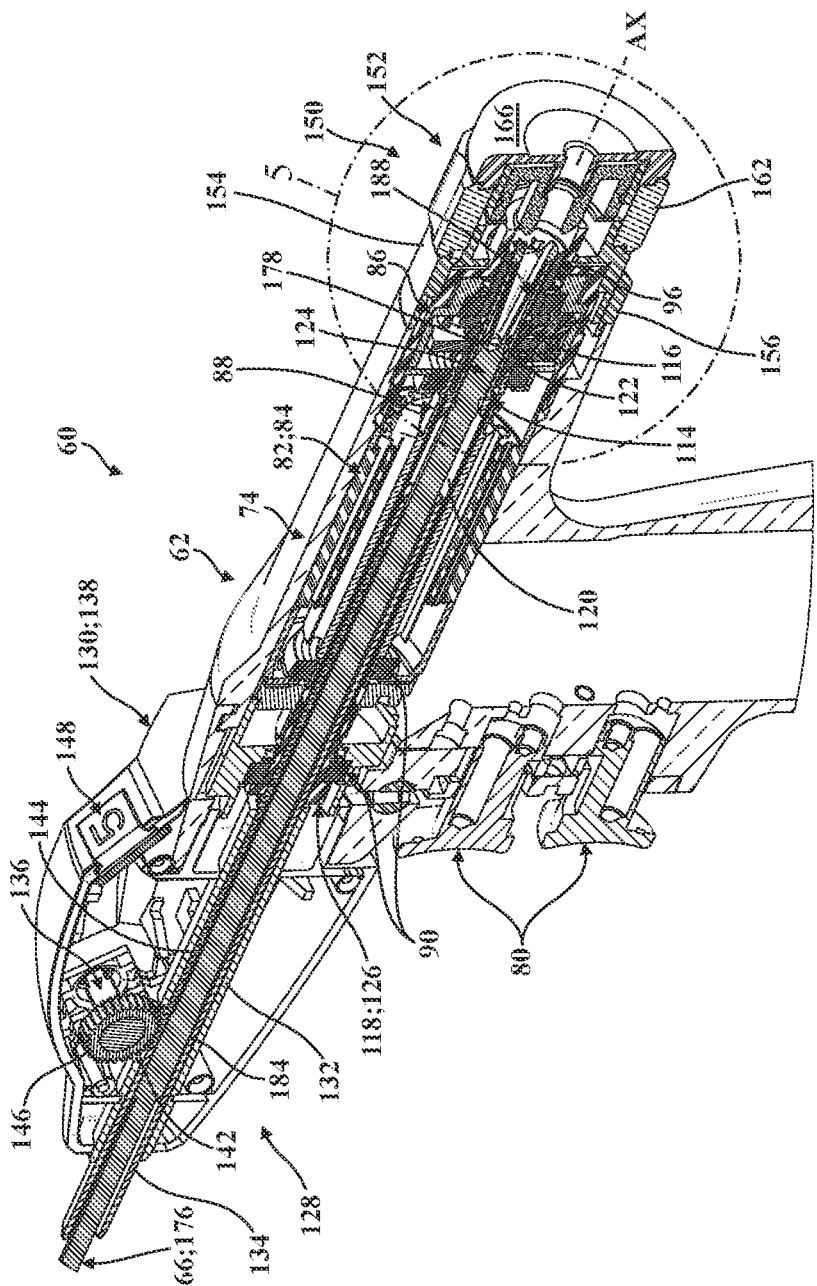
FIG. 4 is a partial isometric sectional view taken along line 4-4 in FIG. 1.
Figure 5:
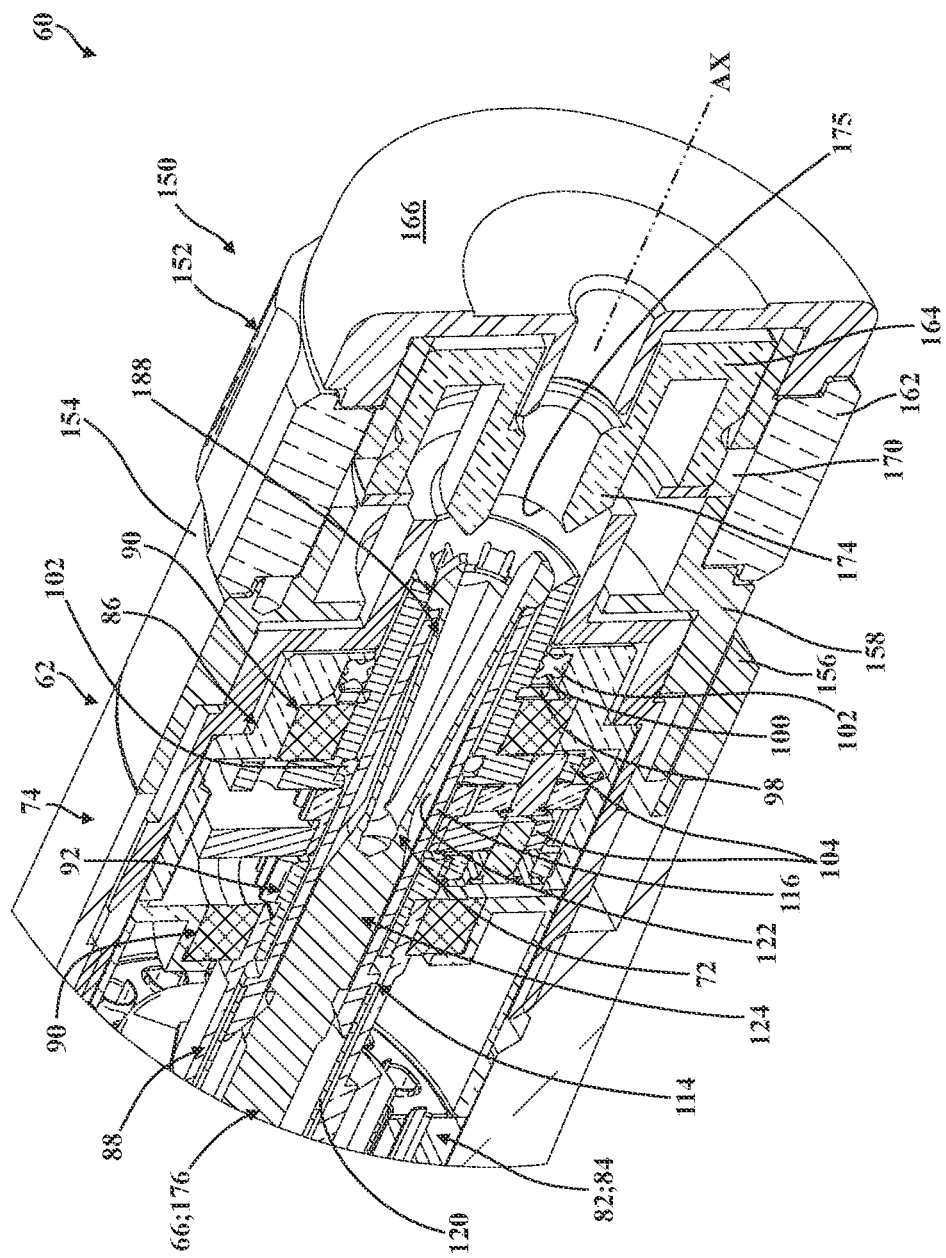
FIG. 5 is an enlarged detail view taken at indicia 5 in FIG. 4.

Referring now to FIGS. 1-2, 4, and 6, the illustrated configuration of the surgical handpiece system 60 further comprises a measurement module, generally indicated at 128, which is configured to releasably attach to the surgical handpiece assembly 62 to provide the surgeon with measurement functionality during use. To this end, and as is shown in FIGS. 4 and 6, the measurement module 128 generally comprises a housing 130, a guide bushing 132, a depth cannula 134, a displacement sensor assembly 136, a rotatable gear 146. In some configurations, the housing 130 is releasably attachable to the surgical handpiece assembly 62. In other configurations, the measurement module 128 is releasably attached to the handpiece housing assembly 74 in another manner. In certain configurations, the measurement module may include one or more buttons for controlling a function of the measurement module. Configurations for releasable attachment of the measurement module 128 to the handpiece housing assembly 74 are discussed in greater detail further below. The housing 130 generally supports the various components of the measurement module 128. The housing 130 illustrated in FIGS. 4 and 6 is formed as a pair of housing components 138 which interlock or otherwise attach together, and may be configured for disassembly to facilitate cleaning or servicing the measurement module 128. In the illustrated configurations, the housing components 138 and the guide bushing 132 comprise correspondingly-shaped features arranged to prevent relative axial and rotational movement therebetween, such as via notches formed in the guide bushing 132 which fit into webs or ribs formed in the housing components 138 (not shown in detail). For example, the guide bushing 132 may include one or more wings 133 (see FIGS. 63 and 65) to stabilize the measurement housing 138 and provide support for when buttons 135 (see FIGS. 62 and 64) of the measurement module are depressed. The wings 133 of the guide bushing 132 may sit within one or more recesses of the measurement housing 138. The guide bushing 132 further comprises a window 142 for use with the gear 146 as described in detail below.

The depth cannula 134 is disposed within the guide bushing 132 and is supported for translational movement along a measurement axis MX. When the measurement module 128 is attached to the surgical handpiece assembly, the measurement axis MX is arranged to be coaxial with the axis AX. An elongated recessed slot 143 (partially depicted in FIG. 2) is optionally formed transversely into the depth cannula 134 and extends longitudinally. While not specifically illustrated herein, the elongated recessed slot 143 is shaped and arranged to receive a travel stop element which, in turn, is supported by the housing 130 and likewise extends through an aperture formed transversely through the side of the guide bushing 132; this arrangement serves both to limit how far the depth cannula 134 can be axially extended or retracted relative to the guide bushing 132, and also prevents the depth cannula 134 from rotating about the measurement axis MX. However, it will be appreciated that the measurement module 128 could be configured to limit or prevent movement of the depth cannula 134 in other ways without departing from the scope of the present disclosure.

The depth cannula 134 further comprises a plurality of rack teeth 144 disposed linearly along at least a partial length of the depth cannula 134 which are disposed in meshed engagement with the gear 146 arranged adjacent a distal end of the guide bushing 132. As shown in FIG. 6, the window 142 of the guide bushing 132 is arranged adjacent to the gear 146 to facilitate the meshed engagement between the rack teeth 144 and the gear 146 such that rotation of the gear 146 and movement of the depth cannula 134 are directly proportional. The displacement sensor assembly 136 is responsive to rotation of the gear 146 resulting from axial movement of the depth cannula 134, and may be realized with a potentiometer, a rotary encoder, and the like, in order to generate electrical signals representing changes in the position of the depth cannula 134 along the measurement axis MX. Thus, it will be appreciated that the displacement sensor assembly 136 is able to provide the surgical handpiece system 60 with enhanced functionality. By way of example, in some configurations, the displacement sensor assembly 136 may be disposed in communication with the controller 78, which may be configured to interrupt or adjust how the motor 84 is driven based on movement of the depth cannula 134, such as to slow rotation of the drill bit 66 at a specific drilling depth into tissue. The displacement sensor assembly 136 may also be disposed in communication with a display 148, such as a display screen, one or more light-emitting diodes (LEDs), and the like, to provide the surgeon with information relating to movement of the depth cannula 134, such as to display a real-time drilling depth, a recorded historical maximum drilling depth, and the like. Other configurations are contemplated. This same information may also be communicated to the user with a speaker, so as to provide audio indications of the real-time drilling depth, a recorded historical maximum drilling depth, and the like. The disclosure of International Patent Publ. No. WO/2017/040783 entitled "Powered Surgical Drill With Integral Depth Gauge That Includes A Probe That Slides Over A Drill Bit" and filed on Sep. 1, 2016, is hereby incorporated by reference in its entirety.

Those having ordinary skill in the art will appreciate that the various components of the measurement module 128 could be arranged in a number of different ways. Moreover, while the illustrated measurement module 128 attaches to the illustrated surgical handpiece assembly 62 and is compatible with the drill bit 66 of the present disclosure, it is contemplated that the surgical handpiece assembly 62 could omit the measurement module 128 in some configurations, such as to employ different types of modules, housings, covers, and the like.

Figure 12:
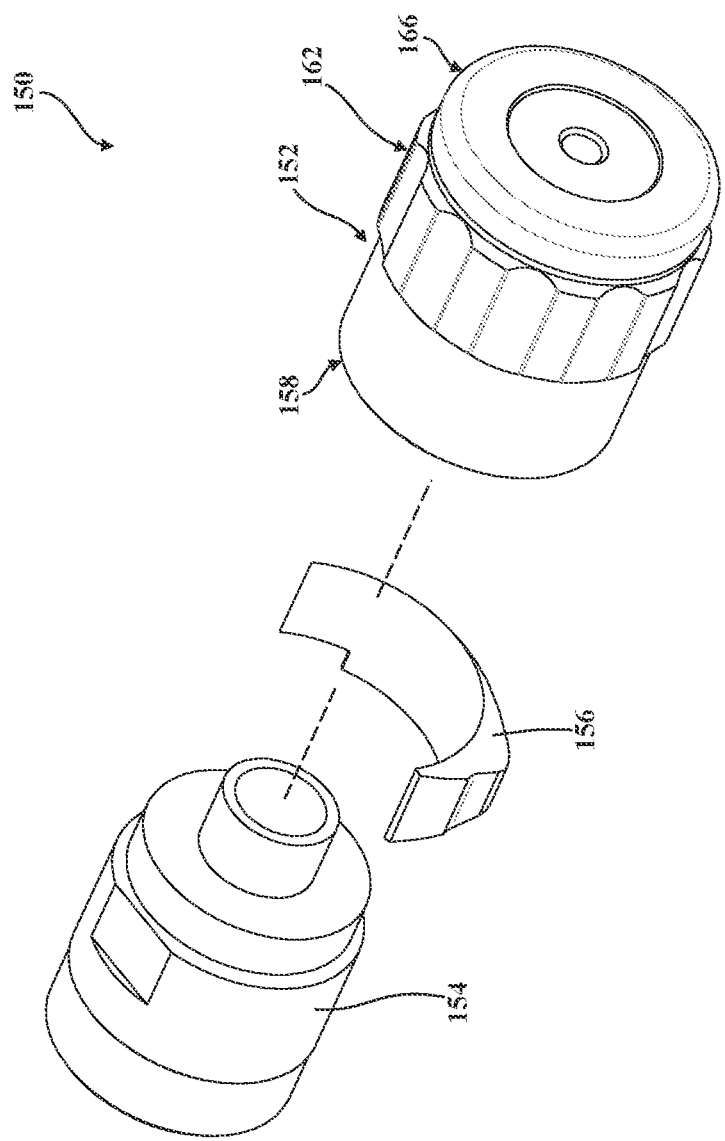
FIG. 12 is a partially-exploded view of the release assembly of FIGS. 1-7I, shown having a release subassembly spaced from a keeper body and a housing adapter.
Figure 13:
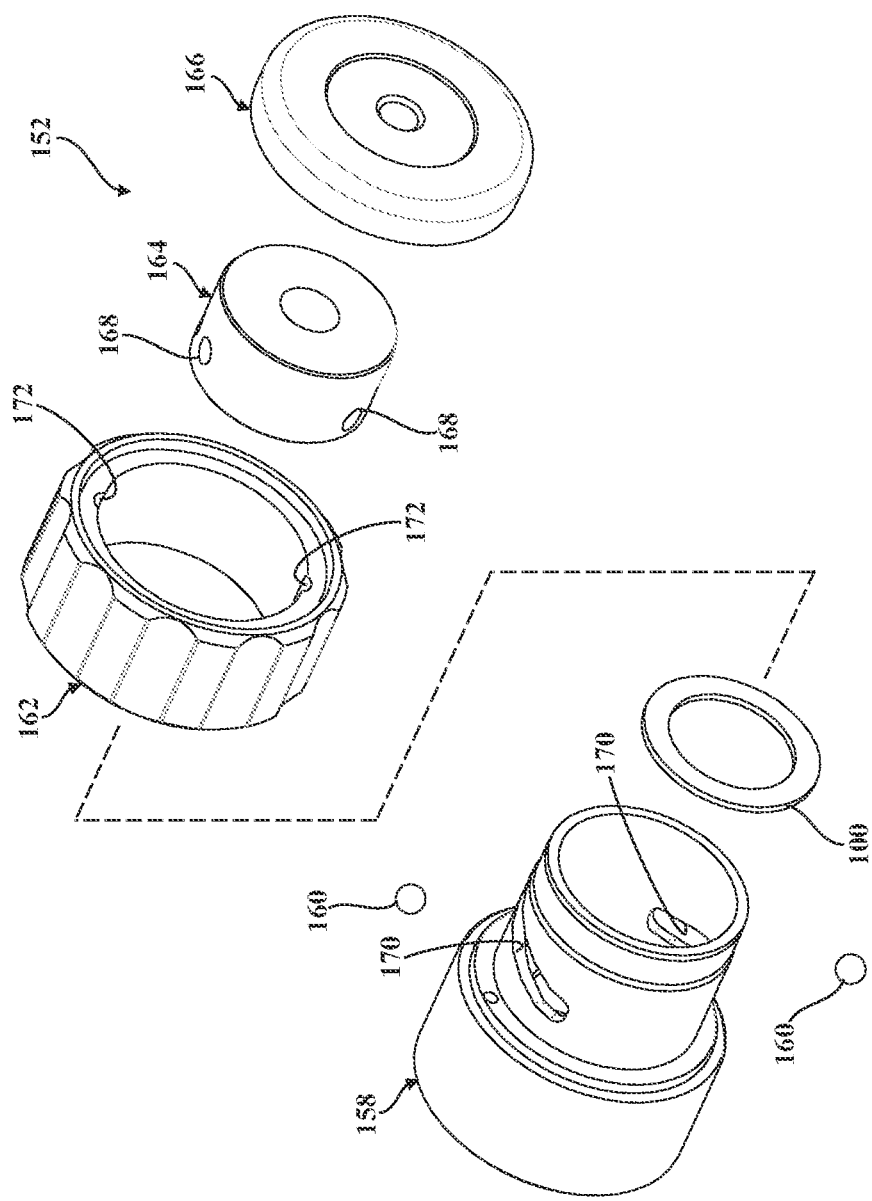
FIG. 13 is an exploded perspective view of the release subassembly of FIG. 12.
Figure 14:
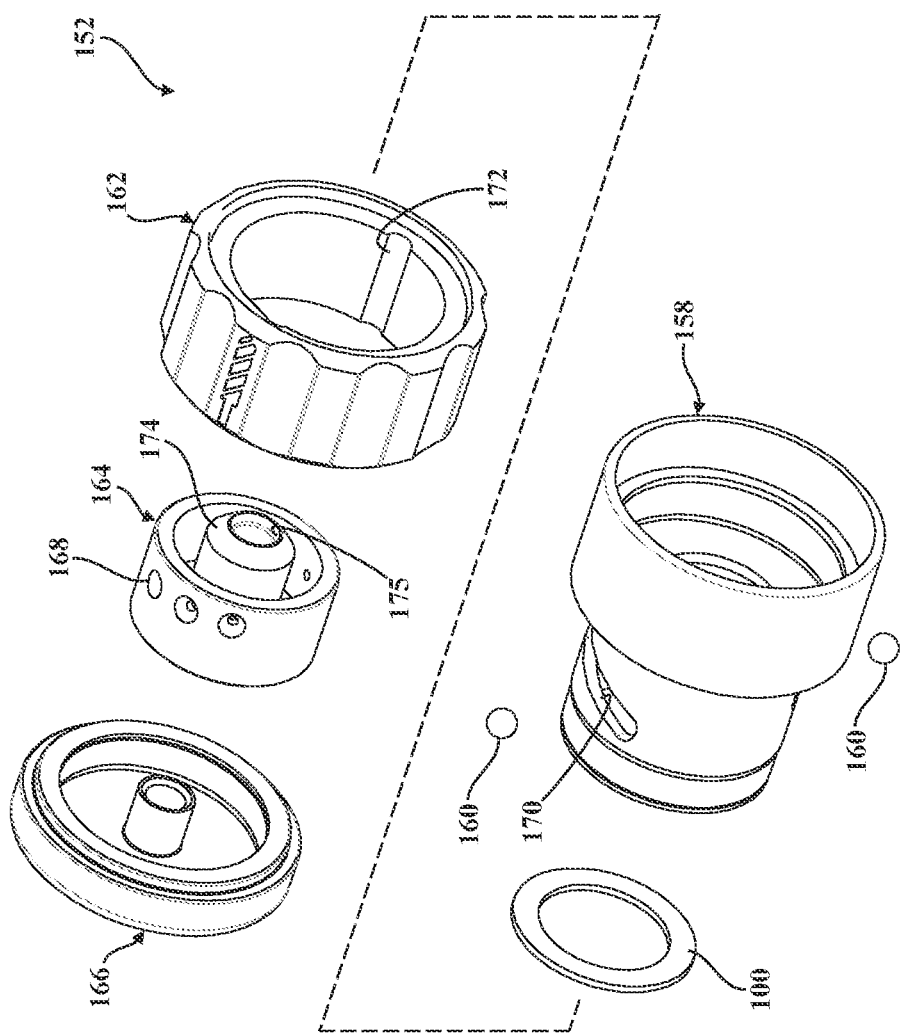
FIG. 14 is another exploded perspective view of the release subassembly of FIGS. 12-13.

Referring now to FIGS. 1-3 and 12-14, the illustrated configuration of the surgical handpiece assembly 62 further comprises a release assembly, generally indicated at 150, configured to facilitate removal of the drill bit 66 as described in greater detail below in connection with FIGS. 7F-7I. As shown in FIG. 12, the release assembly 150 generally comprises a release subassembly 152, a keeper body 154, and a housing adapter 156. The keeper body 154 and the housing adapter 156 are respectively configured to secure the release subassembly 152 to the actuator assembly 82 and the handpiece housing assembly 74, and could be realized with a number of different configurations or could be integrated into other parts of the surgical handpiece assembly 62 in some configurations. As shown in FIGS. 13-14, the release subassembly 152 of the release assembly 150 comprises a release body 158, a washer 100, a pair of guide elements 160, a collar 162, a release member 164, and a cap 166. The guide elements 160 are supported within pockets 168 formed in the release member 164, ride along respective helical slots 170 formed in the release body 158, and move along respective collar channels 172 formed in the collar 162. The guide elements 160 in the illustrated configuration are spherical. This arrangement allows the release member 164 to translate distally and proximally along the axis AX in response to rotation of the collar 162 (see FIGS. 7F-7I). As is described in greater detail below, the release member 164 comprises an actuating element 174 which defines a release surface 175 that is configured to engage the insertion portion 72 of the drill bit 66 in response to rotation of the collar 162. Rotation of the collar 162 causes the release member 164 to translate distally along the axis AX, to facilitate removing the drill bit 66 from the drive cannula 114 of the surgical handpiece assembly 62. In the illustrated configuration, the release surface 175 is an annular surface that tapers away from the axis AX proximally to distally. A biasing element such as a compression spring (not shown) may be interposed between the release body 158 and the release member 164, along with one or more washers 100, to urge the release member 164 toward the cap 166. Other suitable biasing elements and/or fasteners could be employed to facilitate urging the release member 164 toward the cap and/or axially retaining the release member 164 relative to the release subassembly.

As noted above, the drill bit 66 of the present disclosure generally extends along the axis AX between the cutting tip portion 70 and the insertion portion 72, and is configured for releasable attachment to the surgical handpiece assembly 62 described herein and illustrated throughout the drawings via engagement between the interface 124 of the drill bit 66 and the bore 122 of the proximal portion 116 of the drive cannula 114. The drive cannula 114, in turn, cooperates with the output hub 96 of the gearset 86 of the actuator assembly 82 to facilitate rotating the drill bit 66 about the axis AX. The drill bit 66, the drive cannula 114, and the output hub 96, as well as the cooperation therebetween, will each be described in greater detail below.

Referring now to FIGS. 2 and 20-24B, the drill bit 66 comprises a shank, generally indicated at 176, which extends along the axis AX between a proximal end 178 and a distal end 180 (shown in FIG. 2). The distal end 180 of the shank 176 is provided with flutes 182 which are helically disposed about the axis AX and extend to the tip of the drill bit 66 to promote tissue penetration (see FIG. 2). In the illustrated configuration, the drill bit 66 is also optionally provided with a bearing region 184 coupled to the shank 176 between the proximal end 178 and the distal end 180 (see FIG. 2). The bearing region 184 is sized so as to be received within and rotate relative to the depth cannula 134 of the measurement module 128 (see FIG. 4). Here, the bearing region 184 essentially defines a "stepped" outer region of the shank 176 that affords rotational support along the length of the drill bit 66, and has a larger diameter than adjacent distal and proximal regions of the shank 176 in the illustrated configuration. However, it will be appreciated that the bearing region 184 of the shank 176 of the drill bit 66 could be configured in other ways without departing from the scope of the present disclosure. Furthermore, while described as a drill bit 66 in the present disclosure, it is also contemplated that the drill bit 66 could have similar features and be configured as another suitable end effector, or rotary end-effector, such as a bur or reamer.

In the illustrated configuration, the drill bit 66 is formed as a single-piece component such that the distal end 180 of the shank 176 corresponds to or is otherwise disposed adjacent the cutting tip portion 70 of the drill bit 66.

However, it will be appreciated that the drill bit 66 could be manufactured in other ways, such as where the cutting tip portion 70 of the drill bit 66 is formed as a separate component from the shank 176 which is subsequently attached to the distal end 180 of the shank 176. Nevertheless, for the purposes of clarity and consistency, the cutting tip portion 70 introduced above corresponds with the distal end 180 of the shank 176 in the illustrated configuration described herein.

FIGS. 20-23 generally depict the insertion portion 72 of the drill bit 66 which, as noted above, is configured to facilitate releasable attachment to the surgical handpiece assembly 62. To this end, the interface 124 of the drill bit 66 is coupled to the shank 176 adjacent to but spaced distally from the proximal end 178 of the shank 176. As is described in greater detail below, the interface 124 of the shank 176 is configured to facilitate rotationally locking the drill bit 66 to the surgical handpiece assembly 62 so that the surgical handpiece assembly 62 can rotate the drill bit 66 upon attachment. In order to axially lock the drill bit 66 to the surgical handpiece assembly 62, the drill bit 66 further comprises a stop 186 and one or more resilient arms, generally indicated at 188. The stop 186 is coupled to the shank 176 adjacent to and spaced distally from the interface 124, and defines a stop surface 190 which has a tapered, generally frustoconical profile. As shown in FIGS. 7F and 17C, the stop surface 190 is shaped and arranged to abut a correspondingly-shaped, tapered seat surface 192 of the proximal portion 116 of the drive cannula 114 to limit how far the drill bit 66 can be advanced axially into the surgical handpiece assembly 62. The seat surface 192 may also be a transition surface tapering toward the axis AX distally to proximally to assist in guidance of the drill bit 66 through the bore 122 of the drive cannula 114. However, it will be appreciated that the drill bit 66 of the present disclosure could be configured in other ways sufficient to limit how far the drill bit 66 can be axially advanced into the surgical handpiece assembly 62. As is described in greater detail below, the resilient arm 188 is configured to axially retain the drill bit 66 to the drive cannula 114.

With reference to FIGS. 22-23, the interface 124 of the drill bit 66 extends along the axis AX between a distal interface end 194 and a proximal interface end 196. For the purposes of clarity and consistency, the distal interface end 194 and the proximal interface end 196 are defined herein as discrete locations along the length of the drill bit 66 between which the interface 124 has a generally consistent cross-sectional profile. However, it is contemplated that the distal interface end 194 and the proximal interface end 196 could be defined in other ways in some configurations. By way of illustrative example, it is conceivable that the interface 124 could comprise multiple discrete "interface regions" each having the same or different cross-sectional profiles which are delineated and spaced axially from each other along the shank 176, such as with cylindrical portions of the shank 176 extending therebetween. Other configurations are contemplated.

In the configuration of the drill bit 66 illustrated in FIGS. 22-23, a transition region 198 extends from the proximal interface end 196 to the proximal end 178 of the shank 176. Here, the transition region 198 effectively chamfers or "rounds-off" a portion of the interface 124 adjacent to the proximal end 178 of the shank 176 with a generally frustoconical profile to define the proximal interface end 196. For the purposes of clarity and consistency, the proximal end 178 of the shank 176 illustrated herein is defined by the reduced diameter portion of the transition region 198 from which the resilient arms 188 extend. Put differently, the resilient arms 188 extend from the proximal end 178 of the shank 176 to respective arm ends 200, and the proximal end 178 of the shank 176 is distal from the arm ends 200. The resilient arms 188 will be described in greater detail below.

As noted above, the illustrated configuration of the bore 122 of the proximal portion 116 of the drive cannula 114 of the surgical handpiece assembly 62 has a generally rounded, hexagonal profile defined by six bore flats 122F and six bore corners 122C (see FIG. 18A), and the interface 124 of the drill bit 66 is configured to be received within the bore 122 to promote concurrent rotation between the drill bit 66 and the drive cannula 114 about the axis AX. To this end, the interface 124 of the drill bit 66 comprises at least one outermost drive portion 202 which is spaced from the axis AX at a first interface distance 204 (depicted schematically in FIGS. 29-33). In some configurations, the outermost drive portion 202 of the interface 124 is defined by an outer drive surface 206 facing away from the axis AX. Regardless, for the purposes of clarity and consistency, the first interface distance 204 and the outermost drive portion 202 are defined by whichever edge, apex, point, or surface of the interface 124 is spaced furthest from the axis AX. In some configurations, the interface 124 comprises a first outermost drive portion spaced from the axis AX at a first interface distance and a second outermost drive portion spaced from the axis AX at a second interface distance to define a maximum drive dimension 208 of the interface 124 (depicted schematically in FIGS. 29-33). In these configurations, the maximum drive dimension 208 is the "widest" portion of the interface 124. The first and second interface distances may comprise a common distance at which each of the first and second outermost drive portions is spaced from the axis AX, such that the arrangement of the first and second outermost drive portions relative to the axis AX is symmetrical. However, in other configurations, the first and second interface distances may not be equal to one another, such that the arrangement of the first and second outermost drive portions may be asymmetrical relative to the axis AX.

In some configurations, the interface 124 comprises at least one outer non-drive portion 210 which is spaced from the axis AX at a third interface distance 212 (depicted schematically in FIGS. 29-33). Further still, in some configurations, the outer non-drive portion 210 of the interface 124 is defined by an outer non-drive surface 214 which, in some configurations, may be defined as a planar interface surface. Regardless, for the purposes of clarity and consistency, the third interface distance 212 and the outer non-drive portion 210 are defined by whichever edge, apex, point, or surface of the interface 124 is spaced closest to the axis AX. In some configurations, the interface 124 comprises a first outer non-drive portion spaced from the axis AX at a third interface distance 212 and a second outer non-drive portion spaced from the axis AX at a fourth interface distance 212 to define a minimum interface dimension 216 of the interface 124 (depicted schematically in FIGS. 29-33). In these configurations, the minimum interface dimension 216 is the "narrowest" portion of the interface 124. The third and fourth interface distances may comprise a common distance at which each of the first and second outer non-drive portions is spaced from the axis AX, such that the arrangement of the first and second outer non-drive portions relative to the axis AX is symmetrical. However, in other configurations, the third and fourth interface distances may not be equal to one another, such that the arrangement of the first and second outer non-drive portions may be asymmetrical relative to the axis AX. Further still, two outer non-drive portions 210 are radially spaced about the axis AX from two outermost drive portions 202. However, as will be appreciated from the subsequent description below, the interface 124 could be configured in other ways sufficient to be received within and rotate concurrently with the bore 122 of the proximal portion 116 drive cannula 114.

Figure 29:
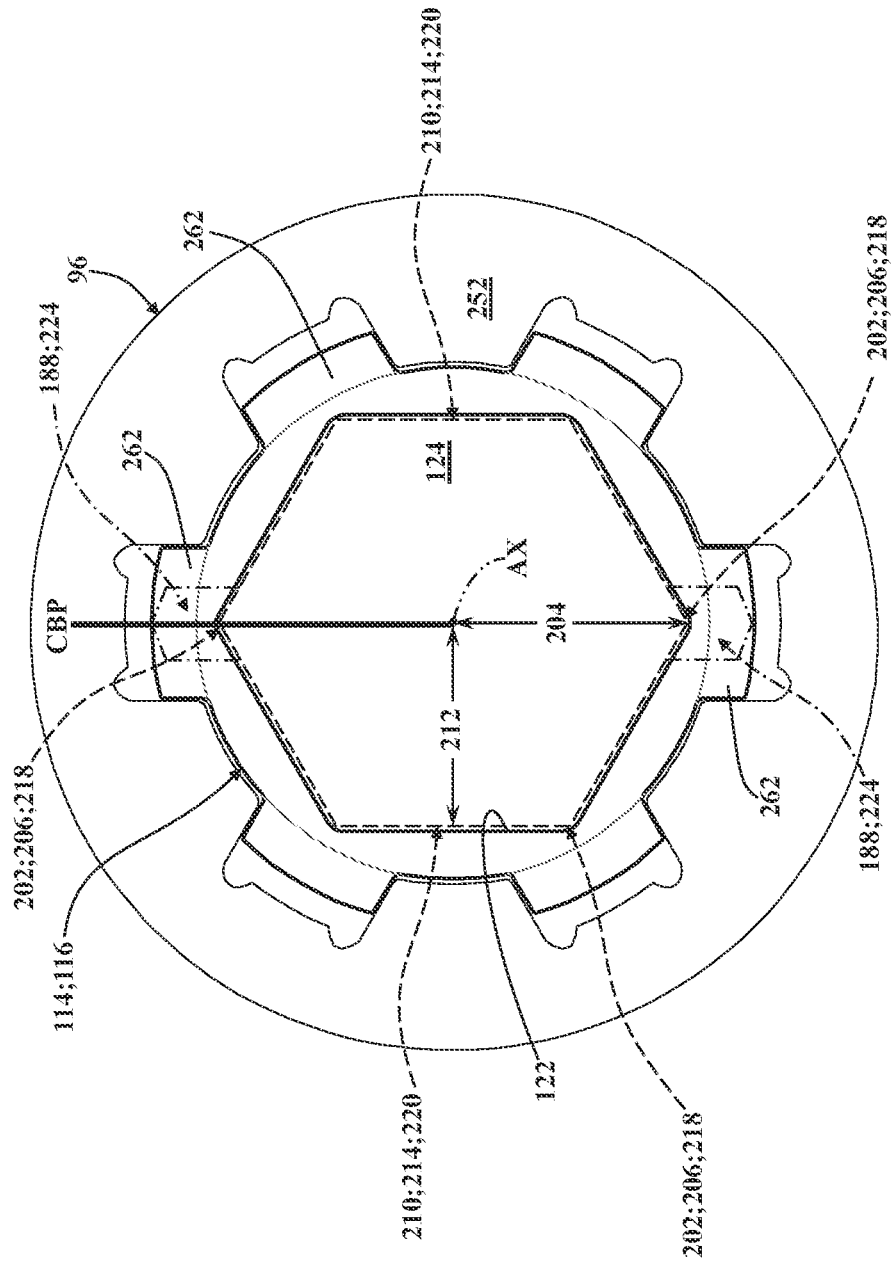
FIG. 29 is a front-side schematic view representing the proximal portion of the drive cannula, the output hub, and the drill bit arranged as depicted in FIG. 15C, the schematic view showing the arrangement of the lock surfaces of the proximal portion of the drive cannula delineated from one another by the splined engagement between the proximal portion of the drive cannula and the output hub, the schematic view further showing the profile of the interface of the drill bit with dash-dash lines disposed within the bore of the proximal portion of the drive cannula, and the schematic view still further showing the arrangement of the resilient arms with dash-dot-dash lines to illustrate abutment with the lock surfaces of the proximal portion of the drive cannula as well as radial alignment of the retention surfaces of the resilient arms with respect to the profile of the interface.
Figure 30:
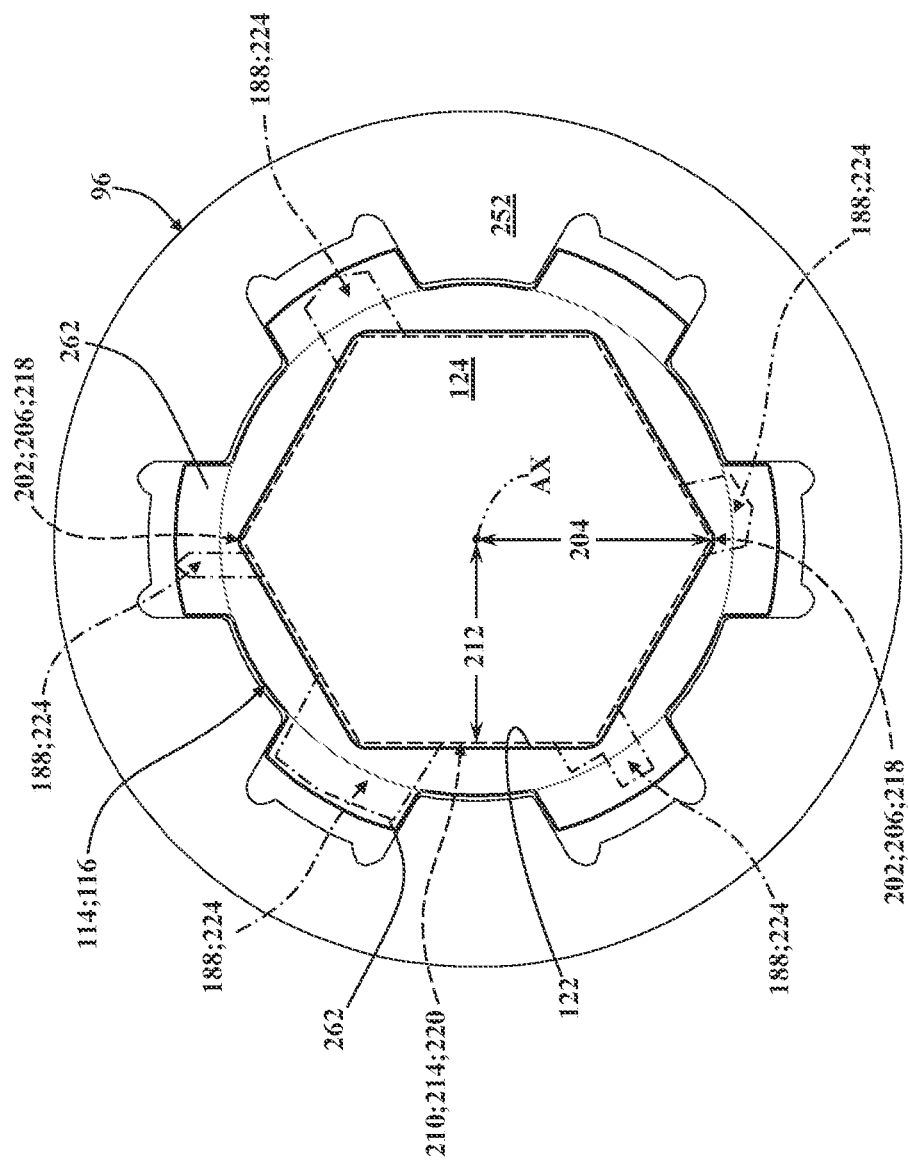
FIG. 30 is another front-side schematic view representing the proximal portion of the drive cannula and the output hub of FIG. 29 with a configuration of a drill bit having resilient arms shown sized, shaped, and arranged in abutment with the lock surfaces of the proximal portion of the drive cannula.

By way of illustrative example of the features of the interface 124 introduced above, the interface 124 of the configuration of the drill bit 66 depicted in FIGS. 18C and 20-24B, and depicted schematically in FIGS. 29 and 30, has a generally rounded hexagonal profile comprising a total of six outermost drive portions 202 and a total of six outer non-drive portions 210. Here, the six outermost drive portions 202 are each respectively defined by an outer drive surface 206 which is rounded to define a corner 218. Thus, in this configuration, the maximum drive dimension 208 is defined between the apexes of two diametrically opposed corners 218. Furthermore, in this configuration, the six outer non-drive portions 210 are each respectively defined by an outer non-drive surface 214 which is substantially flat to define a planar surface 220. Thus, in this configuration, the minimum interface dimension 216 is defined between the midpoints of two diametrically opposed planar surfaces 220.

As is described in detail below in connection with FIGS. 29-33, the interface 124 of the drill bit 66 of the present disclosure could have a number of different cross-sectional profiles or configurations sufficient to be received within and rotate concurrently with the bore 122. Thus, while the illustrated configurations of the interface 124 depicted in FIGS. 2, 4-5, 7C-7I, 15B, 17C, 18B-18C, and 20-30 have a generally rounded hexagonal profile which is complementary to the profile of the bore 122 as described above, other configurations are contemplated by the present disclosure, including without limitation: other generally polygonal profiles such as a rectangle (see FIG. 31) or a star (see FIG. 32), irregular polygons, and/or other profiles and/or shapes which can be removably received within and rotate concurrently with the hexagonal bore 122 of the proximal portion 116 of the drive cannula 114 (see FIG. 33).

As noted above, the drill bit 66 of the present disclosure comprises one or more resilient arms 188 which extend from the proximal end 178 of the shank 176 to respective arm ends 200. The resilient arms 188 of the drill bit 66 are provided to, among other things, facilitate axially retaining the drill bit 66 to the surgical handpiece assembly 62 when the stop surface 190 of the drill bit 66 abuts the seat surface 192 of the proximal portion 116 of the drive cannula 114. As will be appreciated from the subsequent description below, the resilient arms 188 could be formed integrally with the shank 176 and could be machined, bent, and the like, or the resilient arms 188 could be formed separately from and subsequently attached to the shank 176, such as via welding, brazing, adhering, bonding, or any suitable process sufficient to operatively attach the resilient arms 188 to the shank 176.

With reference to FIGS. 20-23, the illustrated configuration of the insertion portion 72 of the drill bit 66 comprises resilient arms 188 which each have an outer arm surface 222 facing away from the axis AX, and a retention surface 224 facing toward the distal end 180 of the shank 176 (see FIG. 23). As is described in greater detail below in connection with FIGS. 29-33, the retention surface 224 of the resilient arm 188 is arranged so as to be radially aligned about the axis AX with one of the outermost drive portions 202 of the interface 124. Furthermore, as is described in greater detail below in connection with FIGS. 7A-7I, 15A-19C, and 29-33, the resilient arm 188 is configured so as to be movable relative to the axis AX between a first position P1 (see FIGS. 7B and 22) and a second position P2 (see FIGS. 7D-7E). In the first position P1, the outer arm surface 222 is spaced from the axis AX at a first arm distance 226 which is greater than the first interface distance 204. In the second position P2, the outer arm surface 222 is spaced from the axis AX at a second arm distance 228 which is less than the first arm distance 226 and, in some configurations, is less than or equal to the first interface distance 204. Put differently, the outer arm surface 222 of the resilient arm 188 is spaced further from the axis AX than any portion of the interface 124, and the resilient arm 188 is deflectable relative to the axis AX from the first position P1 toward the second position P2, and is resiliently biased toward the first position P1. As is described in greater detail below, this configuration helps facilitate releasable axial retention of the drill bit 66 to the surgical handpiece assembly 62 and, in some configurations, also affords self-aligning functionality to the drill bit 66 so as to index the interface 124 to the bore 122 by promoting rotation of the drill bit 66 about the axis AX during attachment to the surgical handpiece assembly 62 (see FIGS. 24A-24B, described in greater detail below).

Continuing the previous example above where the interface 124 comprises first and second outermost drive portions, the retention surface may be radially aligned with the first outermost drive portion. The outer arm surface 222 of the resilient arm 188 in the first position P1 may be spaced from the axis AX at the first arm distance, which may be greater than the first interface distance at which the first outermost drive portion is spaced from the axis AX. Furthermore, the outer arm surface 222 of the resilient arm 188 in the second position P2 may be spaced from the axis AX at the second arm distance, which may be less than the first arm distance and less than or equal to the first interface distance.

In another configuration, where the interface 124 comprises first and second outermost drive portions, the retention surface may not be radially aligned with the first outermost drive portion. Rather, the retention surface may be radially aligned with the second outermost drive portion. The outer arm surface 222 of the resilient arm 188 in the first position P1 may be spaced from the axis AX at a first arm distance, which in this configuration is greater than the second interface distance at which the second outermost drive portion is spaced from the axis AX. Furthermore, the outer arm surface 222 of the resilient arm 188 in the second position P2 may be spaced from the axis AX at a second arm distance, which is less than the first arm distance and less than or equal to the second interface distance.

As is best shown in FIG. 23, the outer arm surface 222 in the illustrated configuration is generally rectangular in profile, when viewed from the top, and is arranged between the arm end 200 and the retention surface 224. However, it will be appreciated that the outer arm surface 222 could be realized with other configurations, profiles, arrangements, and the like. For the purposes of clarity and consistency, the outer arm surface 222 is defined by whichever surface, face, edge, apex, or point of the resilient arm 188 that is spaced furthest from the axis AX when the resilient arm 188 is in the first position P1.

With continued reference to FIGS. 20-23, the resilient arm 188 further comprises a ramp surface 230 which extends distally from the arm end 200 and merges with the outer arm surface 222. The ramp surface 230 is shaped and arranged so as to deflect the resilient arm 188 relative to the axis AX in response to engagement, contact, abutment, and the like. By way of example, in the illustrated configuration, the ramp surface 230 is shaped and arranged to engage against the tapered seat surface 192 of the proximal portion 116 of the drive cannula 114 (see FIG. 7C) in order to move the resilient arm 188 from the first position P1 to the second position P2 as the drill bit 66 is attached to the surgical handpiece assembly 62 (sequentially compare FIGS. 7B-7D). Similarly, in the illustrated configuration, the ramp surface 230 is shaped and arranged to engage the actuating element 174 of the release assembly 150 (see FIGS. 7G-7H) as the release member 164 translates distally along the axis AX in order to move the resilient arm 188 toward the second position P2 to facilitate removing the drill bit 66 from the surgical handpiece assembly 62 (sequentially compare FIGS. 7F-7I).

Referring now to FIGS. 20-24B, the illustrated configuration of the resilient arm 188 comprises an arm body 232 and a finger portion, generally indicated at 234. In one exemplary configuration, the arm body 232 has a generally linear profile with a generally arcuate portion which merges with the proximal end 178 of the shank 176. As best shown in FIG. 22, the arm body 232 extends away from the proximal end 178 of the shank 176. In the illustrated configuration, this configuration places the retention surface 224 at an arm position angle 236 (see FIG. 22) defined relative to the axis AX, which is generally oblique when the resilient arm 188 is in the first position P1 and which is generally perpendicular when the resilient arm 188 is in the second position P2. However, as will be appreciated from the subsequent description of the interaction between the insertion portion 72, the proximal portion 116 of the drive cannula 114, and the output hub 96, the retention surface 224 could be arranged or configured in other ways, such as to be at a non-perpendicular angle relative to the axis AX when the resilient arm 188 is in the second position P2. Other configurations are contemplated. Furthermore, while the arm body 232 extends away from the axis AX toward the arm end 200 in the illustrated configuration, it is conceivable that the arm body 232 could extend generally parallel with the axis AX in alternate configurations of the drill bit 66. In other configurations, the retention surface 224 can be arranged or configured relative to the resilient arm 188, such that the retention surface 224 is arranged at an 80-degree angle relative to the resilient arm 188. However, the retention surface can instead by arranged at any suitable angle above or below 80 degrees relative to the resilient arm.

The finger portion 234 of the resilient arm 188 is formed at the arm end 200 and, in the illustrated configurations, provides or otherwise defines the outer arm surface 222, the retention surface 224, and the ramp surface 230. As shown in FIG. 22, the finger portion 234 protrudes generally away from the axis AX to the outer arm surface 222. As shown in FIG. 23, the finger portion 234 defines a pair of outer finger surfaces 238 which are spaced at a finger width 240 from one another and are generally perpendicular to the retention surface 224. However, it will be appreciated that the finger portions 234 could be configured in a number of different ways, such as with a triangular profile, a rectangular profile, a rounded profile, a pentagonal profile, or other suitable profiles.

In the illustrated configuration, the finger portion 234 further comprises an aligning element, generally indicated at 242, arranged adjacent to the arm end 200. The aligning element 242 may be positioned at different locations on the resilient arm 188 besides the finger portion 234. Furthermore, fewer than all of the resilient arms 188 may include the aligning element 242. As will be appreciated from the subsequent description below, the aligning element 242 may comprise at least a portion of the outer arm surface 222, at least a portion of the ramp surface 230, and/or one or more planar arm surfaces 244 arranged adjacent to the outer arm surface 222 and to the ramp surface 230 (see FIGS. 20-23. Here, the planar arm surfaces 244 are arranged so as to be generally coplanar with respective planar surfaces 220 of outer non-drive surfaces 214 of the interface 124 when the resilient arm 188 is in the second position P2 (see FIG. 24B). In some configurations, the aligning element 242 may comprise a single planar arm surface 244. Moreover, while the illustrated configuration of the aligning element 242 employs a generally planar outer arm surface 222 arranged between two planar arm surfaces 244, it will be appreciated that other configurations are contemplated. By way of non-limiting example, the outer arm surface 222 could be realized as a discrete edge or point defined by a non-planar arm surface, formed such as with a wedge shape, where the discrete edge or point is arranged in radial alignment (e.g., co-linear with) one of the outermost drive portions 202 of the interface 124 when the resilient arm 188 is in the second position P2. In some configurations, the aligning element 242 is shaped so as to mimic, mirror, or otherwise complement the interface 124 when the resilient arm 188 is in the second position P2. Other configurations are contemplated, such as where the interface 124 is configured with a star-shaped profile with a plurality of drive lobes 245 spaced about the axis AX, such as the configuration illustrated in FIG. 32, the aligning element 242 may have a profile which at least partially replicates or otherwise complements one of the drive lobes 245 (e.g., a triangular profile).

Figure 24A:
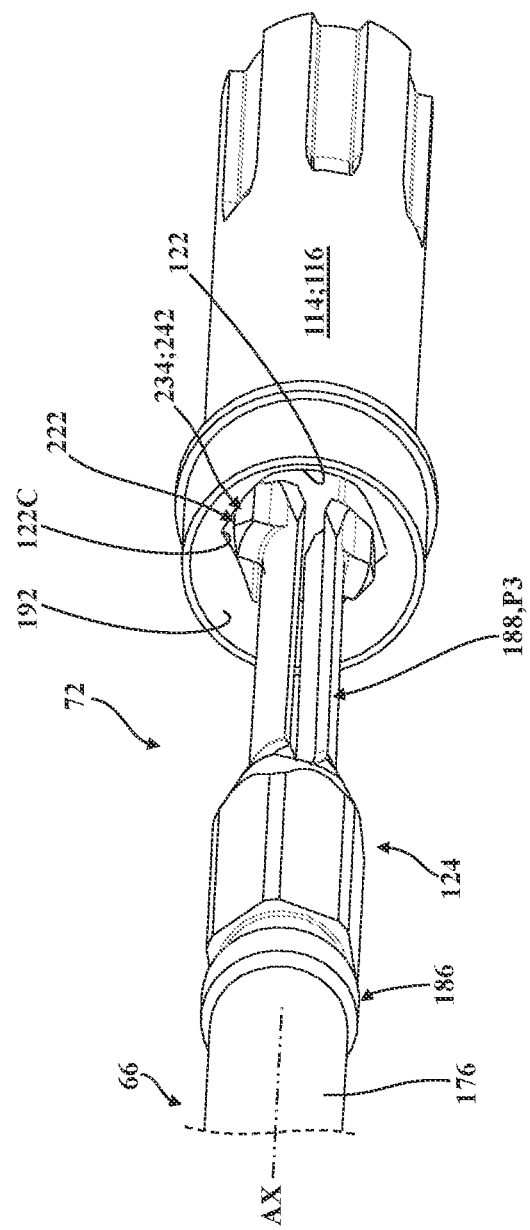
FIG. 24A is a partial perspective view of the drill bit of FIGS. 1-2, 4-5, 7B-7I, and 15B-15C and the proximal portion of the drive cannula of FIGS. 15A-15B, shown with the interface of the drill bit misaligned with the bore of the proximal portion of the drive cannula.
Figure 24B:
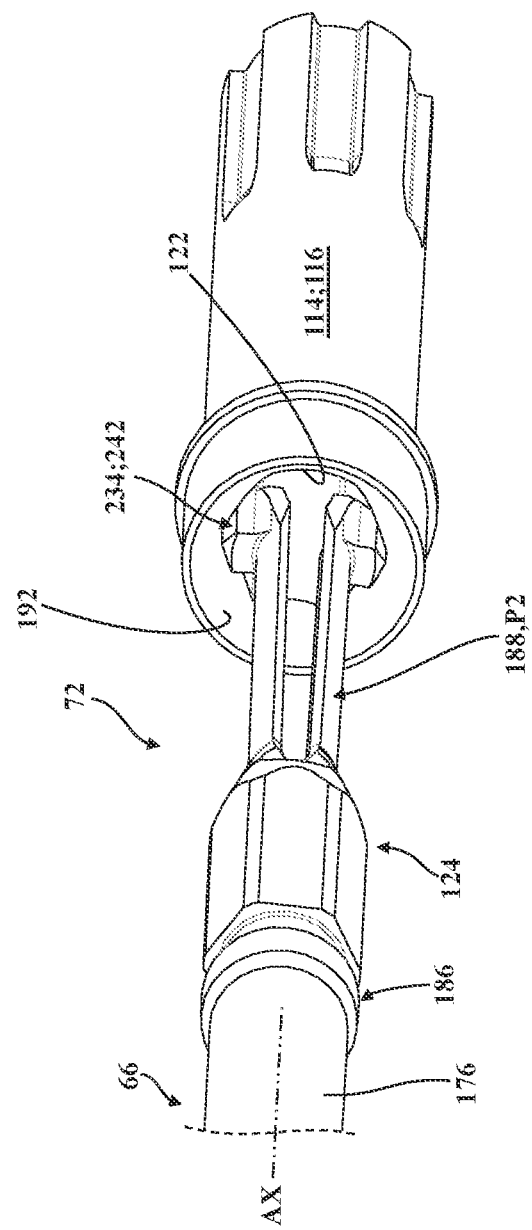
FIG. 24B is another partial perspective view of the drill bit and the proximal portion of the drive cannula of FIG. 24A, shown with the interface of the drill bit subsequently aligned with the bore of the proximal portion of the drive cannula.
Figure 25:
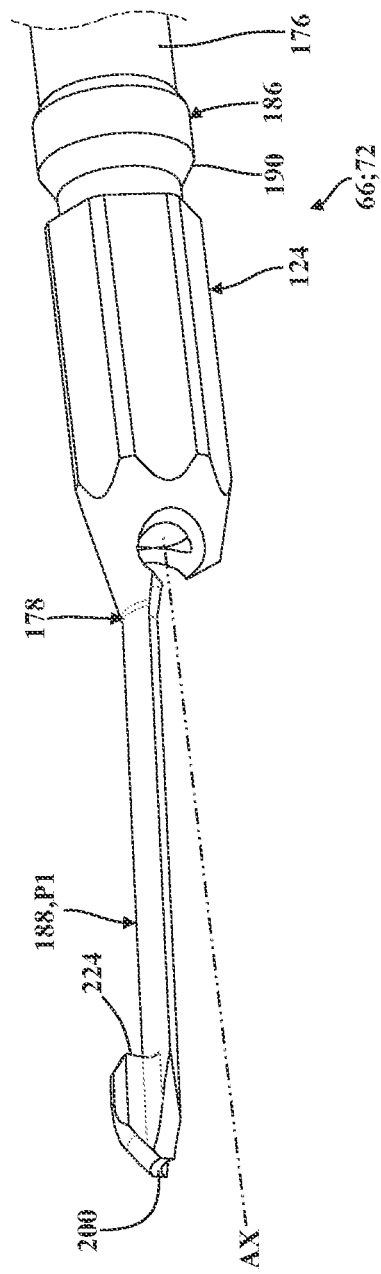
FIG. 25 is a partial perspective view of another drill bit configuration, shown having a single resilient arm.
Figure 26:
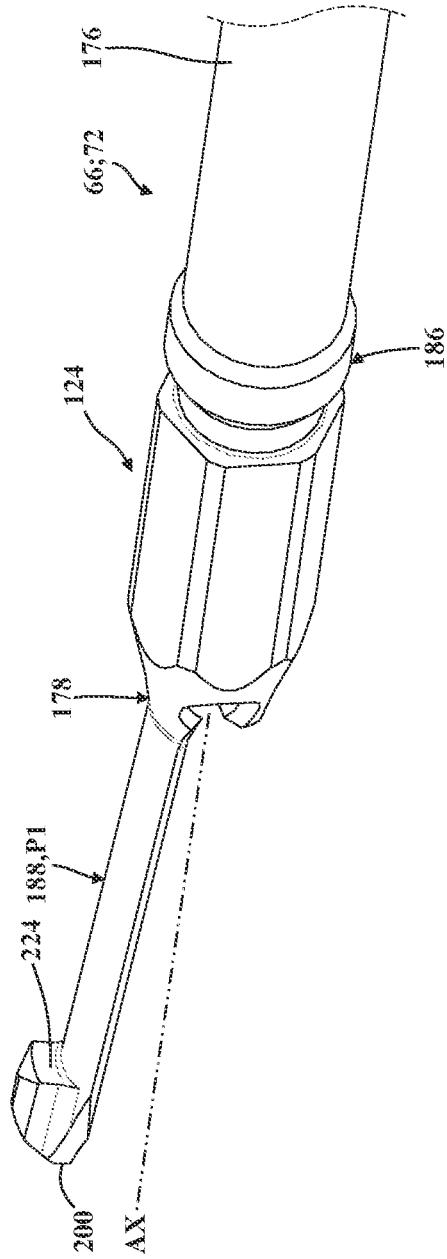
FIG. 26 is another partial perspective view of the configuration of the drill bit illustrated in FIG. 25.
Figure 27:
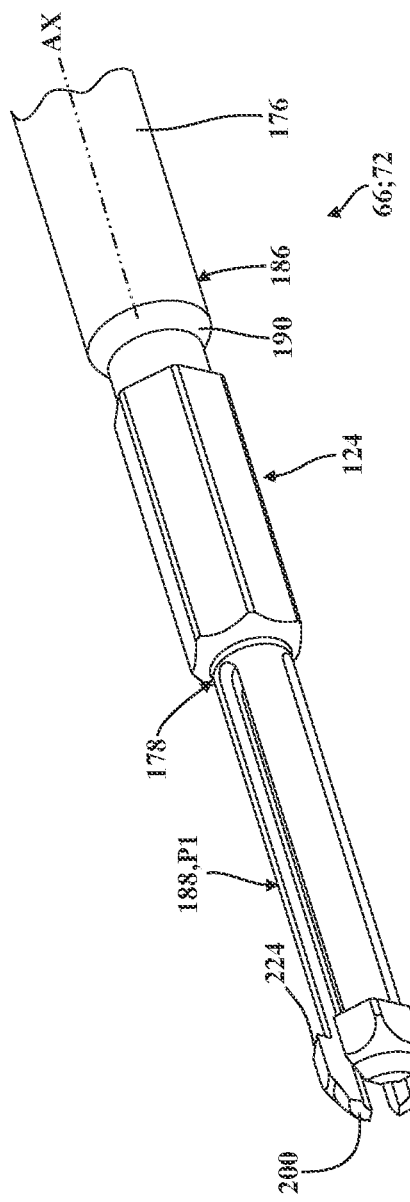
FIG. 27 is a partial perspective view of another drill bit configuration, shown having three resilient arms.
Figure 28:
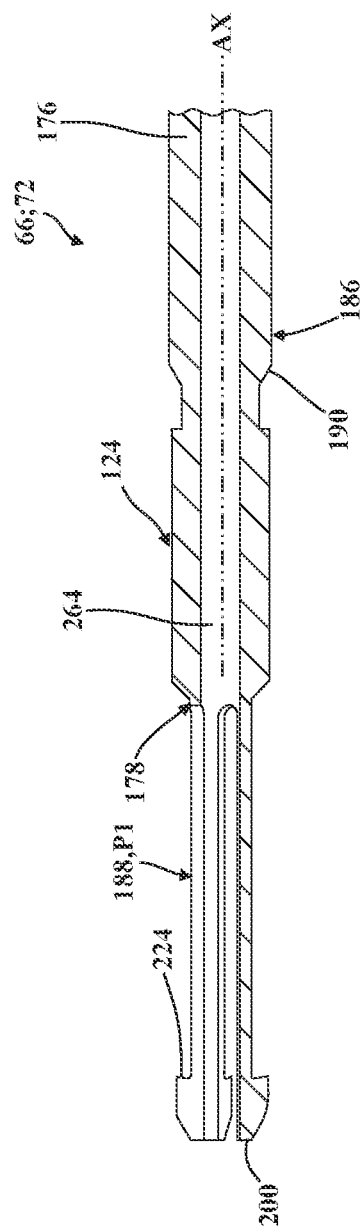
FIG. 28 is a partial longitudinal sectional view of the configuration of the drill bit illustrated in FIG. 27, shown having a cannulated shank.

The aligning element 242 is employed to facilitate at least partial rotation of the drill bit 66 about the axis AX as the resilient arm 188 moves from the first position P1 to the second position P2 in response to force applied to the drill bit 66 along the axis AX during attachment to the surgical handpiece assembly 62. More specifically, as shown in FIGS. 24A-24B, as the resilient arm 188 moves toward the second position P2 in response to engagement with the tapered seat surface 192 of the proximal portion 116 of the drive cannula 114, one or more portions of the aligning element 242 are disposed in abutment with the tapered seat surface 192. Here, because potential energy is stored in the resilient arm 188 when deflected away from the first position P1, the abutment between the tapered seat surface 192 and one or more portions of the aligning element 242 promotes at least partial rotation of the drill bit 66 relative to the drive cannula 114 as the aligning element 242 is advanced from the tapered seat surface 192 of the proximal portion 116 of the drive cannula 114 into the bore 122 of the proximal portion 116 of the drive cannula 114. Thus, as the resilient arm 188 enters the bore 122, the drill bit 66 "self-aligns" with the bore 122 in that the rotation of the drill bit 66 about the axis AX is caused by the outer arm surface 222 being urged toward one of the bore corners 122C, and the planar arm surfaces 244 of the aligning element 242 are brought into respective engagement with the adjacent bore flats 122F (compare FIGS. 24A-24B).

In this configuration, the resilient arm 188 moves from the first position P1 at the first arm distance relative to the axis AX indirectly to the second position P2 (FIG. 24B) at the second arm distance relative to the axis AX. More specifically, the resilient arm 188 can move from the first position P1 directly to a third position P3 (FIG. 24A) at a third distance relative to the axis AX and from the third position P3 directly to the second position P2 (FIG. 24B). The first arm distance relative to the axis AX may be greater than the first interface distance 204 between the outermost drive portion 202 and the axis AX. The third arm distance relative to the axis AX may be less than each of the first arm distance and the first interface distance 204. The second arm distance relative to the axis AX may be greater than the third arm distance and less than or equal to the first interface distance 204.

When the resilient arm 188 is disposed in the third position, the outer arm surface 222 engages one of the bore flats 122F. Because the resilient arm 188 is urged away from the axis AX, movement of the outer arm surface 222 from the bore flat 122F to one of the bore corners 122C causes the resilient arm 188 to move from the third position (FIG. 24A) to the second position P2 (FIG. 24B) which, in turn, causes the drill bit to rotate into alignment with the bore. However, it is contemplated that, when the drill bit is already aligned with the bore prior to insertion into the bore and force is applied to the drill bit 66 along the axis AX, the resilient arm can move from the first position P1 directly to the second position P2.

Because the planar arm surfaces 244 are generally coplanar with planar surfaces 220 of the interface 124 when the resilient arm 188 is in the second position P2, the rotation described above "indexes" the interface 124 of the drill bit 66 with the bore 122 of the proximal portion 116 of the drive cannula 114 once the finger portion 234 is received within the bore 122 and the outer arm surface 222 is received in one of the bore corners 122C. While this configuration affords advantages in connection with attaching the end effector assembly 64 to the surgical handpiece assembly 62, by "self-aligning" the interface 124 of the drill bit 66 with the bore 122 of the proximal portion 116 of the drive cannula 114, it will be appreciated that the drill bit 66 could be configured in other ways, such as with different types of aligning elements 242 and/or finger portions 234. By way of non-limiting example, the drill bit 66 could omit the aligning element 242 and/or the finger portions 234 in some configurations. Other configurations are contemplated.

Figure 15A:
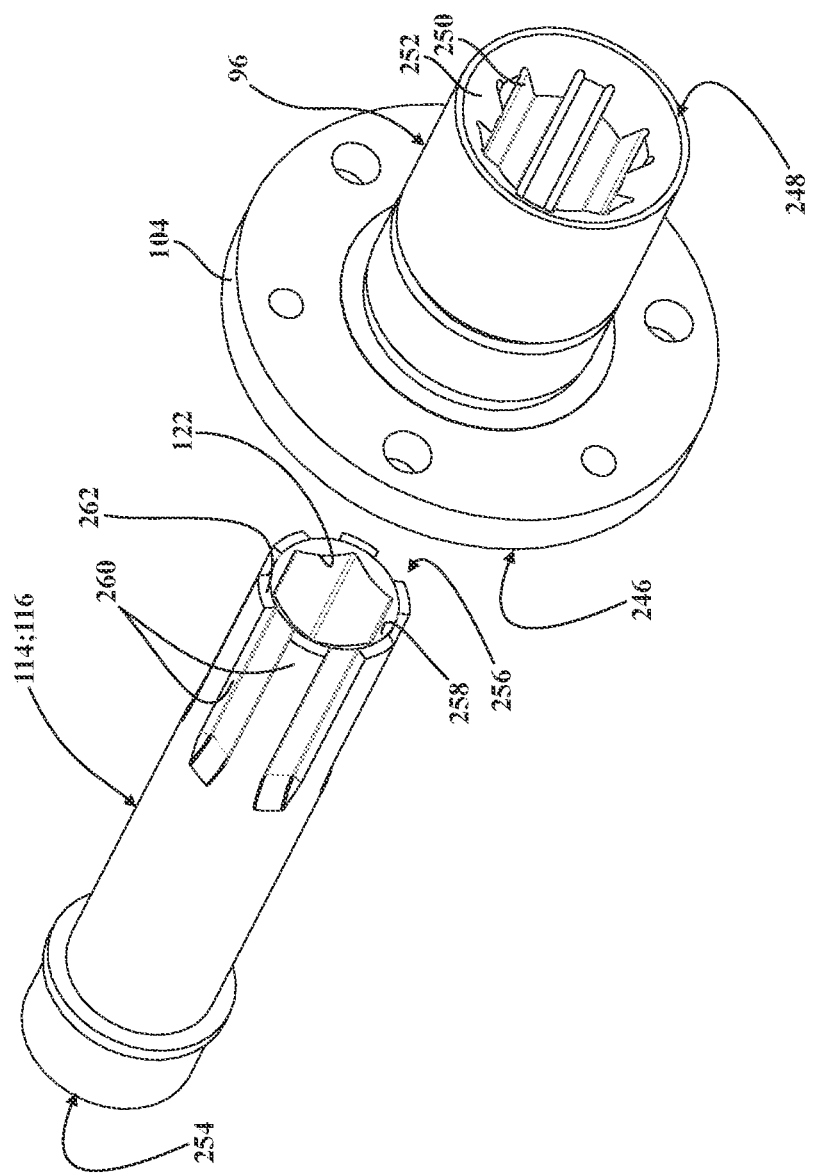
FIG. 15A is a perspective view showing the proximal portion of the drive cannula depicted in FIGS. 2-8 positioned adjacent to the output hub of the gearset depicted in FIGS. 3-7I and 9-11.

Referring now to FIGS. 15A-19C, as noted above, the proximal portion 116 of the drive cannula 114 cooperates with the output hub 96 of the actuator assembly 82 to facilitate rotating the drill bit 66 about the axis AX via splined engagement between the output hub 96 and the drive cannula 114. As is best shown in FIGS. 15A and 17A, the output hub 96 extends between a distal hub end 246 and a proximal hub end 248, and comprises one or more internal splines 250 which extend from the distal hub end 246, adjacent to the integrated carrier 104, toward but spaced from the proximal hub end 248. Here, the output hub 96 is provided with a lockout taper 252 which has a generally frustoconical profile extending internally to merge with the internal splines 250 such that the internal splines 250 terminate distal from the proximal hub end 248.

With continued reference to FIGS. 15A and 17A, the proximal portion 116 of the drive cannula 114 extends between a distal end 254 of the proximal portion 116 of the drive cannula 114 and a proximal end 256 of the proximal portion 116 of the drive cannula 114. Here, the tapered seat surface 192 is formed at the distal end 254 and tapers internally into the hexagonal bore 122, as noted above. The bore 122, in turn, extends along the axis AX toward the proximal end 256. In some configurations, the proximal portion 116 of the drive cannula 114 is provided with a release taper 258 which similarly tapers internally into the hexagonal bore 122 (see FIG. 17A) to help facilitate releasing the drill bit 66 from the surgical handpiece assembly. The splined engagement is facilitated by one or more grooves formed by the external surface of the proximal portion 116 of the drive cannula 114 or one or more projections extending from the external surface of the proximal portion 116 of the drive cannula 114. In one configuration shown in FIG. 15A, the one or more projections comprise external splines 260 which are formed extending from the proximal end 256 toward but spaced from the distal end 254. At the proximal end 256, the external splines 260 define lock surfaces 262 adjacent to the release taper 258. The lock surfaces 262 are arranged to abut the retention surface 224 of the resilient arm 188 to axially lock the drill bit 66 to the surgical handpiece assembly 62. The specific shape and arrangement of the internal splines and external splines can be adjusted to different arrangements or geometries so long as the lock surfaces are still present and arranged relative to the bore in a way that makes the lock surfaces accessible to the retention surfaces of the bit when the drive interface is received in the bore. In some configurations, the release taper 258 and lock surfaces 262 are integral and cooperate to form a retention surface of the proximal portion 116 of the drive cannula 114 that is configured to abut the retention surface 224 of the resilient arm 118. The retention surface of the proximal portion 116 of the drive cannula 114 tapers away from the axis AX proximally to distally to prevent accidental release of the drill bit 66 from the drive cannula 114.

Figure 15B:
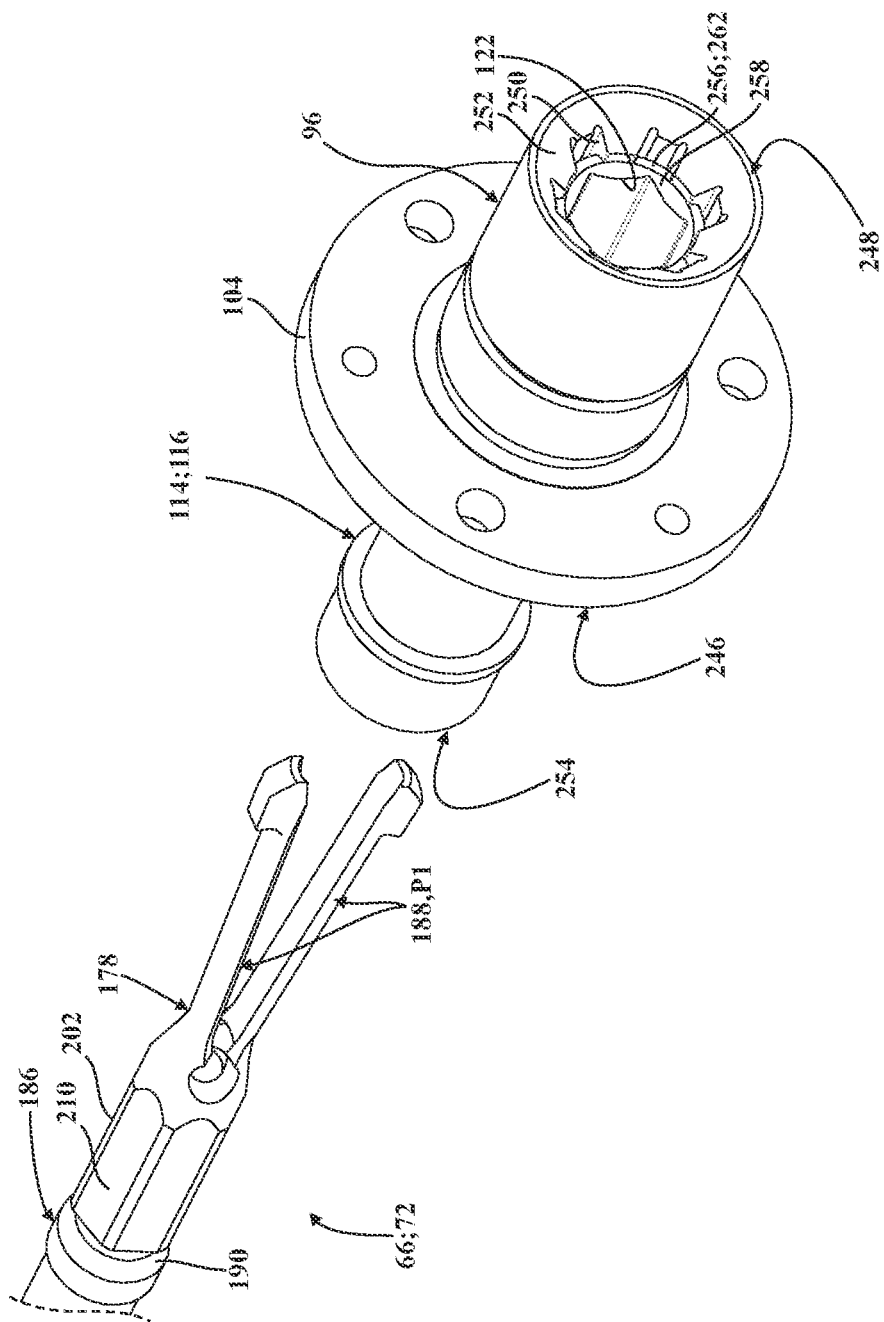
FIG. 15B is a perspective view of the proximal portion of the drive cannula and the output hub of FIG. 15A assembled for concurrent rotation via splined engagement, shown positioned adjacent to the resilient arms extending from the proximal end of the shank of the drill bit of FIGS. 1-2, 4-5, and 7B-7I.
Figure 15C:
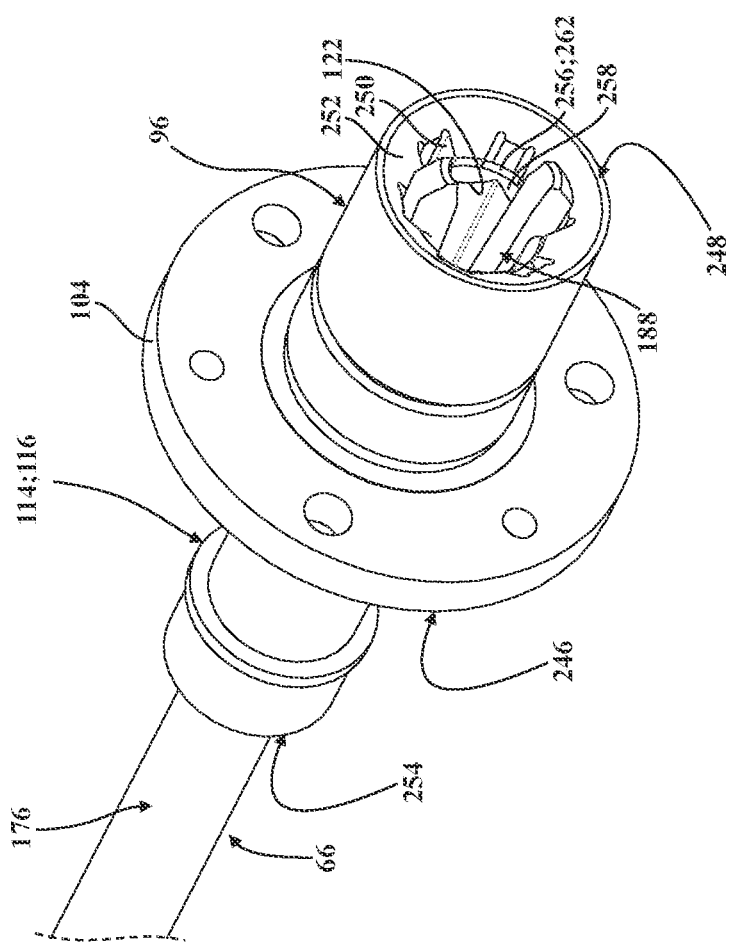
FIG. 15C is another perspective view of the proximal portion drive cannula, the output hub, and the drill bit of FIG. 15B, shown with the resilient arms of the drill bit disposed in abutment with the lock surfaces of the proximal portion of the drive cannula.

In one configuration shown best in FIGS. 15B, 17A, and 17C, the proximal end 256 is spaced distally from the proximal hub end 248 of the output hub 96. The lock surfaces 262 of the proximal portion 116 of the drive cannula 114 are likewise spaced distally from the proximal hub end 248 and, the lock surfaces 262 are also spaced distally from the lockout taper 252 of the output hub 96. This configuration ensures that axial retention of the drill bit 66 is effected via engagement between the retention surface 224 of the resilient arm 188 and one of the lock surfaces 262 of the proximal portion 116 of the drive cannula 114, and not with other portions of the proximal portion 116 of the drive cannula 114 or the output hub 96. Put differently, the lockout taper 252 of the output hub 96 and the release taper of the proximal portion 116 of the drive cannula 114 are arranged and configured not to remain in abutting engagement with the retention surface 224 of the resilient arm 188 in a way that would allow the drill bit 66 to be axially retained. Moreover, as is generally depicted in FIGS. 17A-19C, the external splines 260 of the proximal portion 116 of the drive cannula 114 are radially arranged about the axis AX relative to the bore 122. Thus, because the external splines 260 of the proximal portion 116 of the drive cannula 114 define the lock surfaces 262 and are radially arranged with the bore 122 adjacent to the bore corners 122C, the retention surface 224 of the resilient arm 188 needs to be radially aligned about the axis with the outermost drive portion 202 of the interface 124 in order to engage one of the lock surfaces 262. The specific shape and arrangement of the proximal portion 116 of the drive cannula 114 and the output hub 96 can be adjusted to different arrangements or geometries so long as the lock surfaces are still present and arranged relative to the bore in a way that makes the lock surfaces accessible to the retention surfaces of the bit when the drive interface is received in the bore.

Figure 15D:
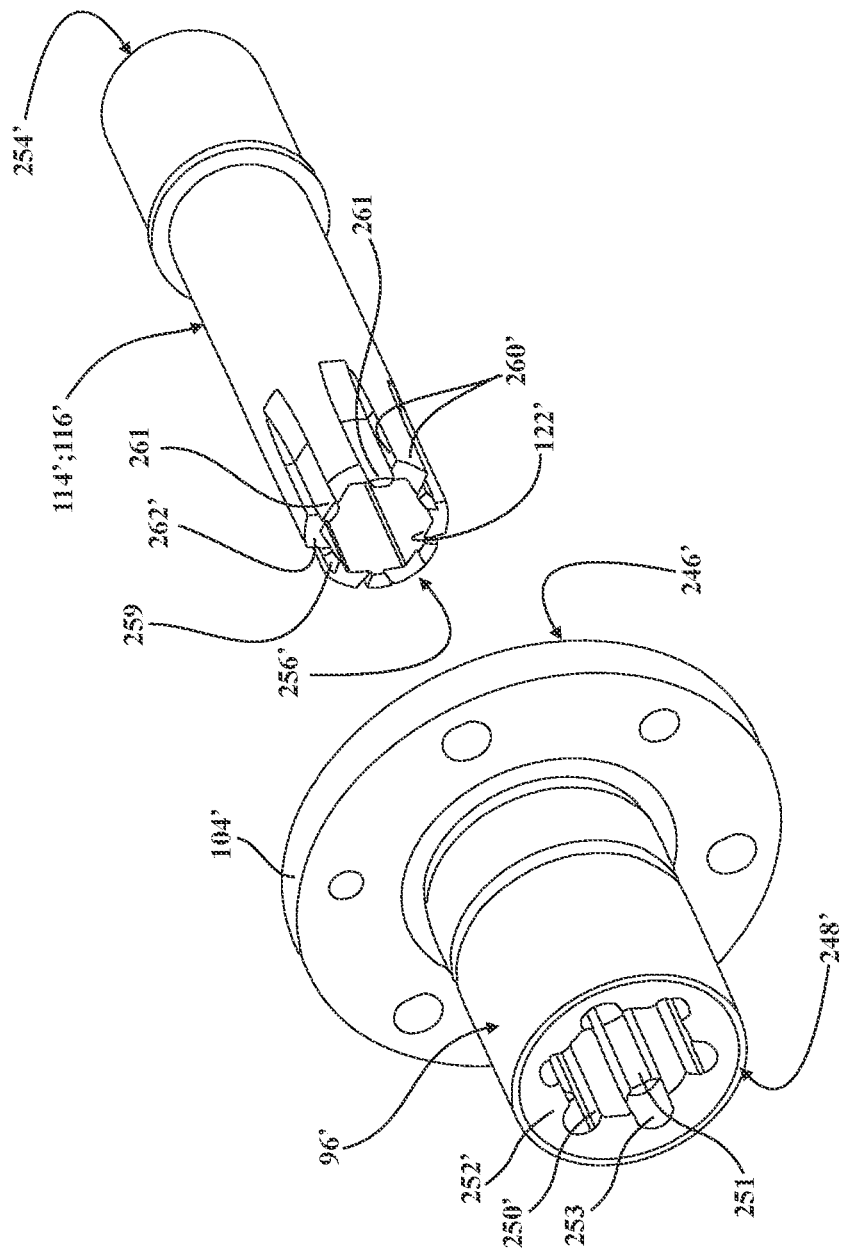
FIG. 15D is a perspective view of another proximal portion of a drive cannula positioned adjacent to another output hub.
Figure 16:
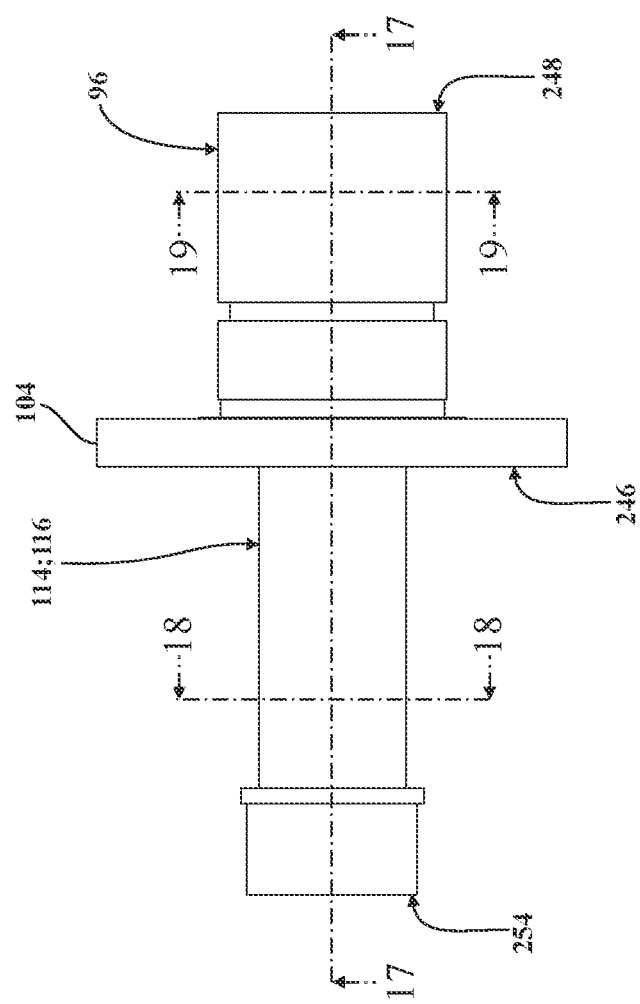
FIG. 16 is a top-side view of the proximal portion of the drive cannula and the output hub assembled as depicted in FIG. 15B.
Figure 20:
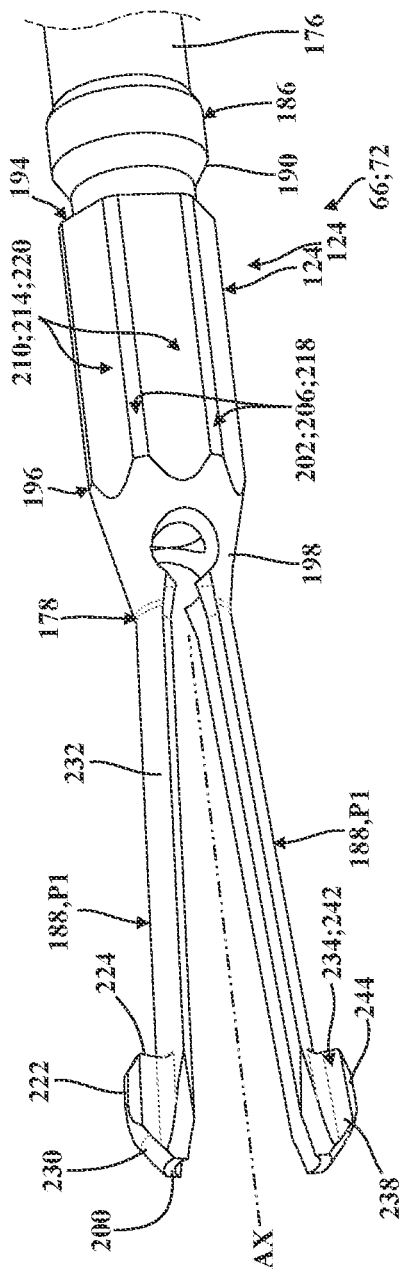
FIG. 20 is a partial perspective view of the drill bit of FIGS. 1-2, 4-5, 7B-7I, 15B-15C, 17B-17C, and 19B-19C showing additional detail of the resilient arms, the interface, and the stop adjacent to the proximal end of the shank.
Figure 21:
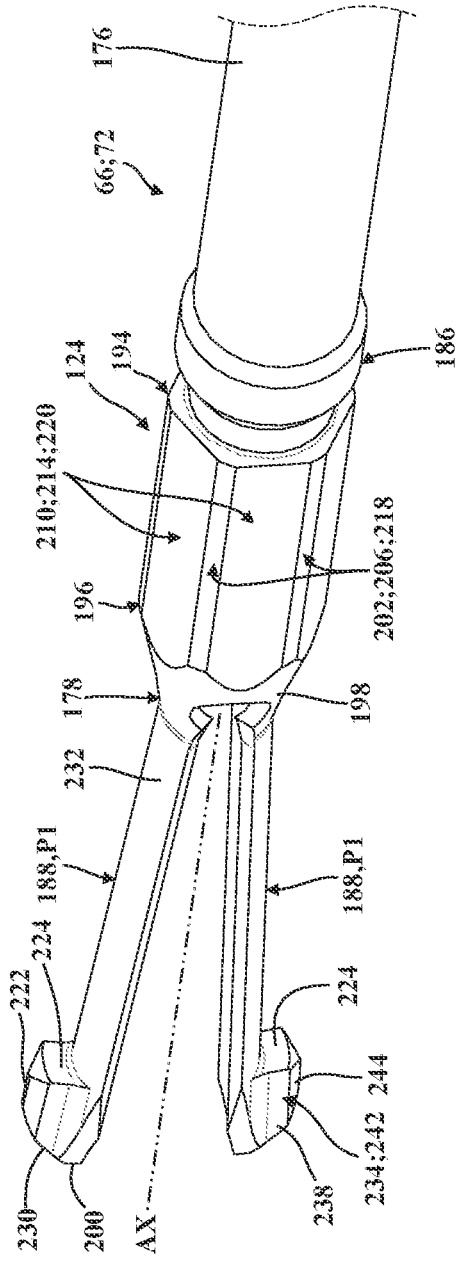
FIG. 21 is another partial perspective view of the portions of the drill bit illustrated in FIG. 20.

Referring now to FIG. 15D, an alternative embodiment of the drive cannula and the output hub is illustrated and described. The proximal portion 116' of the drive cannula 114' cooperates with the output hub 96' of the actuator assembly to facilitate rotating the drill bit about the axis AX via splined engagement between the output hub 96' and the drive cannula 114'. The output hub 96' extends between a distal hub end 246' and a proximal hub end 248', and comprises one or more internal splines 250' which extend from the distal hub end 246', adjacent to the integrated carrier 104', toward but spaced from the proximal hub end 248'. Between each pair of the splines 250', there may be a recess 251. Aligned with those recesses axially, there may be a pocket 253 that provides additional clearance for the resilient arms to flex outward. Here, the output hub 96' is provided with a lockout taper 252' which has a generally frustoconical profile extending internally to merge with the internal splines 250' such that the internal splines 250' terminate distal from the proximal hub end 248'.

With continued reference to FIG. 15D, the proximal portion 116' of the drive cannula 114' extends between a distal end 254' of the proximal portion 116' of the drive cannula 114' and a proximal end 256' of the proximal portion 116' of the drive cannula 114'. Here, the tapered seat surface is formed at the distal end 254 and tapers internally into the hexagonal bore 122', as noted above. The bore 122', in turn, extends along the axis AX toward the proximal end 256'. In some configurations, the proximal portion 116' of the drive cannula 114' is provided with a release taper 259 which similarly tapers internally into the hexagonal bore to help facilitate releasing the drill bit from the surgical handpiece assembly. The splined engagement is facilitated by one or more grooves formed by the external surface of the proximal portion of the drive cannula 114' or one or more projections extending from the external surface of the proximal portion 116 of the drive cannula 114. In one configuration, shown in FIG. 15D, the one or more projections comprise external splines 260' which are formed extending from the proximal end 256' toward but spaced from the distal end 254'. At the proximal end 256', the external splines 260' define lock surfaces 262' adjacent to the release taper 259. The lock surfaces 262' are radially and at least partially axially aligned with the lock surfaces 262'. The release taper 259 may be defined by protrusions 261 that extend proximally relative to the lock surfaces 262'. The lock surfaces 262' are arranged to abut the retention surface 224 of the resilient arm 188 to axially lock the drill bit 66 to the surgical handpiece assembly 62. The specific shape and arrangement of the internal splines and external splines can be adjusted to different arrangements or geometries so long as the lock surfaces are still present and arranged relative to the bore in a way that makes the lock surfaces accessible to the retention surfaces of the bit when the drive interface is received in the bore. In some configurations, the release taper 259 and lock surfaces 262' are integral and cooperate to form a retention surface of the proximal portion 116' of the drive cannula 114' that is configured to abut the retention surface of the resilient arm. The lock surface of the proximal portion 116' of the drive cannula 114 may be perpendicular to the axis AX proximally to distally to prevent accidental release of the drill bit from the drive cannula 114'.

In this configuration, the proximal end 256' is spaced distally from the proximal hub end 248' of the output hub 96'. The lock surfaces 262' of the proximal portion 116' of the drive cannula 114' are likewise spaced distally from the proximal hub end 248' and, the lock surfaces 262' are also spaced distally from the lockout taper 252' of the output hub 96'. The release taper 259 and thus, the proximal end of the protrusion 261 is also spaced distally from the lockout taper 252 of the output hub 96'. This configuration ensures that axial retention of the drill bit is effected via engagement between the retention surface of the resilient arm and one of the lock surfaces 262' of the proximal portion 116' of the drive cannula 114', and not with other portions of the proximal portion 116' of the drive cannula 114' or the output hub 96'. Put differently, the lockout taper 252' of the output hub 96' and the release taper 259 of the drive cannula 114' are arranged and configured not to remain in abutting engagement with the retention surface of the resilient arm in a way that would allow the drill bit to be axially retained. Because the lock surfaces 262' are radially arranged with the bore 122' adjacent to the bore corners 122C, the retention surface of the resilient arm needs to be radially aligned about the axis with the outermost drive portion of the interface in order to engage one of the lock surfaces.

As will be appreciated from the subsequent description below, the insertion portion 72 of the drill bit 66 may be configured in different ways sufficient to releasably attach to the surgical handpiece assembly. By way of non-limiting example, in some of the illustrated configurations, such as those depicted in FIGS. 20-23, the insertion portion 72 comprises a pair of generally identical, diametrically opposed resilient arms 188, each having respective retention surfaces 224 radially aligned with respective outermost drive portions 202 of the interface 124. However, it will be appreciated that other configurations are contemplated. By way of non-limiting example, it is conceivable that the insertion portion 72 could comprise two resilient arms 188 which are radially spaced from outermost drive portions 202 about the axis AX at 60 degrees, or at intervals thereof (generally illustrated schematically in FIGS. 30 and 32-33). Other intervals are contemplated, such as 15 degrees, 30 degrees, 45 degrees, or intervals of each. In some configurations, the resilient arm 188 and one of the outermost drive portions 202 are positioned within 15 degrees of one another relative to the axis AX.

Furthermore, it is conceivable that the insertion portion 72 could comprise a plurality of resilient arms 188 with different or similar configurations from one another, such as with differently shaped, sized, or angled retention surfaces 224, finger portions 234, aligning elements 242, and the like (illustrated schematically in FIG. 30). Further still, it will be appreciated that the insertion portion 72 could comprise a single resilient arm 188, such as is depicted in the configuration illustrated in FIGS. 25-26, or could comprise more than two resilient arms 188, such as is depicted in the configuration illustrated in FIGS. 27-28 which comprises three resilient arms 188. Furthermore, the configurations of the interface 124 illustrated schematically in FIGS. 32-33 could each have between one and six resilient arms 188. Moreover, while some of the configurations of the interface 124 comprise resilient arms 188 which are diametrically spaced from each other about the axis AX and have similar or identical profiles, other arrangements are contemplated. By way of example, the interface 124 illustrated schematically in FIG. 30 is shown as being able to comprise five resilient arms 188 of various configurations (e.g., with retention surfaces 224 of different profiles and orientations). Other configurations are contemplated.

While the illustrated drill bit 66 is configured as a twist drill with helical flutes 182 to promote tissue penetration, other types of cutting tip portions 70 could be employed in some configurations. For example, the cutting tip portion 70 could be realized as a burr, a reamer, a tap, a screwdriver, and the like. Moreover, as shown in the configuration illustrated in FIG. 28, the drill bit 66 may further comprise a drill cannula 264 extending along the axis AX such that the drill bit 66 is cannulated in some configurations.

As noted above, the interface 124 of the drill bit 66 of the present disclosure could have a number of different cross-sectional profiles or configurations sufficient to be received within and rotate concurrently with the bore 122. In some configurations, the interface 124 may comprise different numbers of planar surfaces 220. By way of illustration, the configurations of the interface 124 illustrated in FIGS. 29-32 each comprise at least four planar surfaces 220: six in the configurations illustrated in FIGS. 29-30, four in the configuration illustrated in FIG. 31, and twelve in the configuration illustrated in FIG. 32. However, other configurations may employ fewer than four planar surfaces 220, such as the configuration illustrated in FIG. 33 which comprises two planar surfaces. It will be appreciated that other arrangements and configurations of the interface 124 and/or the planar surfaces 220 are contemplated.

Figure 31:
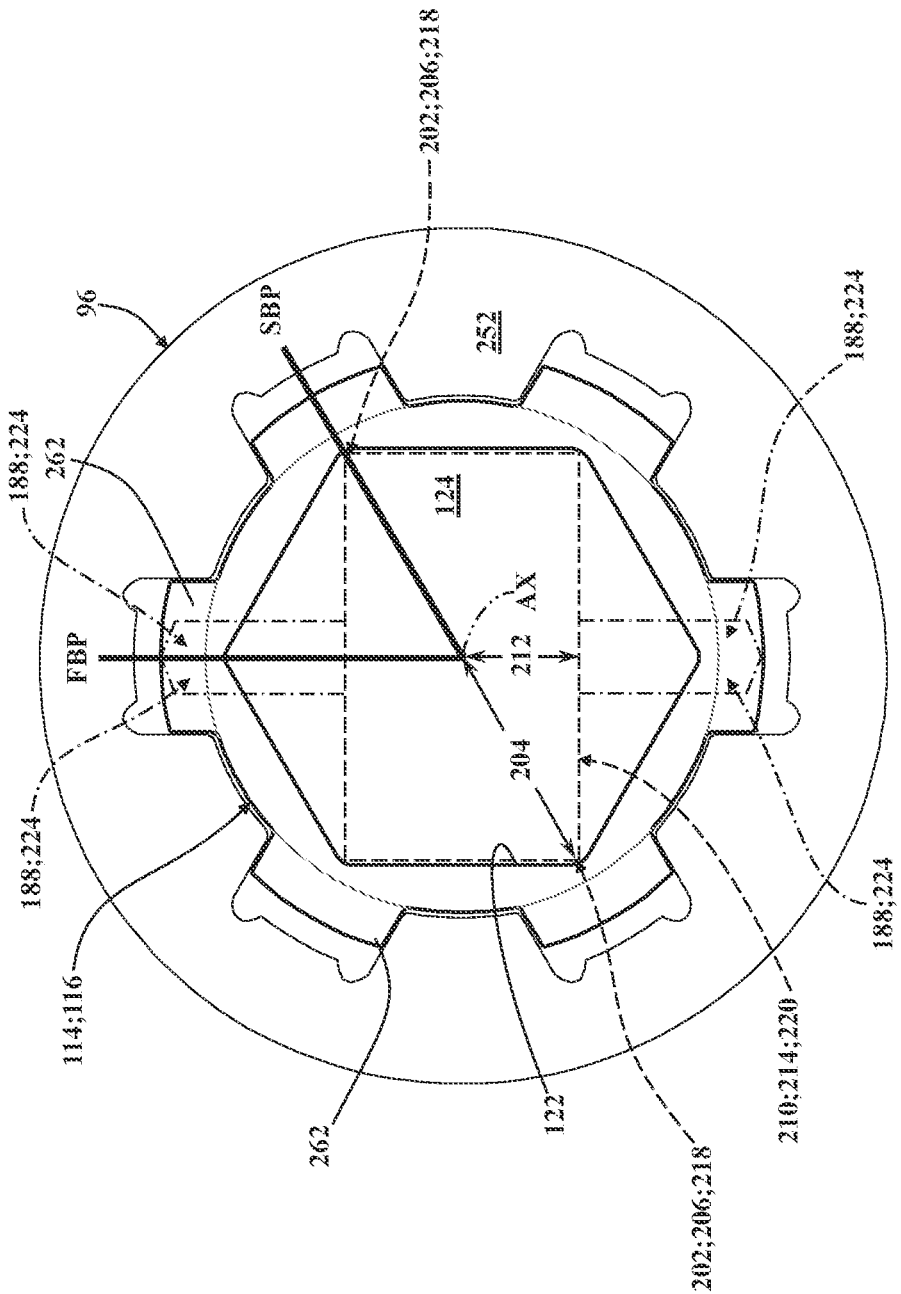
FIG. 31 is another front-side schematic view representing the proximal portion of the drive cannula and the output hub of FIGS. 29-30 with a configuration of a drill bit having an interface shown with a generally rectangular profile.
Figure 32:
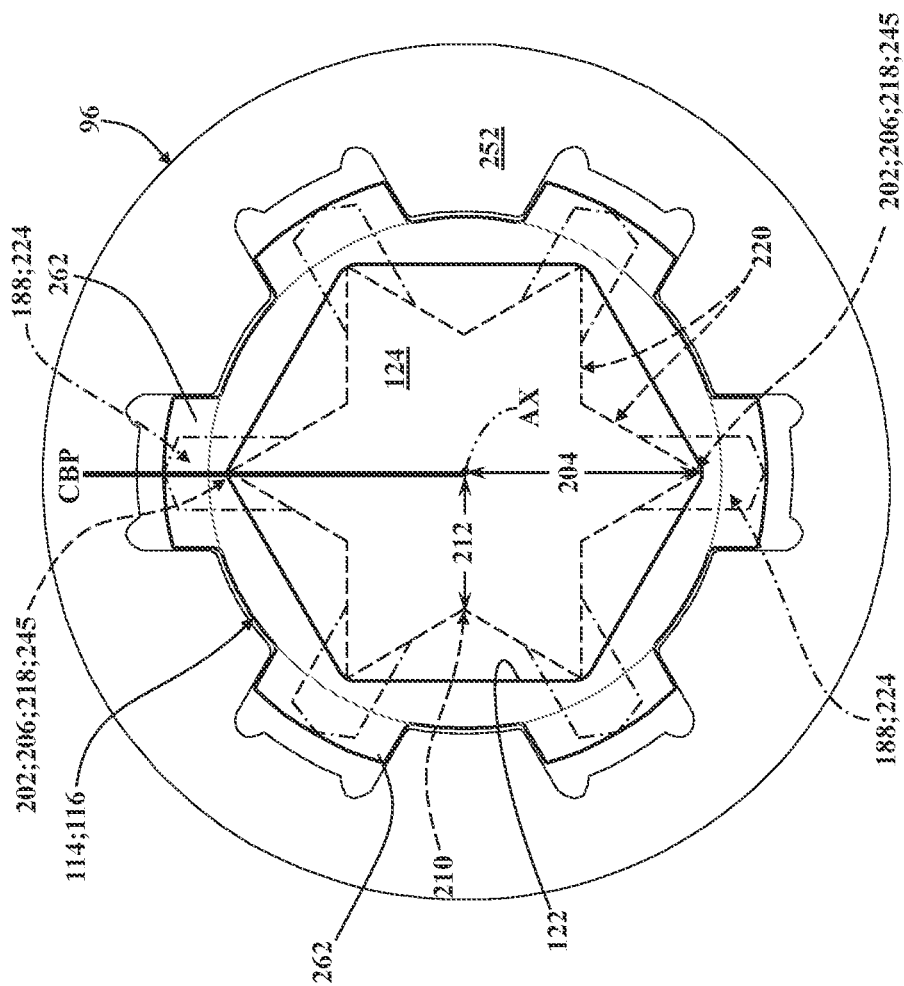
FIG. 32 is another front-side schematic view representing the proximal portion of the drive cannula and the output hub of FIGS. 29-31 with a configuration of a drill bit having an interface shown with a generally star-shaped profile.
Figure 33:
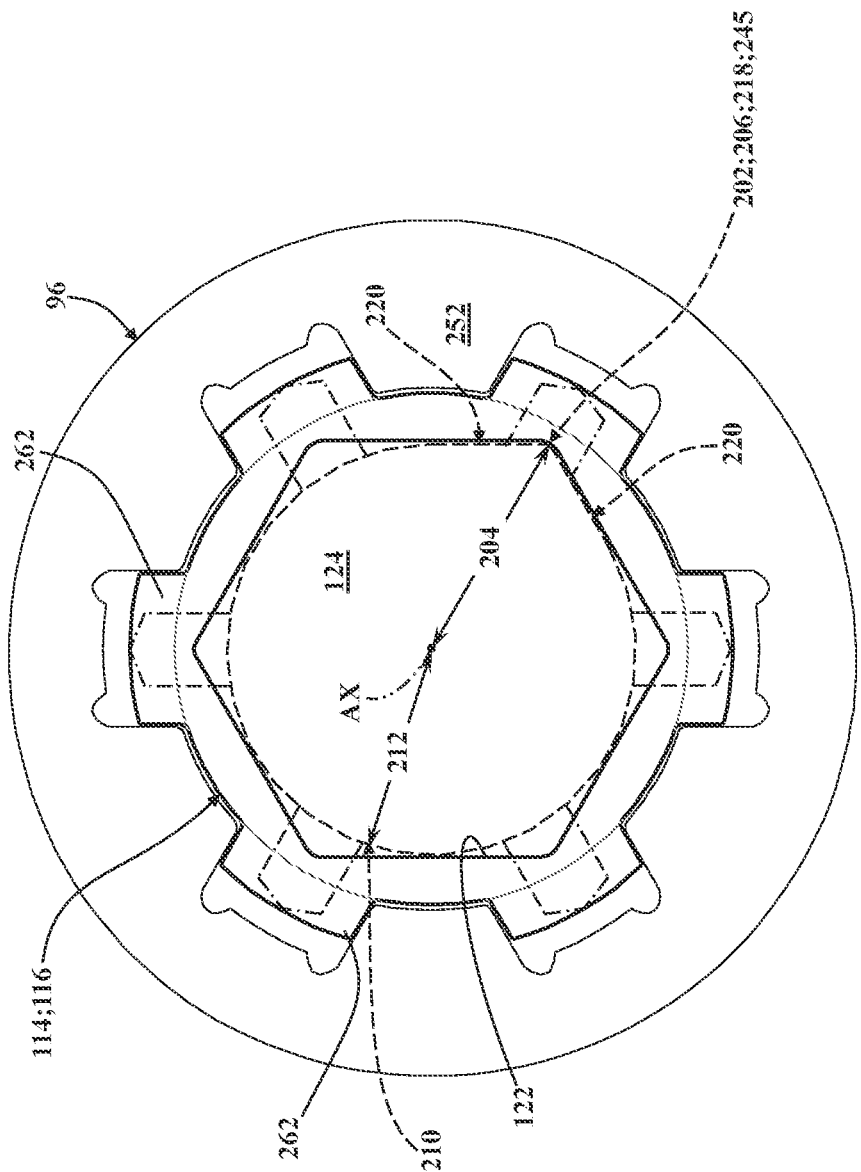
FIG. 33 is another front-side schematic view representing the proximal portion of the drive cannula and the output hub of FIGS. 29-32 with a configuration of a drill bit having an interface shown with an irregularly-shaped profile.

In some configurations, the interface 124 may comprise different numbers of corners 218 which define the outermost drive portions 202. By way of illustration, the configurations of the interface 124 illustrated in FIGS. 29-30 are generally hexagonal and each comprise six corners 218 which define outermost drive portions 202. The interface 124 illustrated in FIG. 31 is generally rectangular and comprises four corners 218 which define outermost drive portions 202. The interface 124 illustrated in FIG. 32 is generally star-shaped and comprises six drive lobes 245, each of which comprises a corner 218 which defines an outermost drive portion 202. In configurations where the interface 124 comprises drive lobes 245 which terminate at corners 218 defined such as by points or apexes, at least two drive lobes 245 may define outermost drive portions 202. However, as noted above, other configurations are contemplated, such as where the interface 124 comprises three drive lobes 245, more than four drive lobes 245, and the like. The interface illustrated in FIG. 33 comprises an irregular shape which comprises a single corner 218 defining an outermost drive portion 202. It will be appreciated that other arrangements and configurations of the corners 218 and/or the outermost drive portions 202 are contemplated.

Referring now to the configuration of the insertion portion 72 of the drill bit 66 depicted schematically in FIG. 29, one of the retention surfaces 224 of the resilient arms 188 and one of the outer drive surfaces 206 of the outermost drive portions 202 of the interface 124 comprise, define, or are otherwise aligned with a common bisecting plane CBP intersecting the axis AX to define two equal portions of the retention surface 224 and the resilient arm 188 and two equal portions of the outer drive surface 206 and the outermost drive portion 202. It will be appreciated that the symmetrical relationship described above is exemplary, and other configurations are contemplated.

Referring now to the configuration of the insertion portion 72 of the drill bit 66 depicted schematically in FIG. 32, one of the retention surfaces 224 of one of the resilient arms 188 and one of drive lobes 245 comprise, define, or are otherwise aligned with a common bisecting plane CBP intersecting the axis AX to define two equal portions of the retention surface 224 of the resilient arm 188 and two equal portions of the outermost drive portion 202 (here, defined by the apexes of the triangular drive lobes 245). Here too, it will be appreciated that the symmetrical relationship described above is exemplary, and other configurations are contemplated.

Referring now to the configuration of the insertion portion 72 of the drill bit 66 depicted schematically in FIG. 31, one of the retention surfaces 224 of the resilient arms 188 comprises, defines, or is otherwise aligned with a first bisecting plane FBP that intersects the axis AX to define two equal portions of the retention surface 224. Furthermore, one of the outermost drive portions 202 of the interface 124 comprises, defines, or is otherwise aligned with a second bisecting plane SBP that intersects the axis AX to define two equal portions of the outermost drive portion 202 (here, defined by the apexes of two of the corners 218 of the rectangular profile). In this configuration, the second bisecting plane SBP is radially spaced approximately 60 degrees from the first bisecting plane FBP about the axis AX. Thus, as noted above, the retention surface 224 of the resilient arm 188 may be radially aligned with the outermost drive portion 202 of the interface 124 at intervals of approximately 60 degrees. Here too, other configurations are contemplated.

Referring now to FIG. 2, in one configuration, the interface 124 has an interface length IL defined between the distal interface end 194 and the proximal interface end 196, and the shank 176 has a shank length SL defined between the distal end 180 and the proximal end 178, with the shank length SL being greater than or equal to three times the interface length IL. However, those having ordinary skill in the art will appreciate that other configurations are contemplated for the drill bit 66, such as with a shank length SL is five or more times the interface length IL. Referring now to FIG. 22, in the illustrated configuration, the retention surface 224 is spaced from the proximal interface end 196 at a retention distance RD that is greater than or equal to the interface length IL. Here too, other configurations are contemplated.

Figure 34:
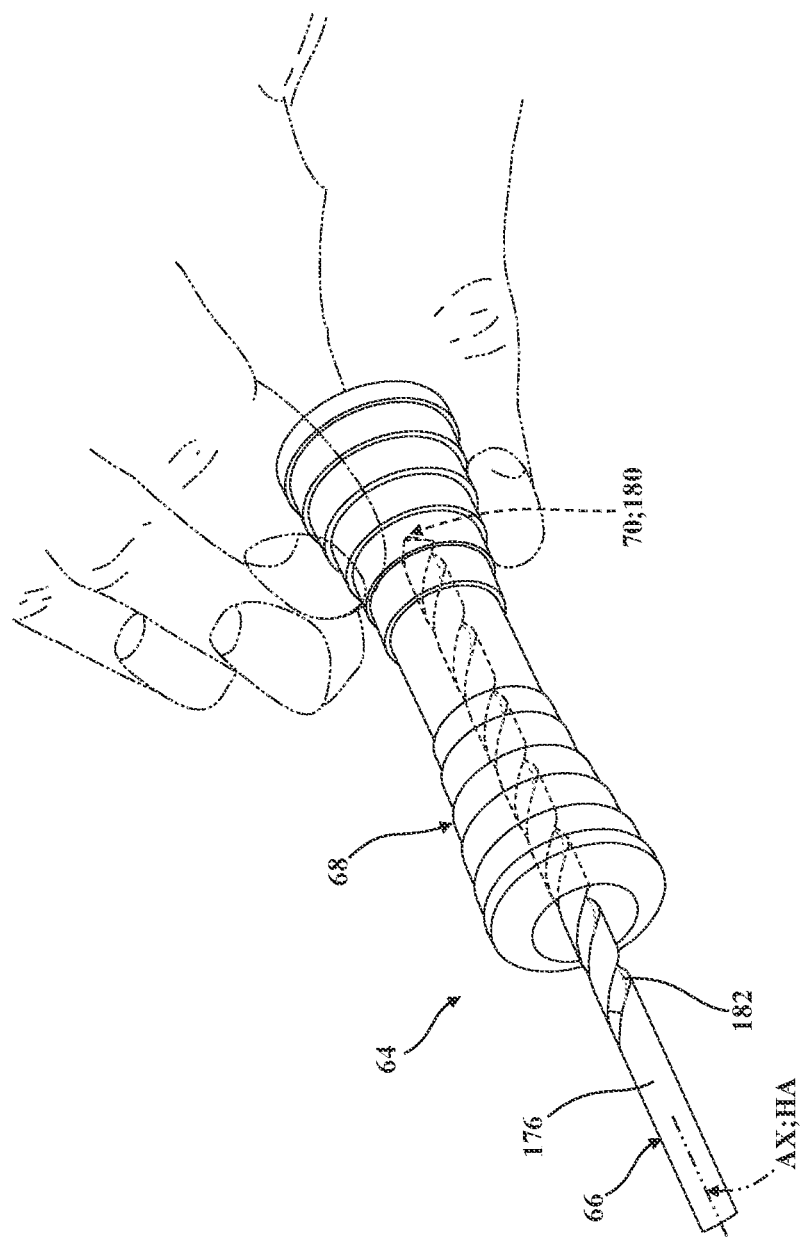
FIG. 34 is a partial perspective view of the end effector assembly of FIGS. 1-2, shown with the distal cutting tip portion of the drill bit disposed within the tip protector.
Figure 35:
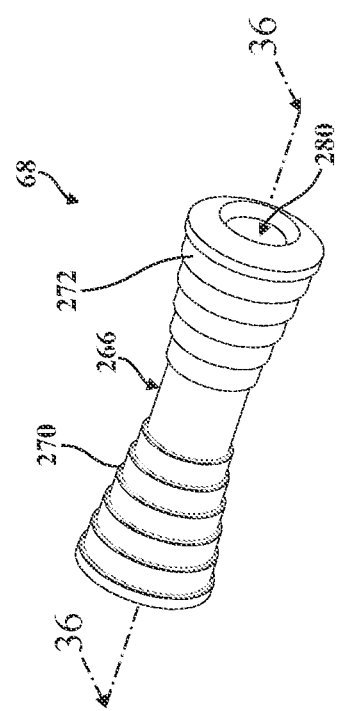
FIG. 35 is a perspective view of the tip protector of the end effector assembly illustrated in FIGS. 1-2 and 34.

Referring now to FIGS. 1-2 and 34, as noted above, in some configurations, the tip protector 68 of the end effector assembly 64 is provided to facilitate releasably attaching the drill bit 66 to the drive cannula 114 of the surgical handpiece assembly 62 such that the tip protector 68 at least partially conceals the cutting tip portion 70 of the drill bit 66. Thus, a user can grasp the tip protector 68 and thereby handle the drill bit 66 to facilitate attachment with the surgical handpiece assembly 62, without contacting the cutting tip portion 70, before subsequently removing the tip protector 68 from the cutting tip portion 70. To this end, as shown in FIG. 36, the tip protector 68 generally comprises a handle 266 configured to be grasped by the user, and a receptacle 268 capable of receiving the cutting tip portion 70 of the drill bit 66.

Figure 36:
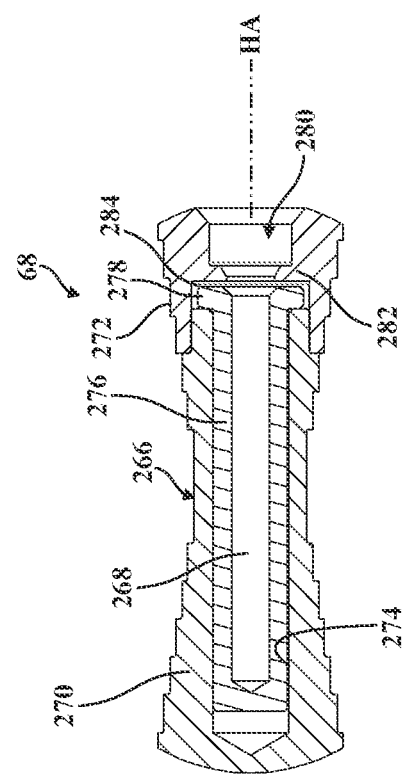
FIG. 36 is a sectional view taken along line 36-36 in FIG. 35.
Figure 37:
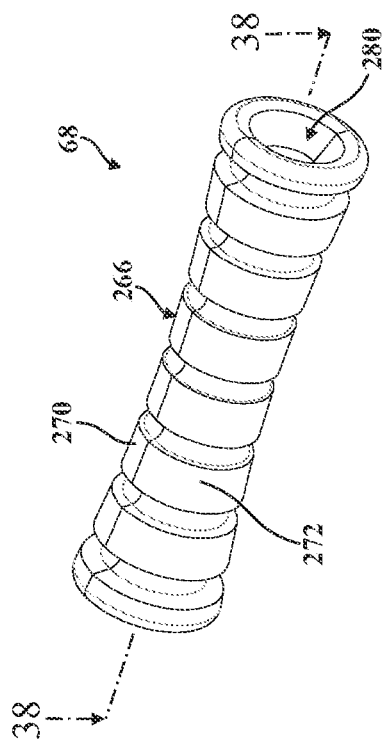
FIG. 37 is a perspective view of another tip protector configuration of the end effector assembly.
Figure 38:
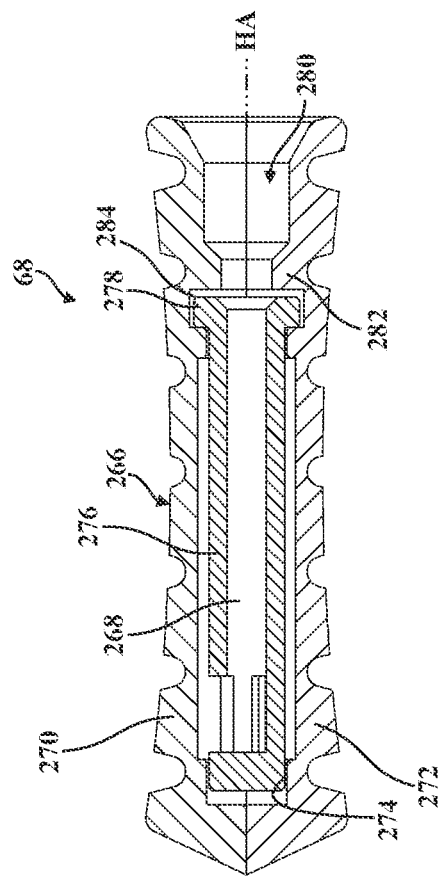
FIG. 38 is a sectional view taken along line 38-38 in FIG. 37.

In the configuration of the tip protector 68 illustrated in FIGS. 1-2 and 34-36, and as is best depicted in FIG. 36, the handle 266 comprises a first handle body 270 and a second handle body 272 which are operatively attached together axially, such as via a press-fit engagement. The first handle body 270 defines a handle bore 274 extending along a handle axis HA. A receiver 276 is rotatably supported within the handle bore 274 and comprises the receptacle 268 which is capable of receiving the cutting tip portion 70 of the drill bit 66, such as via a friction-fit engagement. In this configuration, the receiver 276 comprises a flange 278 which abuts a portion of the first handle body 270 adjacent to the second handle body 272. The second handle body 272 comprises an inlet mouth 280 which tapers inwardly to a stepped region 282 which, in turn, is disposed adjacent to the flange 278 of the receiver 276 to define a recess 284 between the first handle body 270 and the stepped region 282. The flange 278 is disposed within the recess 284 such that the receiver 276 constrained form translating along the handle axis HA and out of the handle bore 274. Thus, the receiver 276 is able to rotate about the handle axis HA within the handle bore 274 without rotating the handle 266.

When the cutting tip portion 70 is disposed within the receptacle 268, the drill bit 66 effectively rotates concurrently with the receiver 276 about the handle axis HA. Here, the user can grasp the handle 266 and attach the drill bit 66 to the surgical handpiece assembly 62 without contacting the cutting tip portion 70. Moreover, the relative rotation afforded between the handle 266 and the drill bit 66 in this configuration complements the "self-aligning" features of drill bit 66 described above in connection with FIGS. 24A-24B. Specifically, the indexing of the interface 124 relative to the bore 122 via the aligning element 242 can occur without translating rotation back to the handle 266 in this configuration, which promotes attachment of the drill bit 66 to the surgical handpiece assembly 62 in an efficient manner.

As noted above, the tip protector 68 can be configured in a number of different ways to promote handling of the drill bit 66. For example, in the configuration of the tip protector 68 depicted in FIGS. 37-38, the first handle body 270 and the second handle body 272 of the handle 266 are operatively attached together laterally, such as via interlocking features, adhesion, bonding, and the like. In this configuration, the recess 284 is likewise provided to accommodate the flange 278 so as to restrict axial movement of the receiver 276 relative to the handle 266, and the receptacle 268 is similarly configured to releasably secure to the cutting tip portion 70 of the drill bit, such as by frictional engagement.

Figure 39:
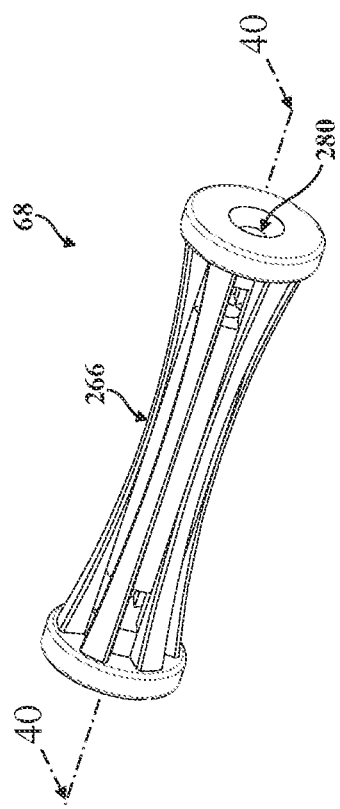
FIG. 39 is a perspective view of another tip protector configuration of the end effector assembly.
Figure 40:
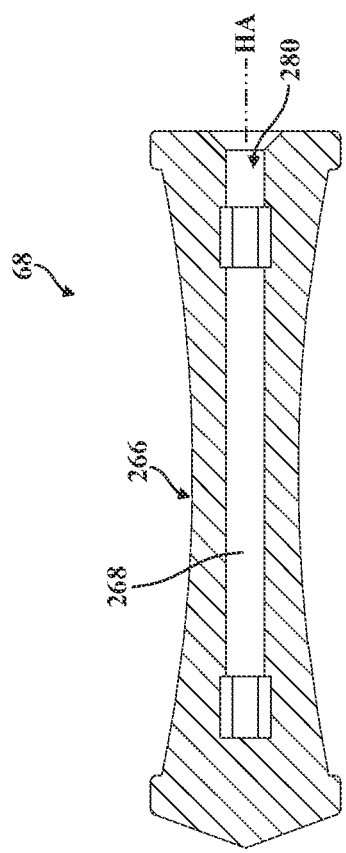
FIG. 40 is a sectional view taken along line 40-40 in FIG. 39.

The configuration of the tip protector 68 depicted in FIGS. 39-40 is realized as a unitary, one-piece component such that the handle 266 defines the receptacle 268, which may be utilized in connection with configurations where relative rotation between the handle 266 and the drill bit 66 is undesirable or unnecessary. In some configurations, such as those comprising single-piece tip protectors 68, at least a portion of the tip protector 68 may be resiliently deformable, may be tapered or stepped to accommodate cutting tip portions 70 of different sizes, and the like. It will be appreciated that these features could also be utilized in connection with other types of tip protectors 68 illustrated herein.

Figure 41:
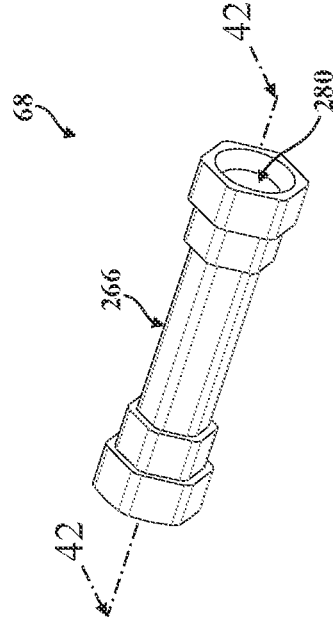
FIG. 41 is a perspective view of another tip protector configuration of the end effector assembly.
Figure 42:
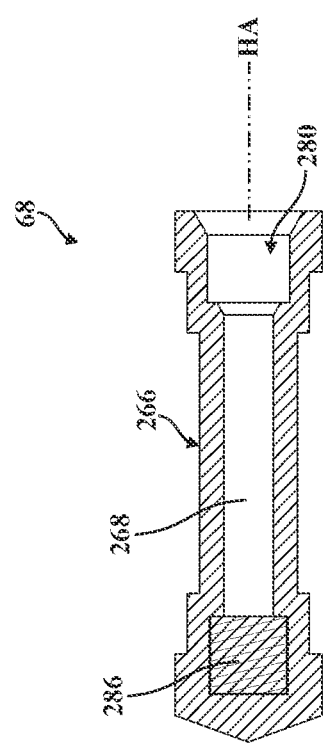
FIG. 42 is a sectional view taken along line 42-42 in FIG. 41.

The configuration of the tip protector 68 depicted in FIGS. 41-42 employs a unitary, one-piece handle 266 in which a magnet 286 is disposed. Here, the receptacle 268 is likewise defined by the handle 266, and extends along the handle axis HA between the magnet 286 and the inlet mouth 280. Where the drill bit 66 is manufactured from a ferromagnetic material, the magnet 286 will attract the cutting tip portion 70 to promote releasable retention between the tip protector 68 and the drill bit 66. Here, it will be appreciated that the receptacle 268 may be sized so as to permit a looser fit with the drill bit 66 and thereby facilitate relative rotation between the drill bit 66 and the handle 266 while axially retaining the drill bit 66 via the magnet 286. In some configurations, such as where the magnet 286 is relatively strong, the receptacle 268 may be sized to receive cutting tip portions 70 of various sizes, diameters, and the like.

Figure 43:
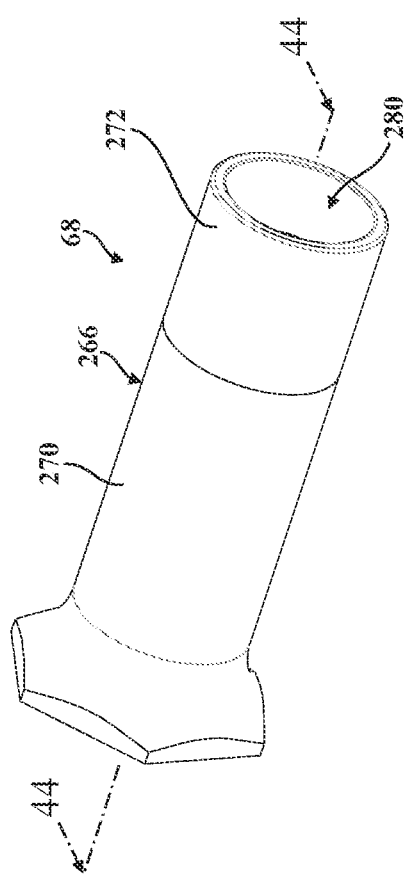
FIG. 43 is a perspective view of another tip protector configuration of the end effector assembly.
Figure 44:
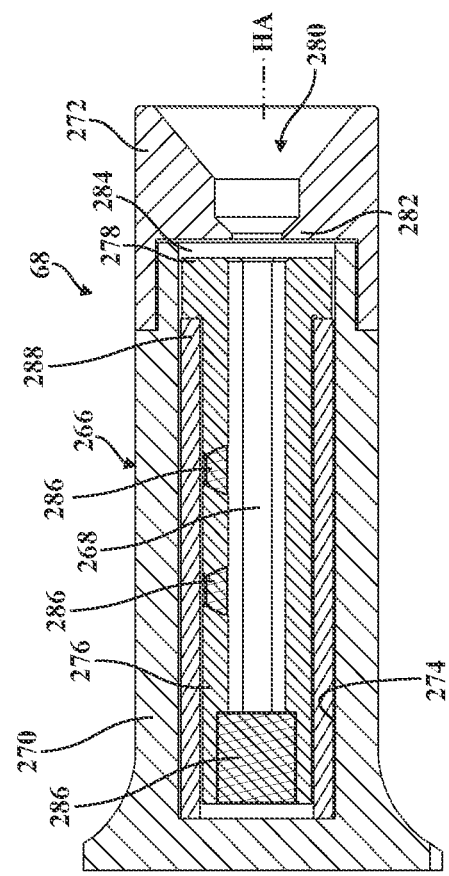
FIG. 44 is a sectional view taken along line 44-44 in FIG. 43.

The configuration of the tip protector 68 depicted in FIGS. 43-44 employs a handle 266 which is configured similarly to the configuration of the tip protector 68 described above in connection with FIGS. 35-36. In this configuration, however, a sleeve 288 is supported in the first handle body 270. Here, the sleeve 288 rotatably supports the receiver 276 and cooperates with the second handle body 272 to define the recess 284 in which the flange 278 is disposed. Similar to the configuration of the tip protector 68 described above in connection with FIGS. 41-42, magnets 286 are likewise employed to help retain the cutting tip portion 70 of the drill bit 66. In this configuration, however, magnets 286 are also disposed radially about the handle axis HA to provide further magnetic attraction to the drill bit 66 and, in some configurations, to facilitate retaining cutting tip portions 70 of various sizes, diameters, and the like. By way of illustrative example, a cutting tip portion 70 with a diameter that is smaller than the receptacle 268 of the receiver 276 may be retained both axially and laterally by this arrangement of magnets 286.

Figure 45:
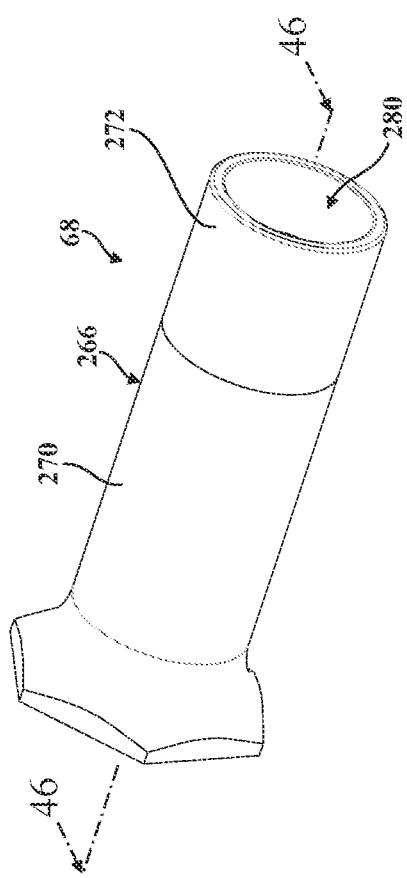
FIG. 45 is a perspective view of another tip protector configuration of the end effector assembly.
Figure 46:
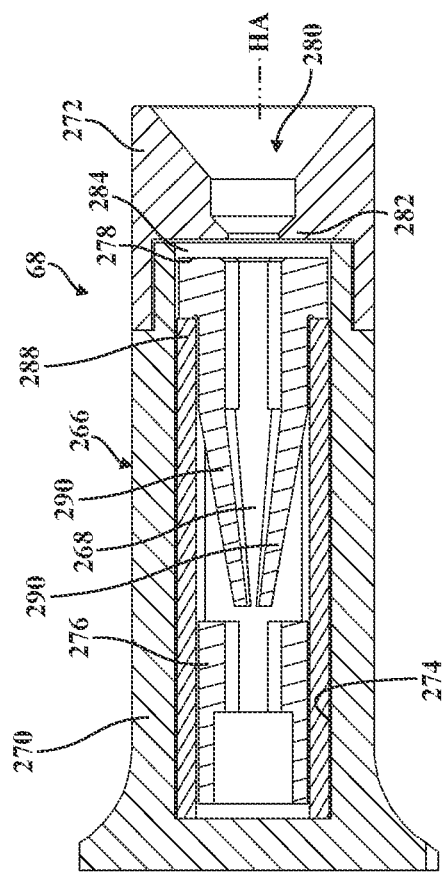
FIG. 46 is a sectional view taken along line 46-46 in FIG. 45.

The configuration of the tip protector 68 depicted in FIGS. 45-46 employs a handle 266, a first handle body 270, a second handle body 272, and a sleeve 288 which are similar to the configuration of the tip protector 68 described above in connection with FIGS. 43-44. However, in this configuration, the receiver 276 comprises one or more resilient tabs 290 which extend inwardly toward the handle axis HA. Here, when the cutting tip portion 70 is inserted into the receptacle 268, the resilient tabs 290 contact and exert force on the cutting tip portion 70. Thus, it will be appreciated that this configuration of the tip protector 68 can likewise be employed to releasably attach to cutting tip portions 70 of various sizes, diameters, and the like.

Figure 7A:
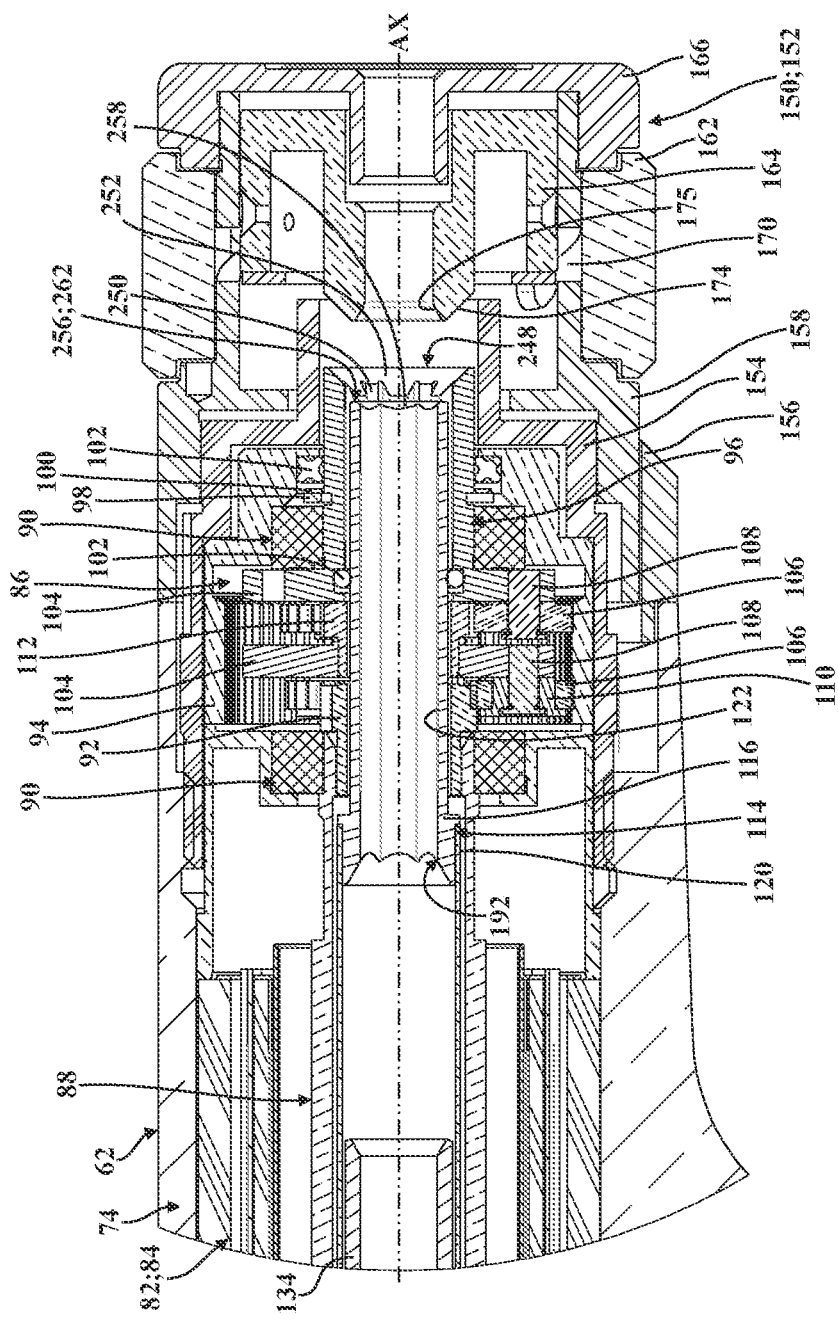
FIG. 7A is an enlarged detail view taken at indicia 7 in FIG. 6, shown depicting portions of the measurement module, the drive cannula, the release assembly, and the actuator assembly within the handpiece housing assembly.
Figure 7B:
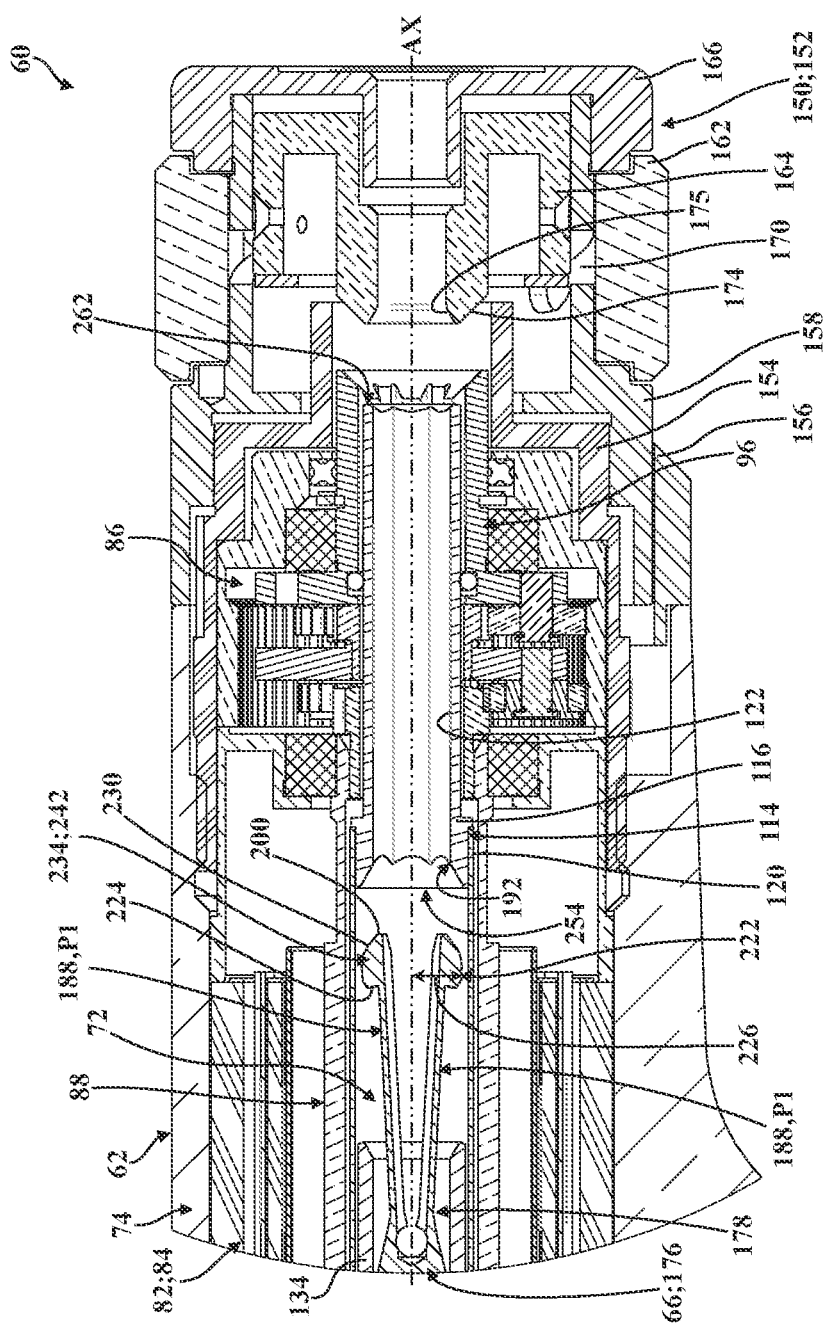
FIG. 7B is another enlarged detail view of the surgical handpiece system of FIGS. 1 and 7A, shown with a pair of resilient arms arranged at a proximal end of the drill bit approaching a proximal portion of the drive cannula.
Figure 7C:
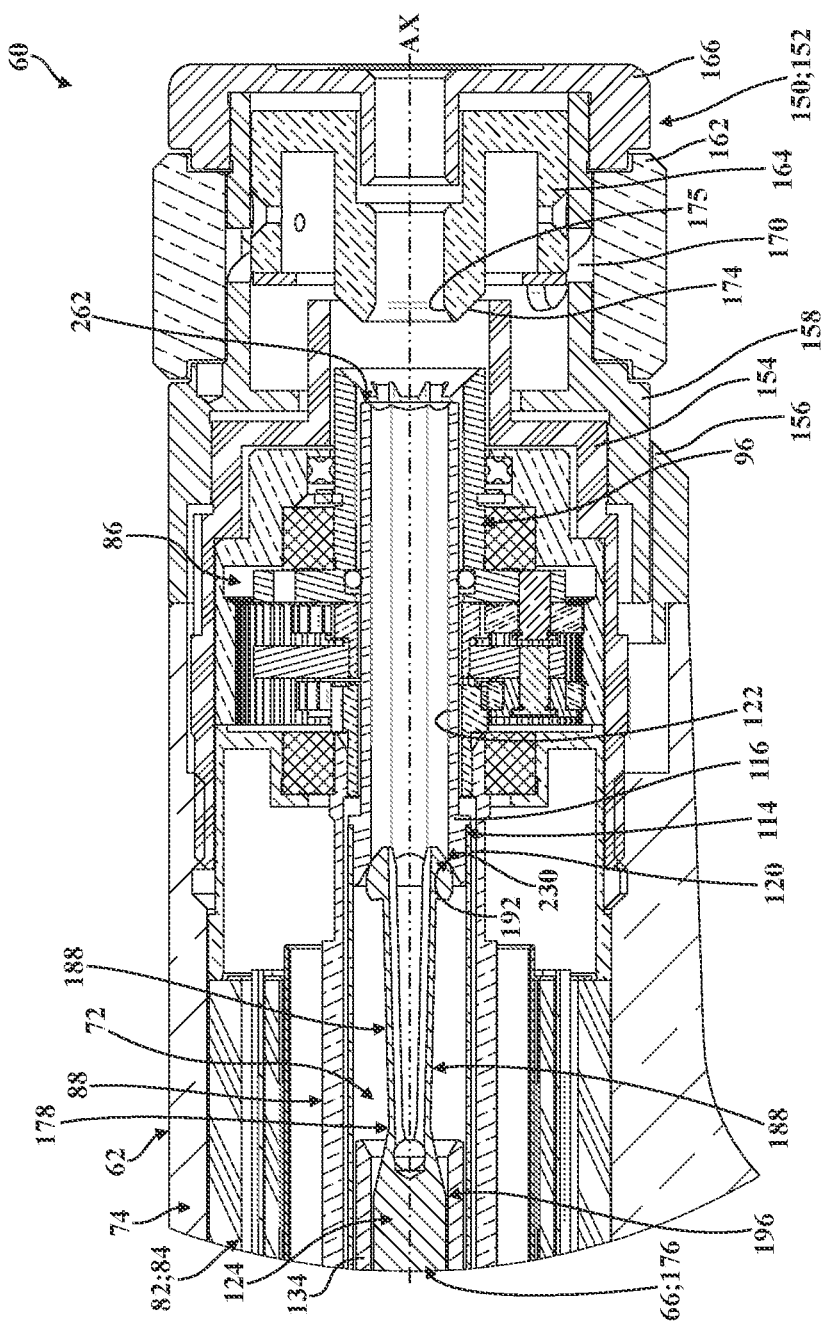
FIG. 7C is another enlarged detail view of the surgical handpiece system of FIGS. 7A-7B, shown with the resilient arms of the drill bit engaging against a seat surface of the proximal portion of the drive cannula and deflecting towards each other.
Figure 7D:
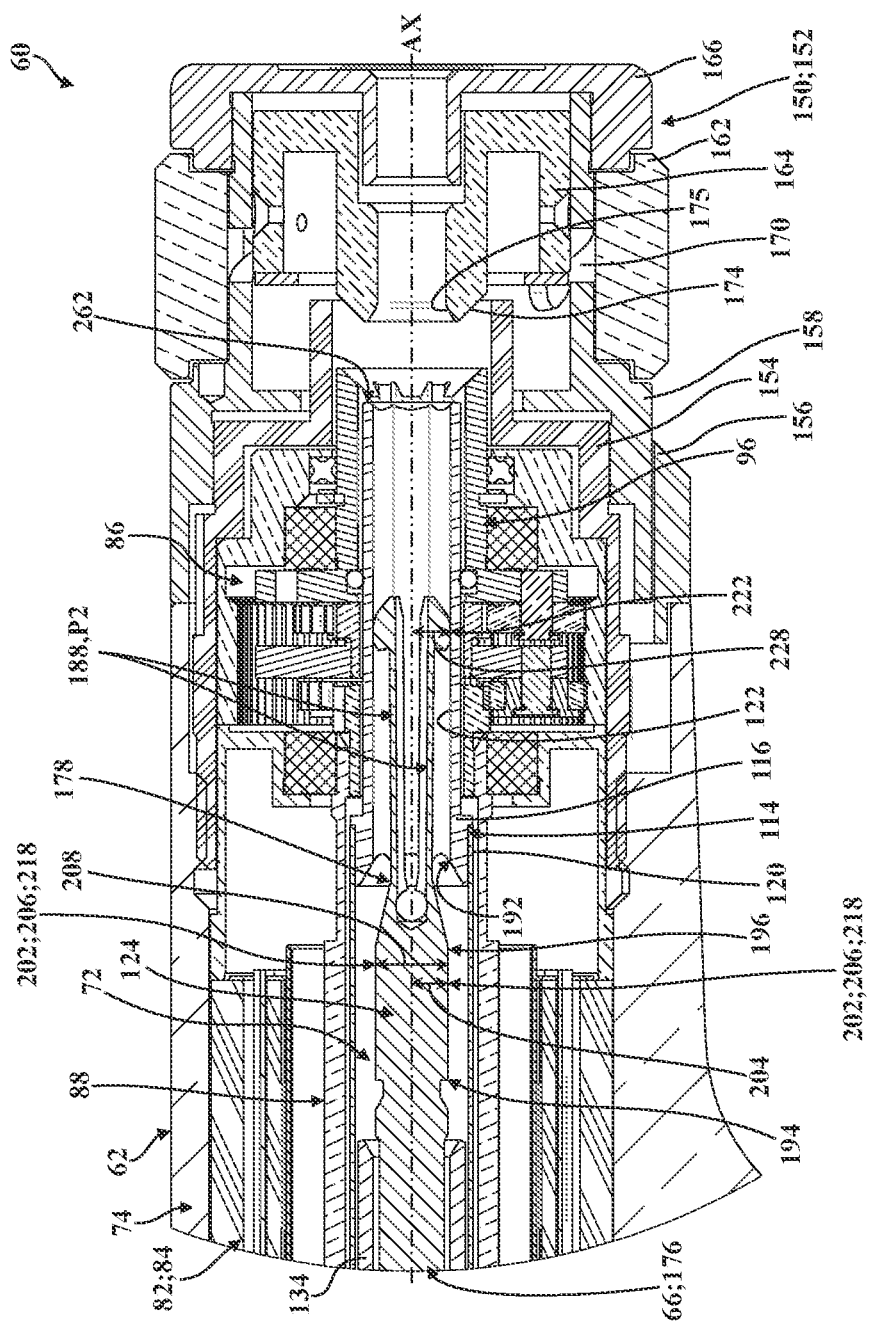
FIG. 7D is another enlarged detail view of the surgical handpiece system of FIGS. 7A-7C, shown with the resilient arms of the drill bit disposed within a bore of the proximal portion of the drive cannula, the drill bit shown having a shank with a proximal end from which the resilient arms extend, a stop coupled to the shank, and an interface coupled to the shank and interposed between the stop and the proximal end.
Figure 7E:
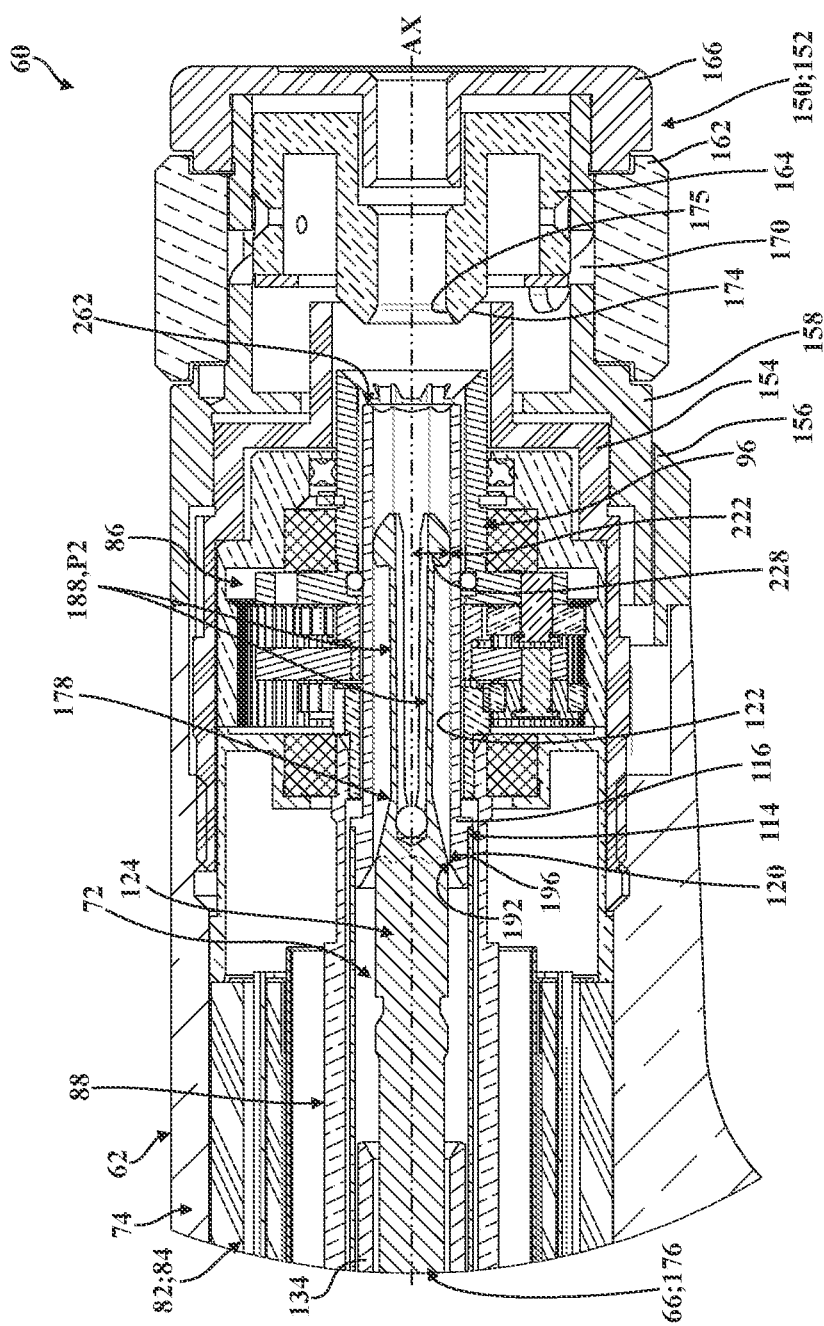
FIG. 7E is another enlarged detail view of the surgical handpiece system of FIGS. 7A-7D, shown with the resilient arms of the drill bit disposed further within the bore of the proximal portion of the drive cannula, and with the interface of the drill bit positioned within the bore of the proximal portion of the drive cannula adjacent to the seat surface.
Figure 7F:
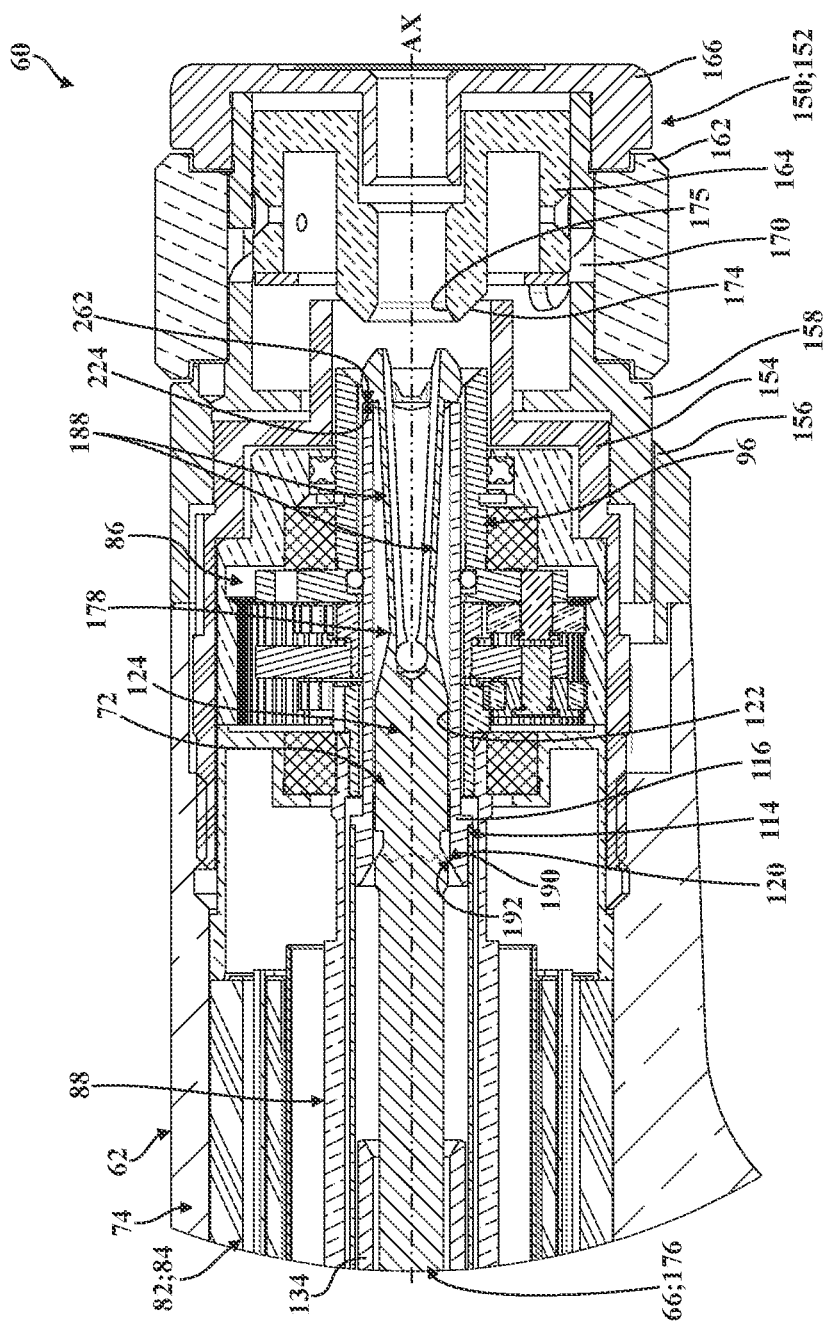
FIG. 7F is another enlarged detail view of the surgical handpiece system of FIGS. 7A-7E, shown with the resilient arms of the drill bit deflected resiliently away from one another with each resilient arm having a retention surface abutting a lock surface of the proximal portion of the drive cannula, and shown with the stop of the drill bit abutting the seat surface of the proximal portion of the drive cannula to retain the interface within the bore.

FIGS. 7A-7I sequentially illustrate certain steps involved with attaching the drill bit 66 to the surgical handpiece assembly 22 and then releasing the drill bit 66 from the surgical handpiece assembly 66. FIG. 7A depicts various portions of the surgical handpiece assembly 62 with the drill bit 66 completely removed.

In FIG. 7B, the insertion portion 72 of the drill bit 66 is shown partially inserted into the surgical handpiece assembly 62. While not depicted in this view, it will be appreciated that inserting the drill bit 66 may advantageously be performed with the tip protector 68 removably attached to the cutting tip portion 70, such as to permit relative rotation between the drill bit 66 and the handle 266 as described above. Here in FIG. 7B, the resilient arms 188 are shown extending away from the proximal end 178 of the shank 176 such that the arm ends 200 are disposed axially between the depth cannula 134 and the distal end 254 of the proximal portion 116 of the drive cannula 114. The resilient arms 188 are shown arranged in the first position P1.

In FIG. 7C, the drill bit 66 is advanced further into the surgical handpiece assembly 62 (compare with FIG. 7B). Here, the ramp surfaces 230 of the resilient arms 188 are shown abutting against the seat surface 192 of the proximal portion 116 of the drive cannula 114, deflecting toward the axis AX.

In FIG. 7D, the drill bit 66 is advanced even further into the surgical handpiece assembly 62 (compare with FIG. 7C). Here, the outer arm surfaces 222 of the resilient arms 188 are shown in contact with the bore 122 of the proximal portion 116 of the drive cannula 114 which, as will be appreciated from the previous description of the aligning element 242, means that the interface 124 of the drill bit 66 is indexed relative to the bore 122 of the proximal portion 116 of the drive cannula 114 without any engagement, contact, or abutment occurring between the interface 124 and the bore 122. Furthermore, the resilient arms 188 are shown arranged in the second position P2 in FIG. 7D.

In FIG. 7E, the drill bit 66 is advanced still further into the surgical handpiece assembly 62 (compare with FIG. 7D). Here, the proximal interface end 196 of the interface 124 has entered the bore 122 of the proximal portion 116 of the drive cannula 114. Here too in FIG. 7E, the resilient arms 188 are shown arranged in the second position P2.

In FIG. 7F, the drill bit 66 is advanced fully into the surgical handpiece assembly 62 (compare with FIG. 7E). Here, the resilient arms 188 are shown deflected back away from the axis AX, away from the second position P2 toward (or, in some configurations, at) the first position P1. As noted above, this brings the retention surfaces 224 of the resilient arms 188 into abutment with the lock surfaces 262 provided at the proximal end 256 of the proximal portion 116 of the drive cannula 114, which prevents the drill bit 66 from moving distally along the axis AX. Moreover, abutment between the stop surface 190 of the drill bit 66 and the seat surface 192 of the proximal portion 116 of the drive cannula 114 prevents the drill bit 66 from advancing axially further into the surgical handpiece assembly 62. Thus, the drill bit 66 is axially locked to the drive cannula 114 in FIG. 7F. Furthermore, because the interface 124 of the drill bit 66 is disposed within the bore 122 of the proximal portion 116 of the drive cannula 114, the drill bit 66 is also rotationally locked to the drive cannula 114. As such, when in the orientation depicted in FIG. 7F, the surgical handpiece assembly 62 can be utilized to rotate the drill bit 66.

Figure 7G:
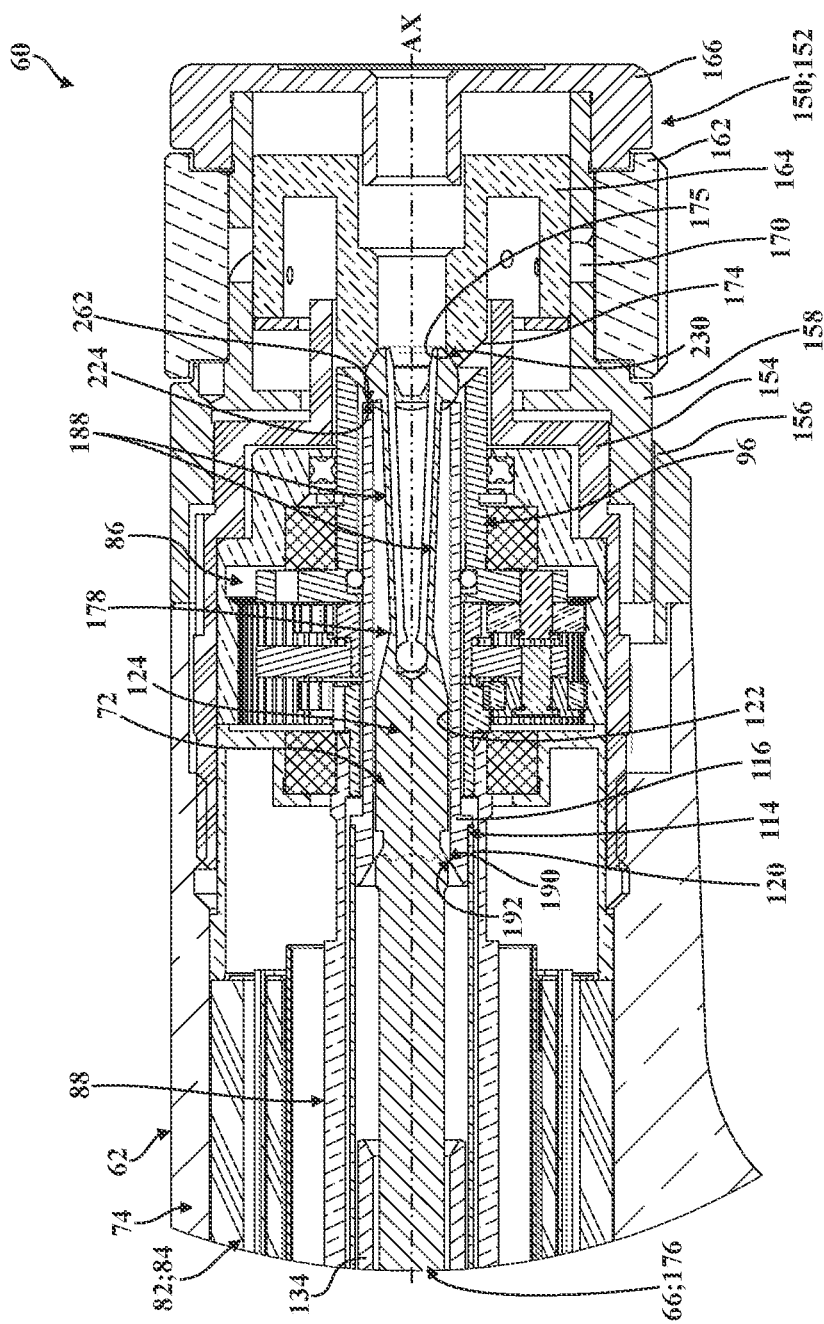
FIG. 7G is another enlarged detail view of the surgical handpiece system of FIGS. 7A-7F, shown with a release member of the release assembly engaging against the resilient arms and deflecting the resilient arms toward one another to facilitate moving the retention surfaces of the resilient arms out of abutment with the lock surfaces of the proximal portion of the drive cannula.

In FIG. 7G, the drill bit 66 is disposed in the same axial position as is illustrated in FIG. 7F, but the resilient arms 188 are shown deflecting back toward the axis AX to facilitate removing the drill bit 66 from the surgical handpiece assembly 62 via actuation of the release assembly 150 (compare with FIG. 7F). More specifically, in FIG. 7G, rotation of the collar 162 of the release assembly 150 has resulted in axial translation of the release member 164 to bring the release surface 175 of the actuating element 174 into abutment with the ramp surfaces 230 of the resilient arms 188, thereby deflecting the resilient arms 188 back toward the axis AX.

Figure 7H:
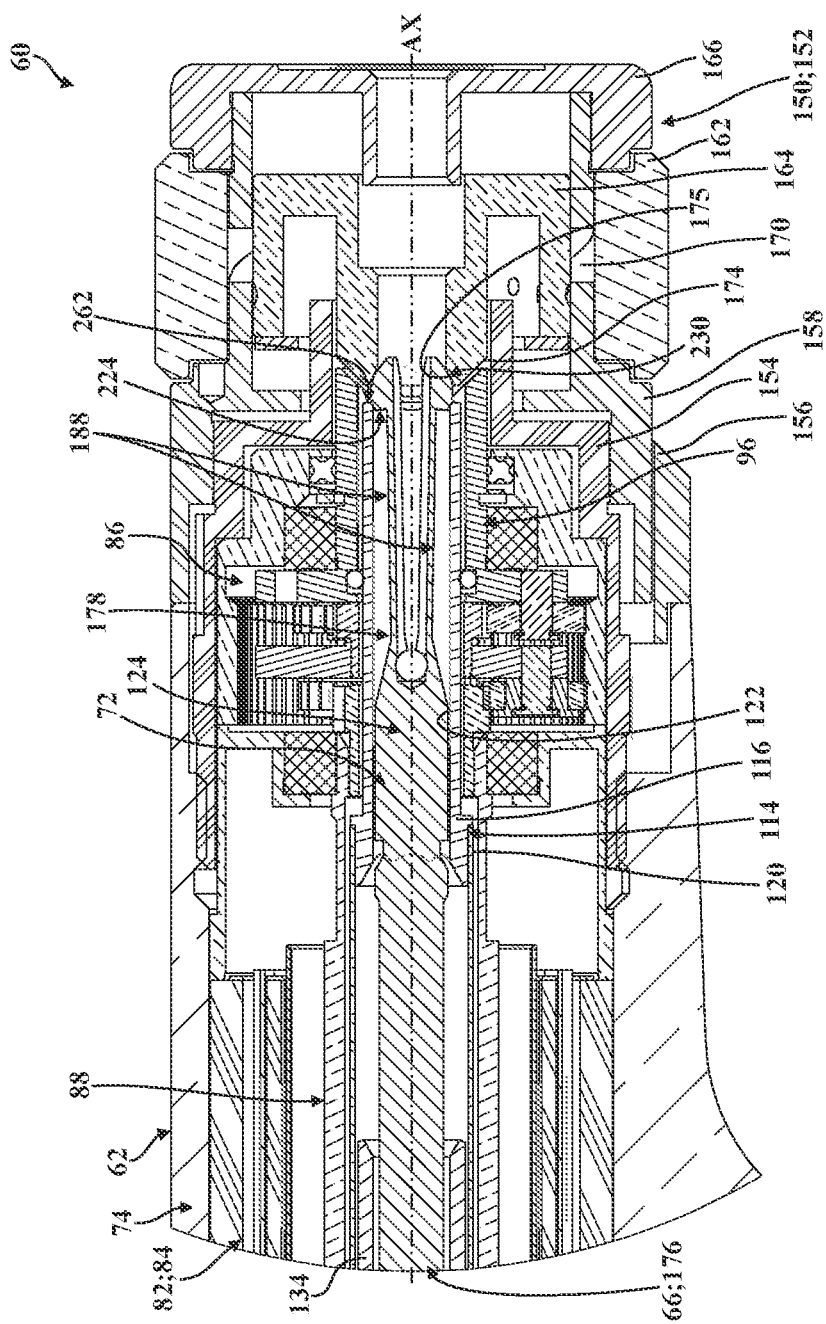
FIG. 7H is another enlarged detail view of the surgical handpiece system of FIGS. 7A-7G, shown with the release member of the release assembly further engaging against and deflecting the resilient arms with the retention surfaces out of abutment with the lock surfaces of the proximal portion of the drive cannula.

In FIG. 7H, the drill bit 66 has been pushed slightly forward (distally) from the axial positions illustrated in FIGS. 7F-7G and the resilient arms 188 are shown deflected even further back toward the axis AX (compare with FIG. 7G). Here in FIG. 7H, further rotation of the collar 162 of the release assembly 150 has resulted in additional axial translation of the release member 164, thereby causing the resilient arms 188 to deflect even further back toward the axis AX to bring the retention surfaces 224 of the resilient arms 188 back out of abutment with the lock surfaces 262 provided at the proximal end 256 of the proximal portion 116 of the drive cannula 114 to facilitate removing the drill bit 66 from the surgical handpiece assembly 62.

Figure 7I:
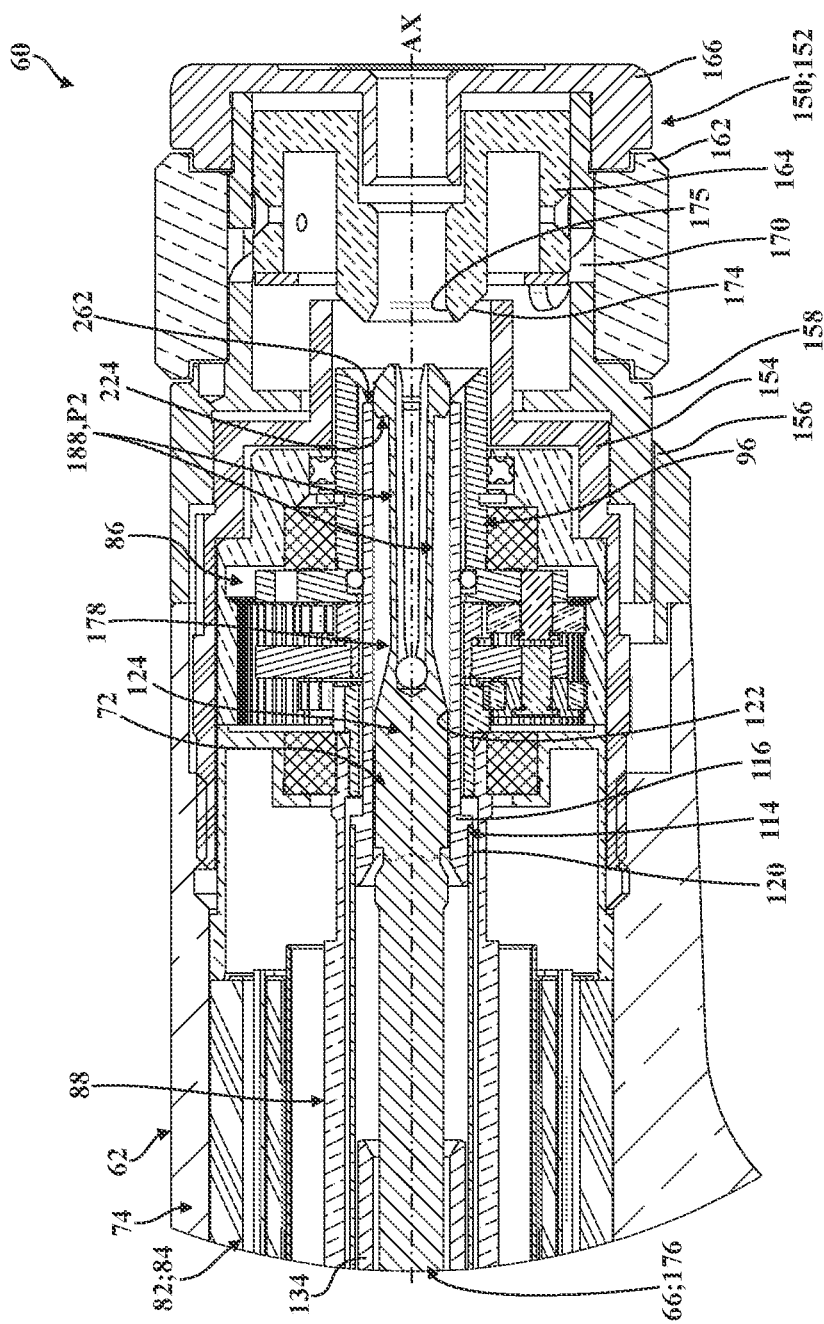
FIG. 7I is another enlarged detail view of the surgical handpiece system of FIGS. 7A-7H, shown with the release member of the release assembly out of engagement with the resilient arms, and shown with the resilient arms disposed within the bore of the proximal portion of the drive cannula adjacent to and out of contact with the lock surfaces.

In FIG. 7I, the drill bit 66 is retracted axially after having been released via the release assembly 150 (compare with FIG. 7H). Here in FIG. 7I, the resilient arms 188 are shown arranged in the second position P2 and are disposed adjacent to the proximal end 256 of the proximal portion 116 of the drive cannula 114. Here in FIG. 7I, because the retention surfaces 224 of the resilient arms 188 are out of abutment with the lock surfaces 262 of the proximal portion 116 of the drive cannula 114, the drill bit 66 can be removed from the surgical handpiece assembly 62. In some configurations, the potential energy stored in the in the resilient arms 188 when deflected toward the second position P2 and out of abutment with the lock surfaces 262 will force (i.e. "kick") the drill bit distally forward from the axial positions shown in FIGS. 7F-7G. This feature is particularly advantageous as the drill bit 66 may be released via the release assembly 150 by the user with a single hand. In other words, the user need not grasp or otherwise affect movement of the drill bit 66 directly with one hand while operating the release assembly 150 to disengage the drill bit 66 from the drive cannula 114 with the other hand.

In this manner, the end effector assembly 64 described herein and illustrated throughout the drawings affords significant advantages in connection with facilitating releasable attachment to surgical handpiece assembly 62. Specifically, it will be appreciated that the drill bit 66 of the present disclosure can be reliably attached to the surgical handpiece assembly 62 in a simple, efficient manner by guiding the insertion portion 72 into the proximal portion 116 of the drive cannula 114 and then applying force along the axis AX. Moreover, it will be appreciated that the tip protector 68 described herein affords additional advantages when used in connection with the drill bit 66 by allowing the user to safely handle and position the drill bit 66 while guiding the insertion portion 72 into the proximal portion 116 of the drive cannula 114 and applying force along the axis AX. Furthermore, the self-aligning features of the end effector assembly 64 described herein, including without limitation the aligning element 242 of the resilient arms 188 and the relative rotation afforded between the drill bit 66 and the handle 266 of the tip protector 68, further promote improved user experience and efficient, reliable attachment to the surgical handpiece assembly 62.

As noted above, the distal portion 118 of the drive cannula 114 may comprise the distal protrusion 126, which is provided to facilitate transmitting rotational torque when the surgical handpiece assembly 62 is utilized in connection with other applications besides rotating the drill bit 66. More specifically, the illustrated drive cannula 114 is configured such that the surgical handpiece assembly 62 can rotate, drive, or otherwise actuate a number of different types of surgical attachment modules, tools, end effectors, and the like, which can be configured to engage and rotate concurrently with the distal protrusion 126 of the distal portion 118 of the drive cannula 114. It will be appreciated that this configuration allows the same surgical handpiece assembly 62 to be utilized in a broad number of medical and/or surgical procedure, such as a drill procedure and a reaming procedure, a drill procedure and a sawing procedure, or a drilling procedure and a wire drive procedure. For instance, the distal portion 118 of the drive cannula 114 may be employed to assist in operation of and attachment to one of a sagittal saw assembly, a reciprocating saw assembly, a drill chuck assembly, a reamer assembly, a wire driving assembly, and a burring assembly.

Figure 47:
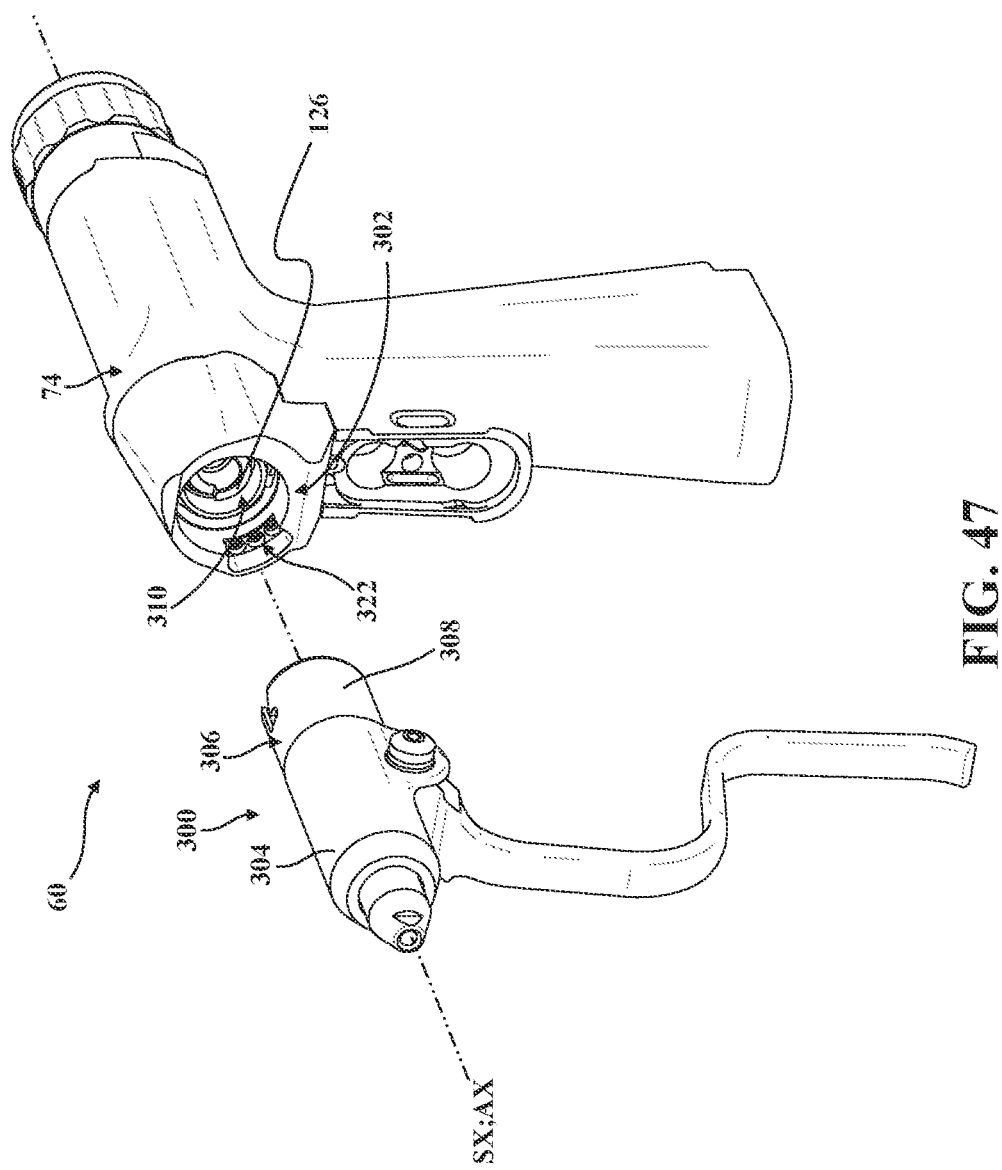
FIG. 47 is a perspective view of a surgical attachment module adjacent a surgical handpiece assembly.
Figure 48:
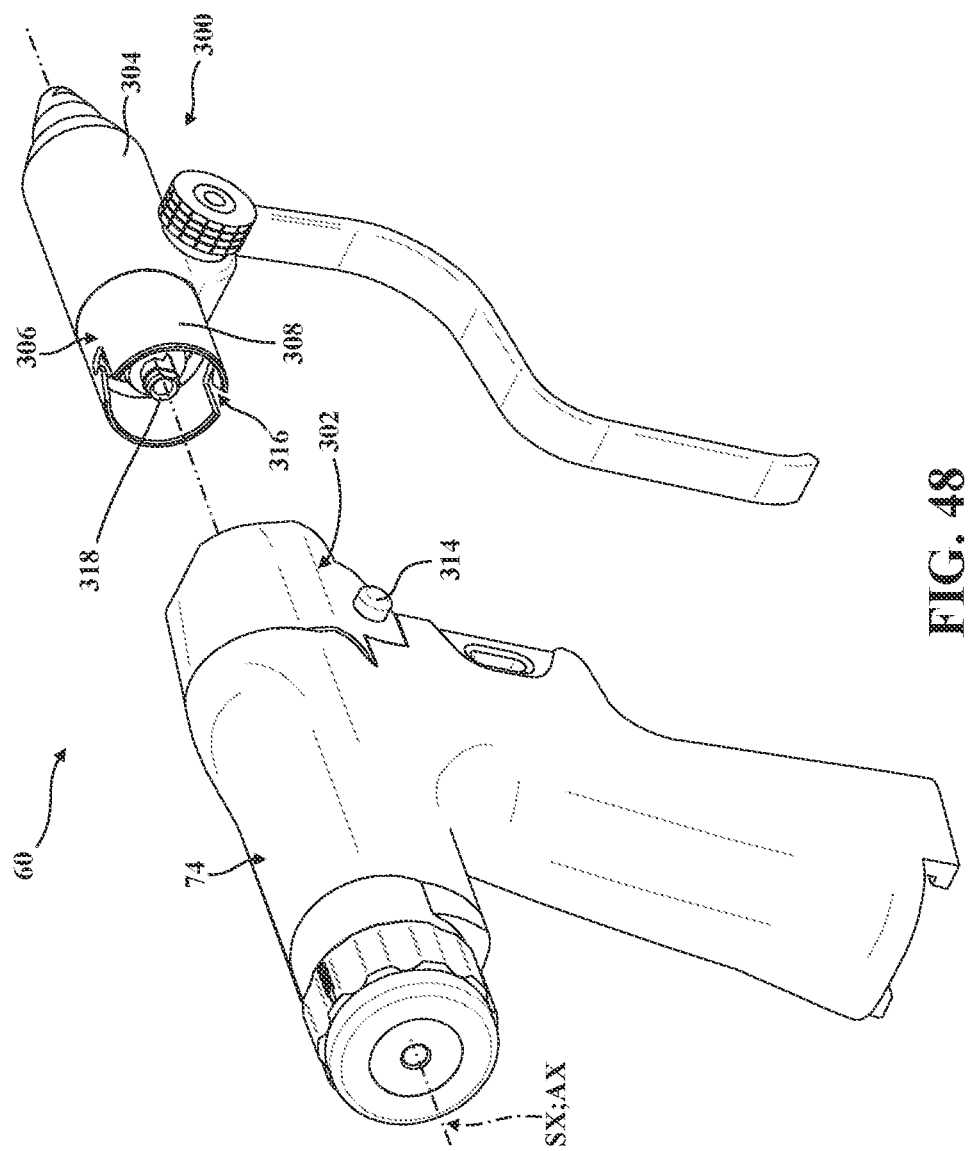
FIG. 48 is another perspective view of the surgical attachment module adjacent the surgical handpiece assembly of FIG. 47.

As shown in FIGS. 47-51, one exemplary surgical attachment module 300 is illustrated being configured for removable attachment to the surgical handpiece assembly 62. FIGS. 47 and 48 illustrate the surgical attachment module 300 separated from the surgical handpiece assembly 62. The handpiece housing assembly 74 comprises a handpiece coupler 302 adjacent a distal region of the housing assembly 74. The surgical attachment module 300 comprises a surgical attachment housing 304. The surgical attachment housing 304 may comprise a surgical attachment coupler 306 that is configured to be removably coupled to the handpiece coupler 302. In the illustrated configurations, the handpiece coupler 302 and the surgical attachment coupler 306 cooperate to form a bayonet coupling. The surgical attachment coupler 306 comprises a bayonet mount 308 and the handpiece coupler 302 defines a cavity 310 configured to receive the bayonet mount 308 or vice-versa. The surgical handpiece assembly 62 comprises a pin 312 coupled to a spring biased button 314 (See FIGS. 50-51) to engage with the bayonet mount 308 in the cavity 310 of the surgical handpiece assembly 62 to releasably attach the surgical attachment module 300 to the surgical handpiece assembly 62. More specifically, the bayonet mount 308 may comprise a non-linear slot 316 (See FIG. 48) such as a "J-slot" configured to receive the pin 312. When the button 314 is depressed, the pin 312 moves to a position to be received by the slot 316 of the bayonet mount 308. When the bayonet mount 308 is received in the cavity 310, the button 314 may be released to permit the pin 312 into a seat of the slot 316 for securing the bayonet mount 308 in the cavity 310 of the surgical handpiece assembly 62. In some configurations, the slot 316 is formed with a ramped surface to bias the pin 312 and apply force in opposition to the spring biased button 314 to guide the pin 312 into the slot 316 without the user depressing the button 314. When the pin 312 is in the seat of the slot 316, the bayonet mount 308, and thus the surgical attachment module 300 is in an engaged position coupled to the surgical handpiece assembly 62 and axial movement of the bayonet mount 308 and the surgical attachment housing 304 is prevented. To disengage the bayonet mount 308 from the handpiece coupler 302, the user depresses the button 314 to unseat the pin 312 from the seat of the slot 316 to permit the surgical attachment housing 304 to be moved axially away from the handpiece coupler 302. It is contemplated that the handpiece coupler 302 and the surgical attachment coupler 306 could have different arrangements or geometries so long as the handpiece coupler 302 and the surgical attachment coupler 306 cooperate to attach to one another. In other configurations, a bushing of the surgical attachment module 300 includes the bayonet mount described above.

Figure 49:
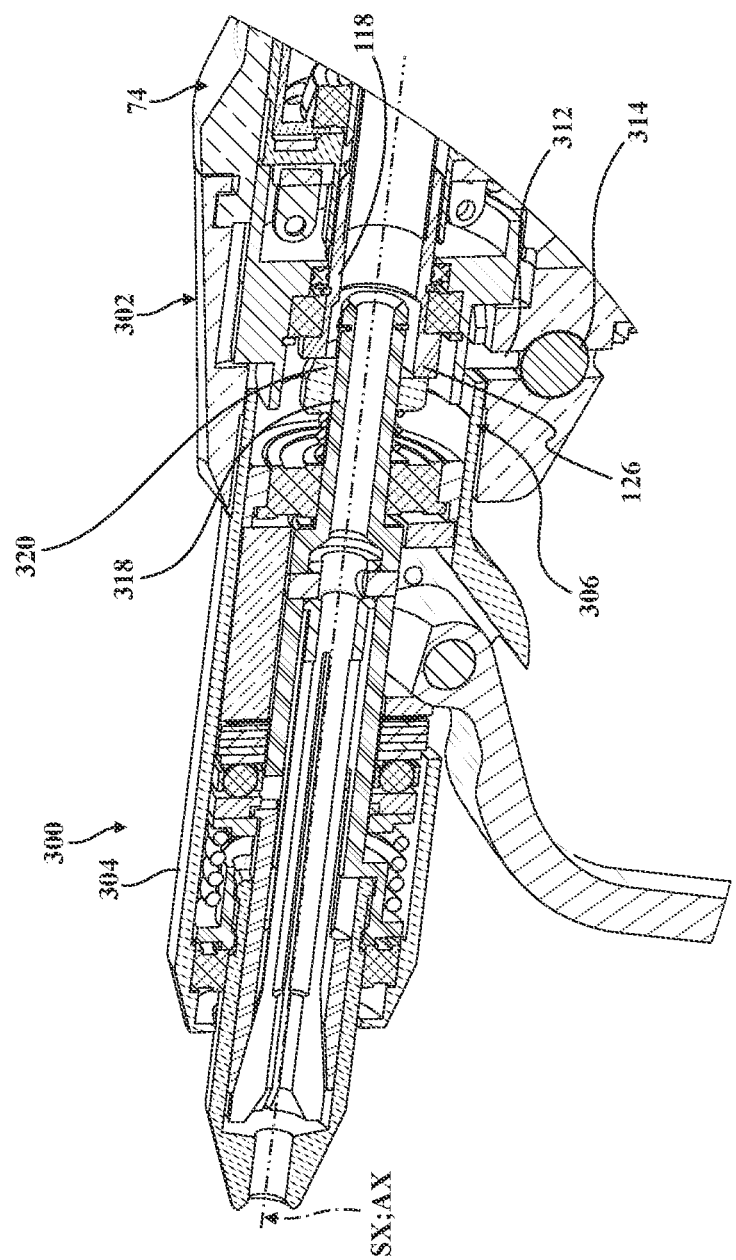
FIG. 49 is a partial isometric sectional view of the surgical attachment module coupled to the surgical handpiece assembly of FIGS. 47-48 taken generally along a longitudinal axis.

As shown in FIG. 49, the surgical attachment module 300 is in the engaged position. The surgical attachment module 300 comprises a drive shaft 318 that is rotatably coupled to the surgical attachment housing 304 and configured to rotate about a surgical attachment axis SX. The surgical attachment axis SX is aligned with the axis AX of the surgical handpiece assembly 62 when the surgical attachment module 300 is in the engaged position. When the surgical attachment module 300 is in the engaged position, the drive shaft 318 of the surgical attachment module 300 is coupled to the distal protrusion 126 and the surgical attachment module 300 is configured to receive torque from the distal protrusion 126 of the drive cannula 114. The drive shaft 318 comprises a protrusion 320 configured to couple to the distal protrusion 126 and receive torque from the distal protrusion 126 via interference coupling. It is contemplated that the drive shaft 318 could have a different arrangement or geometry so long as the drive shaft 318 engages with the distal protrusion 126 to receive torque from the distal protrusion 126. Again, while a particular geometry is described throughout this application for the drive shaft 318 and the drive cannula 114, it should be appreciated that each component may have any suitable configuration that is sufficient to transmit torque from the drive cannula 114 to the surgical attachment module 300. In the illustrated configuration, the surgical attachment module 300 comprises an output member configured to drive a surgical end effector. A linkage and/or a gear train may be coupled to the drive shaft 318 and the output member to convert torque received from the distal protrusion 126 and available at the drive shaft 318 to mechanical power available at the output member for driving the surgical end effector.

Figure 50:
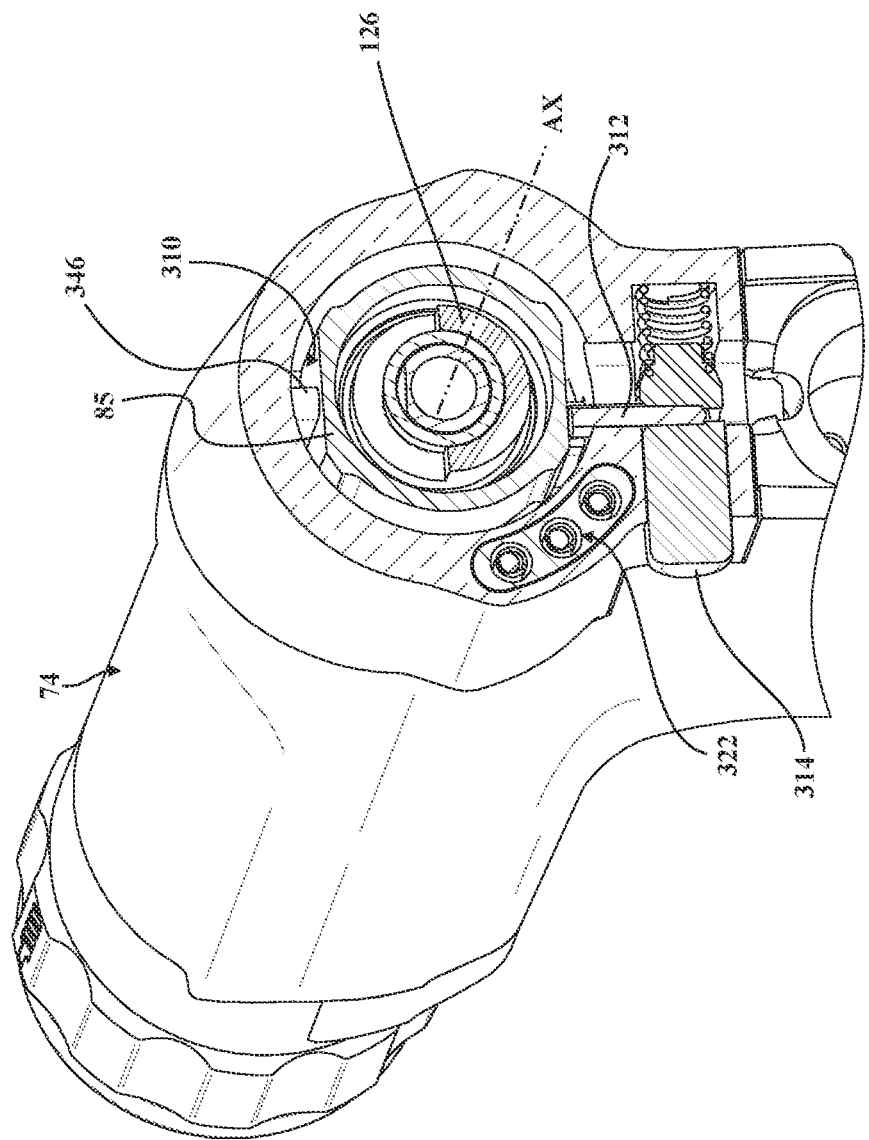
FIG. 50 is a partial isometric sectional view of the surgical handpiece assembly of FIGS. 47-49 taken generally transverse to the longitudinal axis.
Figure 51:
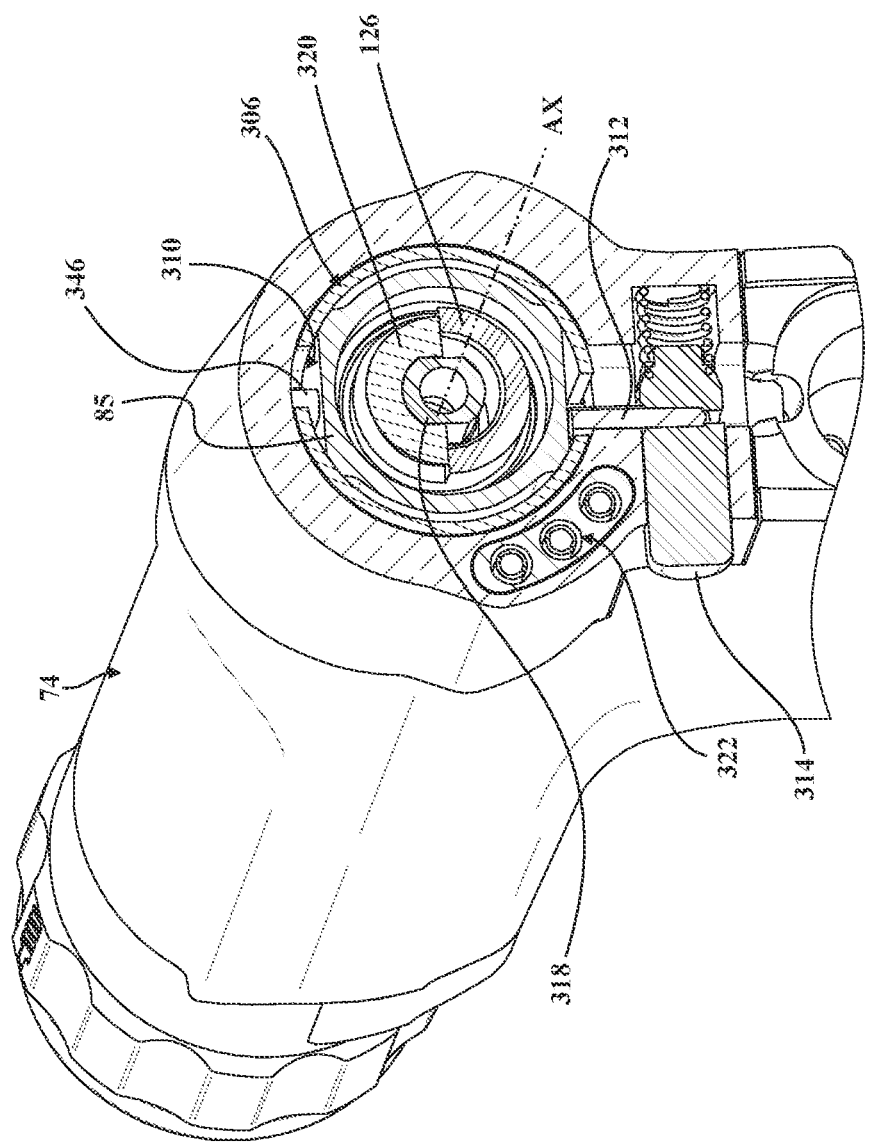
FIG. 51 is a partial isometric sectional view of the surgical attachment module coupled to the surgical handpiece assembly of FIGS. 47-50 taken generally transverse to the longitudinal axis.

As shown in FIGS. 47 and 50-51, the surgical handpiece assembly 62 comprises one or more electrical connectors 322 coupled to the power source when the surgical handpiece assembly 62 is coupled to the power source (e.g., removable battery). While the surgical attachment module 300 described above only receives mechanical power and does not receive electrical power, it is contemplated that one or more surgical attachment modules may receive both mechanical power and electrical power from the surgical handpiece assembly 62. For instance, another surgical attachment module (not illustrated) may comprise a rotary drive attachment module that comprises a light source (not shown) such that the rotary drive attachment module is configured to receive mechanical power in the form of torque through a drive shaft 318 and electrical power in the form of voltage through the electrical connections of the surgical handpiece assembly 62. In other configurations, certain surgical attachment modules may receive exclusively electrical power from the surgical handpiece when coupled thereto.

In FIGS. 47-51, the surgical attachment module 300 comprises a wire driver assembly. One such wire driver assembly is disclosed in U.S. Patent Publication No. 2017/0340374 entitled "Surgical Wire Driver Capable of Automatically Adjusting for the Diameter of the Wire or Pin Being Driven" and filed on May 15, 2017, which is hereby incorporated by reference in its entirety. It is contemplated that other surgical attachment modules having a surgical attachment coupler configured to be coupled to the handpiece coupler 302 of the surgical handpiece assembly 62 and configured to receive torque from the distal protrusion 126 of the distal portion 118 of the drive cannula 114 may also be removably attached to the surgical handpiece assembly 62.

As noted above, the surgical handpiece system 60 further comprises the measurement module 128, which is configured to releasably attach to the surgical handpiece assembly 62 to provide the surgeon with measurement functionality associated with the surgical handpiece assembly 62. This measurement module 128 can be used with the surgical handpiece assembly when the drill bit 66 is engaged with the proximal portion 116 of the drive cannula 114. The depth cannula 134 is disposed within the guide bushing 132 and is supported for translational movement along the measurement axis MX. The depth cannula 134 is at least partially disposed within the measurement housing 138. Similar to the surgical attachment module 300, the measurement module 126 comprises a measurement coupler 324, 326 that is configured to be removably coupled to the handpiece coupler 302. In some configurations (see FIGS. 52-54), the housing 138 comprises the measurement coupler 324. In other configurations (see FIGS. 55-66), the bushing 132 comprises the measurement coupler 326. In the illustrated configurations, the handpiece coupler 302 and the measurement coupler 324, 326 cooperate to form a bayonet coupling. The measurement coupler 324, 326 comprises a bayonet mount 328, 330 and the cavity 310 of the handpiece coupler 302 is configured to receive the bayonet mount 328, 330 or vice-versa. The pin 312 coupled to the spring biased button 314 (See FIGS. 50 and 54) is configured to engage with the bayonet mount 328, 330 in the cavity 310 of the surgical handpiece assembly 62 to releasably attach the measurement module 128 to the surgical handpiece assembly 62. More specifically, the bayonet mount 328, 330 may comprise a non-linear slot 332, 334 (See FIGS. 53, 56, and 64) such as a "J-slot" configured to receive the pin 312. When the button 314 is depressed, the pin 312 moves to a position to be received by the slot 332, 334 of the bayonet mount 328, 330. When the bayonet mount 328, 330 is received in the cavity 310, the button 314 may be released to permit the pin 312 to move into a seat of the slot 332, 334 for securing the bayonet mount 328, 330 in the cavity 310 of the surgical handpiece assembly 62. In some configurations, the slot 332, 334 is formed with a ramped surface to bias the pin 312 and apply force in opposition to the spring biased button 314 to guide the pin 312 into the slot 332, 334 without the user depressing the button 314. When the pin 312 is in the seat of the slot 332, 334, the bayonet mount 328, 330, and thus the measurement module 128 is in an engaged position coupled to the surgical handpiece assembly 62 and axial movement of the bayonet mount 328, 330 and the measurement housing 138 is prevented. To disengage the bayonet mount 328, 330 from the handpiece coupler 302, the user depresses the button 314 to unseat the pin 312 from the seat of the slot 332, 334 to permit the measurement module 128 to be moved axially away from the handpiece coupler 302. It is contemplated that the handpiece coupler 302 and the measurement coupler 324, 326 could have different arrangements or geometries so long as the handpiece coupler 302 and the measurement coupler 324, 326 cooperate to attach to one another. The surgical handpiece system 60 presents an advantage in employing the same handpiece coupler 302 to interchangeably attach both the surgical attachment module 300 (attachment that receives mechanical power from the surgical handpiece assembly 62) and a measurement module 128 to the surgical handpiece assembly 62 (attachment that does not receive mechanical power from the surgical handpiece assembly 62) without having to buy two surgical handpieces—one dedicated to the measurement function and others dedicated to cutting/drilling tissue.

As best shown in FIGS. 4 and 6, the depth cannula 134 comprises an internal surface defining a bore 338. The bore 338 of the depth cannula 134 is sized to at least partially receive the drill bit 66 when the measurement coupler is attached to the handpiece coupler 302. The depth cannula 134 is configured to slide relative to the drill bit 66 to assist in performing measurement functions associated with the surgical handpiece assembly 62. In certain configurations, the drive cannula 114, the depth cannula 134, and the drill bit 66 are arranged to be concentric when the drill bit 66 is in the engaged position and the measurement module 128 is coupled to the surgical handpiece assembly 62. The depth cannula 134 is sized to be at least partially received within the bore 122 of the distal portion 118 of the drive cannula 114 when the drill bit 66 is in the engaged position and the measurement housing 138 is coupled to the handpiece housing assembly 74. The concentricity of the depth cannula 134 to the drill bit 66 along the measurement axis MX and the axis of the handpiece AX and the arrangement of the depth cannula 134 configured to be received in the drive cannula 114, which is situated in the surgical handpiece assembly 62, is beneficial in providing increased visibility of a surgical site to a user operating the surgical system 60 with the measurement module 128. The construction of the surgical handpiece described in International Patent Publ. No. WO 2017/040783 (Application No. PCT/US2016/049899) entitled "Powered Surgical Drill with Integral Depth Gauge That Includes a Probe That Slides Over the Drill Bit" filed on Jan. 9, 2016, which is hereby incorporated by reference for all that it discloses. In certain embodiments, the depth cannula 134 may comprise a depth extension that is not concentric with the bore of the drive cannula 114.

Figure 52:
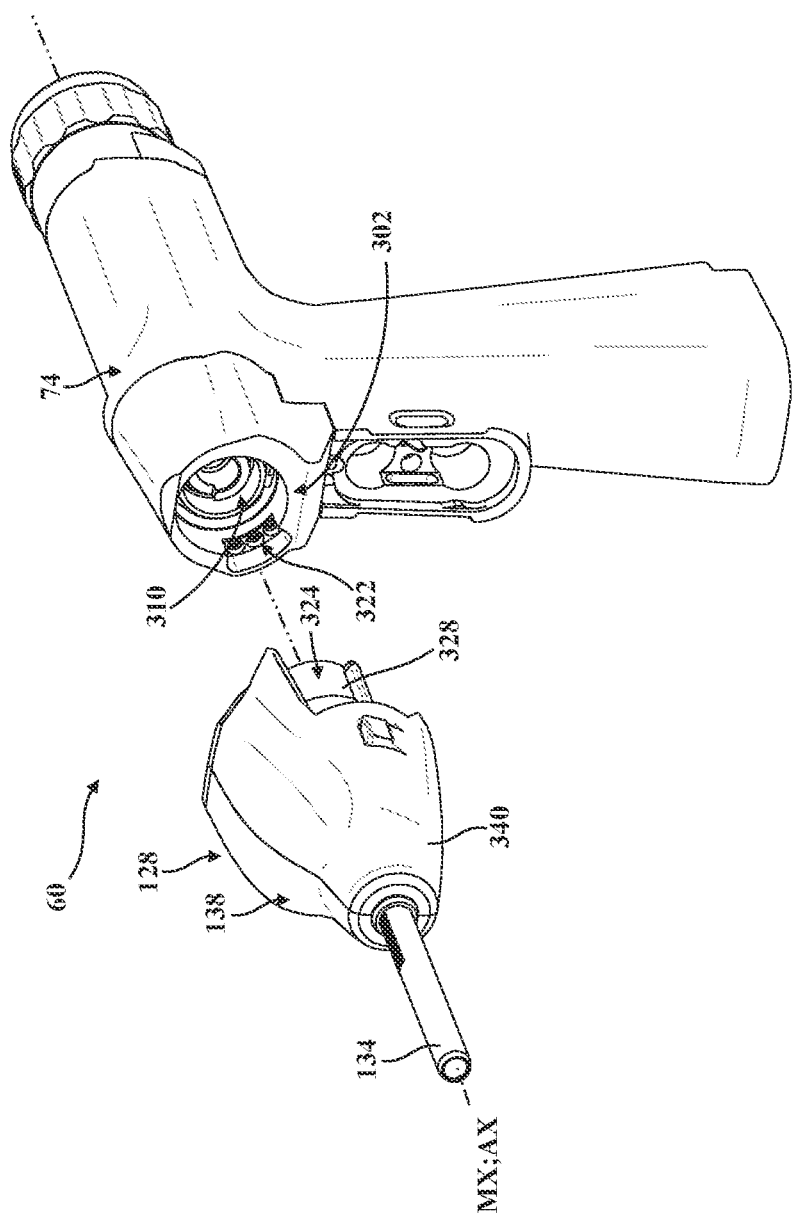
FIG. 52 is a perspective view of a measurement module adjacent a surgical handpiece assembly.
Figure 53:
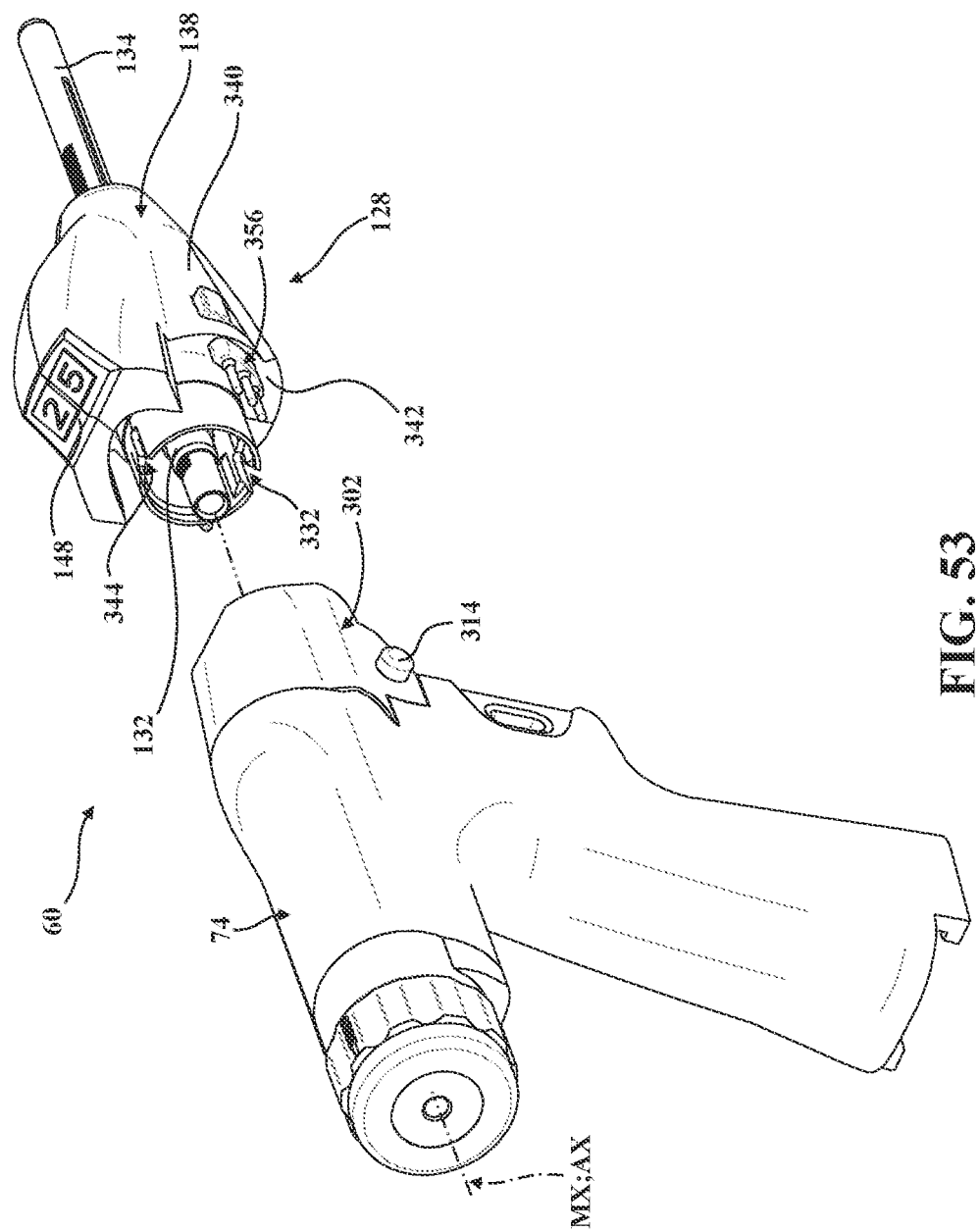
FIG. 53 is another perspective view of the measurement module adjacent the surgical handpiece assembly of FIG. 52.
Figure 54:
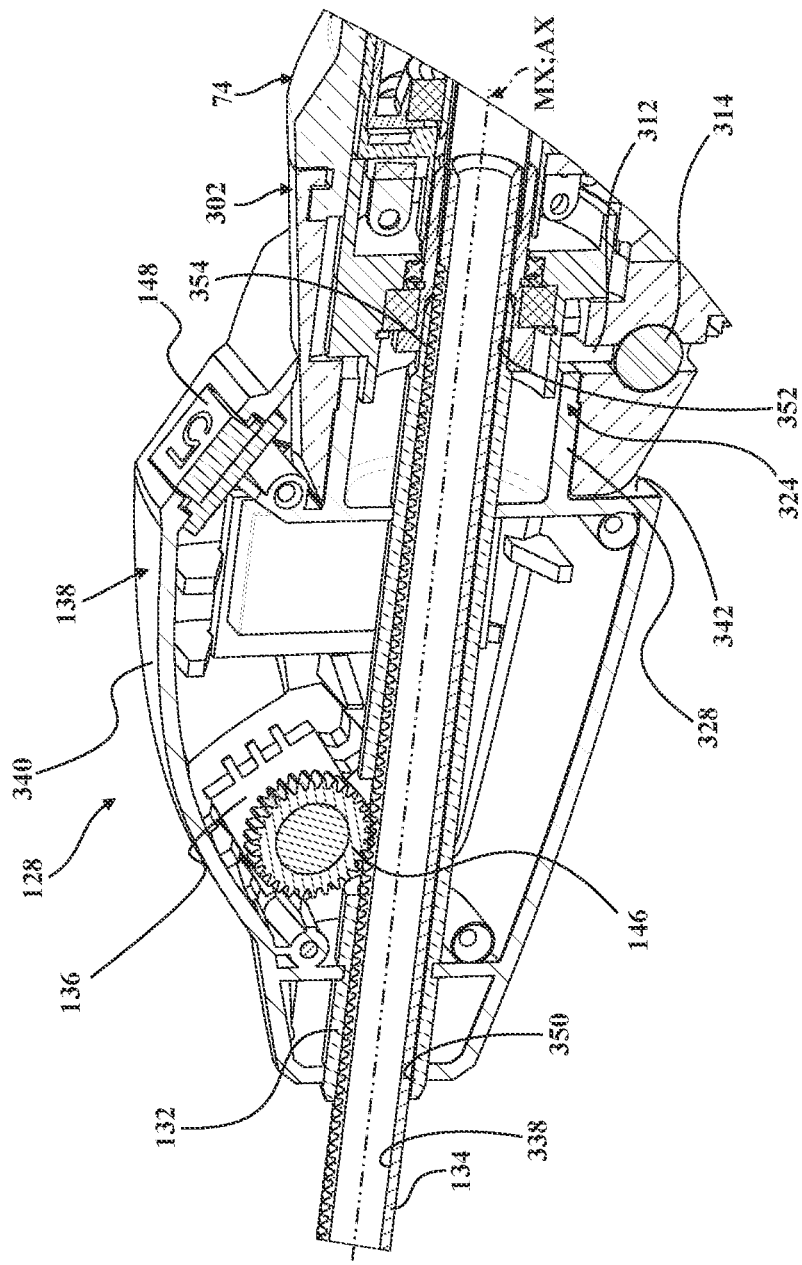
FIG. 54 is a partial isometric sectional view of the measurement module coupled to the surgical handpiece assembly of FIGS. 52-53 taken generally along a longitudinal axis.
Figure 55:
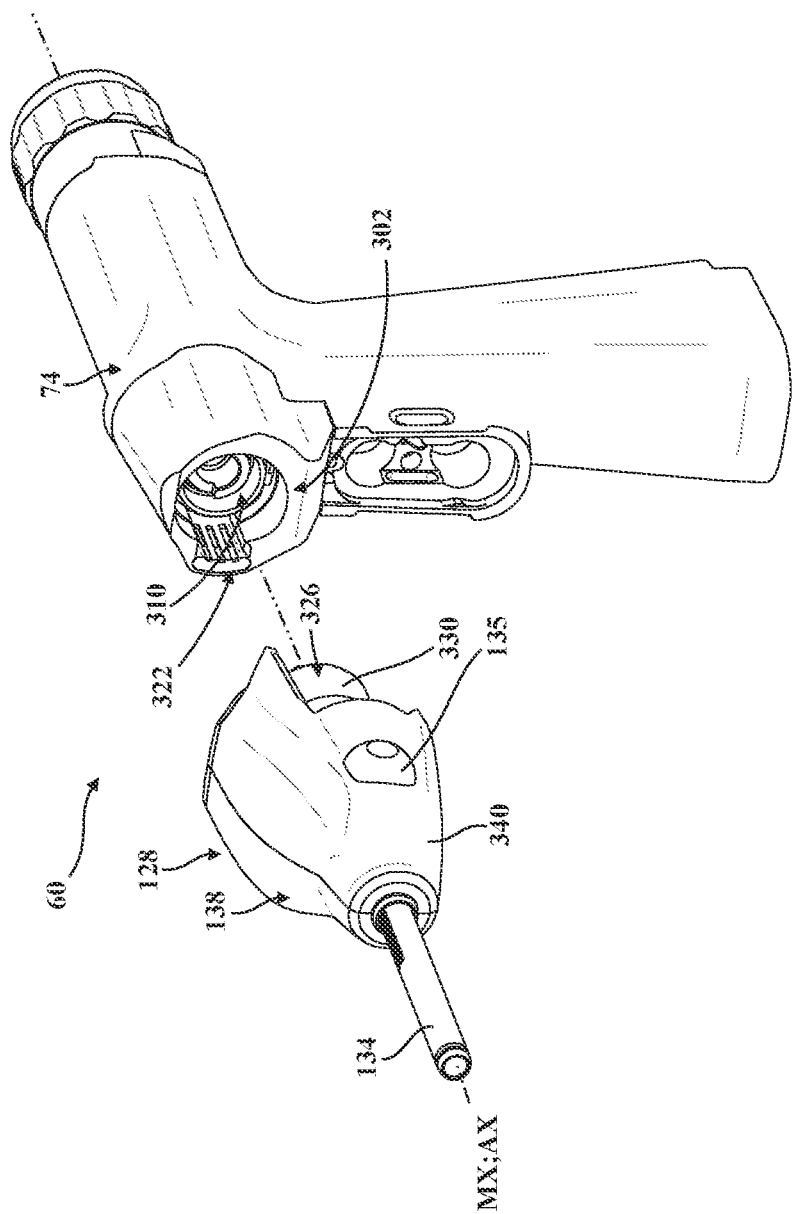
FIG. 55 is a perspective view of another measurement module adjacent a surgical handpiece assembly.

FIGS. 52-54 show the surgical handpiece system 60 in accordance with an exemplary configuration of the measurement module 128. In at least some respects, the configuration shown in FIGS. 52-54 is the same as the configuration previously described with like numbers indicating like components. In the configurations shown in FIGS. 52-54, the measurement housing 138 comprises the measurement coupler 324 as described below. It should be appreciated that any features that are described in FIGS. 47-51 may be included in the embodiment described in FIGS. 52-54 and vice-versa.

As shown in FIG. 53, the measurement housing 138 comprises a body portion 340 having a proximal region with a proximal surface 342 configured to face the surgical handpiece assembly 62 when the measurement module 128 is coupled to the surgical handpiece assembly 62. The measurement housing 138 may comprise any suitable material, such as plastic or metal. Additionally, the measurement housing 138 may be formed from two complementary shell components.

The measurement housing 138 comprises the measurement coupler 324. The measurement coupler 324 extends proximally from the proximal surface 342. As noted above and illustrated in the configuration shown in FIG. 53, the measurement coupler 324 comprises the bayonet mount 328. The bayonet mount 328 comprises the "J-slot" 332 as described above and another slot 344 opposite the "J-slot" for receiving a projection 346 of the motor housing 85 (See FIG. 50) to assist in radial alignment relative to the handpiece coupler 302.

As shown in FIG. 54, the measurement module 128 also comprises the bushing 132 at least partially received in the measurement housing 138 and at least partially surrounding the depth cannula 134 between a proximal end and a distal end of the bushing 132. The proximal end of the bushing 132 extends beyond the proximal surface 342 of the measurement housing 138 in certain configurations. In some configurations where a bayonet mount 328 is employed such as those illustrated in FIGS. 53 and 54, the bayonet mount 328 comprises a bore 348 and the bushing 132 extends through the proximal surface 342 of the measurement housing 138 within the bore 348 of the bayonet mount 328. The bushing 132 comprises an internal surface defining a bore 350. The bore 350 of the bushing 132 is concentric to the measurement axis MX, with the bore 350 of the bushing 132 surrounding the depth cannula 134. The bushing 132 is configured to be partially received by the bore 352 of the distal portion 118 of the drive cannula 114 when the measurement coupler 324 is attached to the handpiece coupler 302. The bushing 132 also comprises an external surface having an alignment portion 354 adjacent the proximal end of the bushing 132.

The alignment portion 354 of the bushing 132 has an outer diameter sized to approximate an inner diameter of the bore 352 of the distal portion 118 of the drive cannula 114 to align the measurement axis MX to the axis AX of the handpiece. In other words, the alignment portion 354 functions to pilot the bushing 132 into the bore 352 of the distal portion 118 of the drive cannula 114. In some configurations, the alignment portion 354 tapers toward the measurement axis MX distally to proximally to assist in alignment. Ensuring proper alignment of the measurement axis MX to the axis AX of the handpiece, i.e., axis of the drive cannula 114, mitigates binding that may otherwise occur between the depth cannula 134, the drive cannula 114, and the drill bit 66 when the measurement module 128 is coupled to the surgical handpiece assembly 62. Binding may be defined as undesired friction between the depth cannula 134 and at least one of the drive cannula 114 and drill bit 66 that may result in restriction of axial movement of the depth cannula 114 relative to the drive cannula 114 and the drill bit 66 along the measurement axis MX. This binding may impede prompt distal movement of the depth cannula 134 when the drill bit 66 is retracted. More specifically, if the binding forces are too great, then a biasing mechanism (described below) associated with the depth cannula 134 may not be able to cause the depth cannula 134 to maintain engagement with the bone surface or plate surface, and a controller of the measurement module 128 may not be able to accurately determine acceleration, positive or negative, of the depth cannula 134 when the surgical handpiece assembly 62 is moved proximally. Aligning the bushing 132 directly to the drive cannula 114 creates a part-to-part alignment. One benefit of using part-to-part alignment is mitigating misalignment that could be attributable to a tolerance stack-up.

As shown in FIG. 53, the measurement housing 138 may comprise an electrical connector 356 configured to engage the electrical connector 322 of the surgical handpiece assembly 62 to transmit electrical power between the surgical handpiece assembly 62 and the measurement module 128 when the handpiece coupler 302 is coupled to the measurement coupler 324. In the configuration illustrated in FIG. 53, the electrical connector 356 of the measurement module 128 comprises two or three electrical pins and the electrical connector 322 of the surgical handpiece assembly 62 comprises two or three corresponding pin receptacles configured to receive the electrical pins when the measurement module 128 is coupled to the surgical handpiece assembly 62. The three electrical pins extend from the proximal surface 342 of the body portion 340 of the measurement housing 138 and are spaced radially from the bushing. More specifically, the group of three electrical pins is arranged to be spaced from the slots 332, 344 of the bayonet mount 328 at radially equal distances between the slots 332, 344. The three electrical pins comprise an electrical pin for power, an electrical pin for ground, and an electrical pin for data signal transfer. The electrical pin for signal transfer could be used for communication and control between the measurement module 128 and the surgical handpiece assembly 62. In some configurations electrical connector 356 of the measurement module 128 and the electrical connector 322 of surgical handpiece assembly 62 comprise fewer than three pins and pin receptacles, respectively. In other configurations, the measurement module 128 and surgical handpiece assembly 62 comprise more or fewer than three pins and pin receptacles, respectively. The electrical connector 356 of the measurement module 128 are configured to receive electrical power from the surgical handpiece assembly 62. The electrical connector 356 of the measurement module 128 are also coupled to the displacement sensor assembly 136 and the display 148 to supply electrical power to the displacement sensor assembly 136 and the display 148 when the measurement coupler 324 is coupled to the surgical handpiece assembly 62.

FIGS. 55-66 show the surgical handpiece system 60 in accordance with another exemplary configuration of the measurement module 128. In at least some respects the configuration shown in FIGS. 55-66 is the same as the configuration previously described with like numbers indicating like components. In the configurations shown in FIGS. 55-66, the bushing 132 comprises the measurement coupler 326 as described below. Again, any of the features described above with respect to the other embodiments of the measurement module 128 can be used in conjunction with the instant embodiment, and vice-versa. For example, the structure of the electrical connectors 322, 356 described above can be used with any construction of the measurement module 128.

Figure 56:
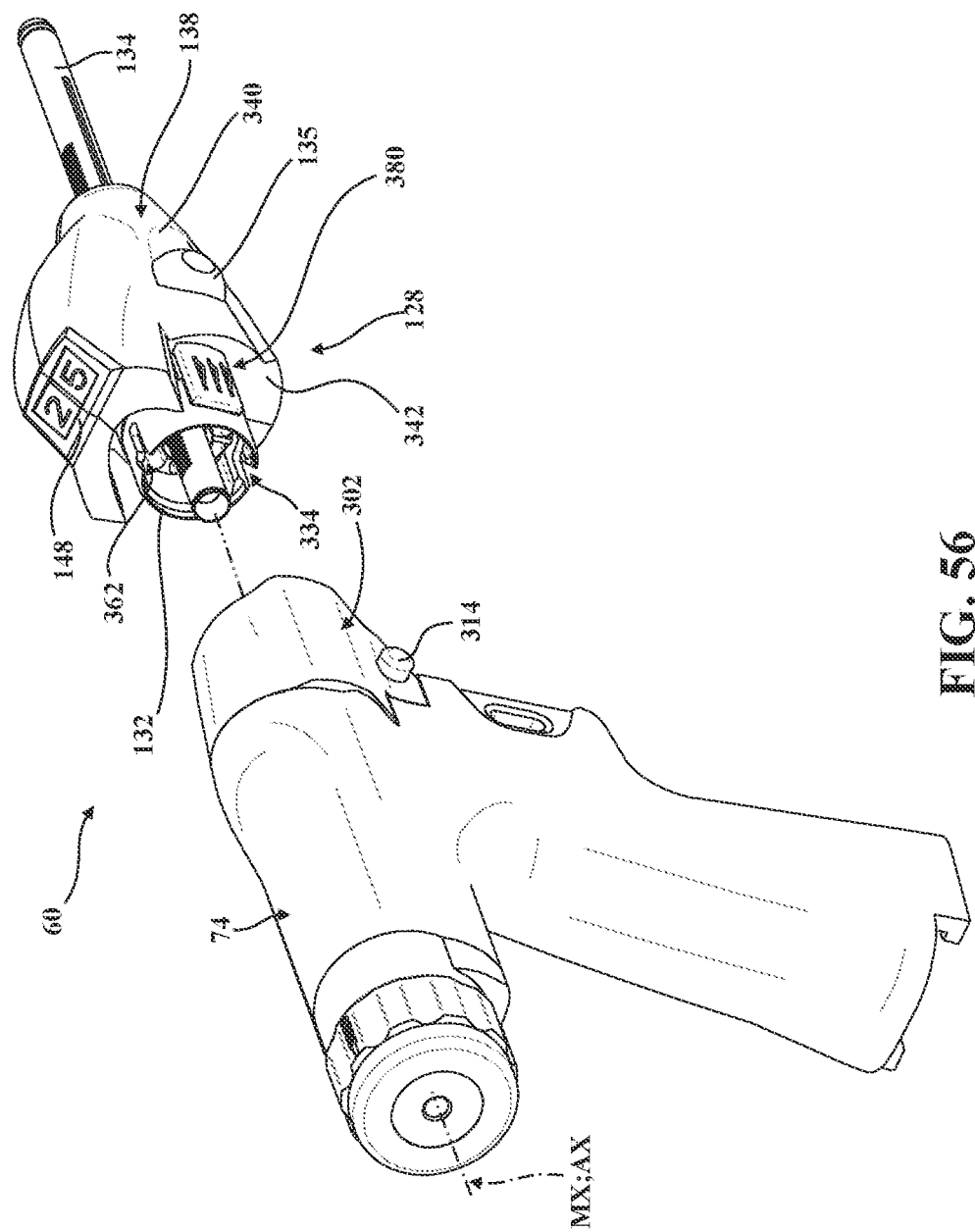
FIG. 56 is another perspective view of the measurement module adjacent the surgical handpiece assembly of FIG. 55.

As shown in FIG. 56, the measurement housing 138 comprises the body portion 340 having a proximal region with a proximal surface 342 configured to face the surgical handpiece assembly 62 when the measurement module 128 is coupled to the surgical handpiece assembly 62.

Figure 57:
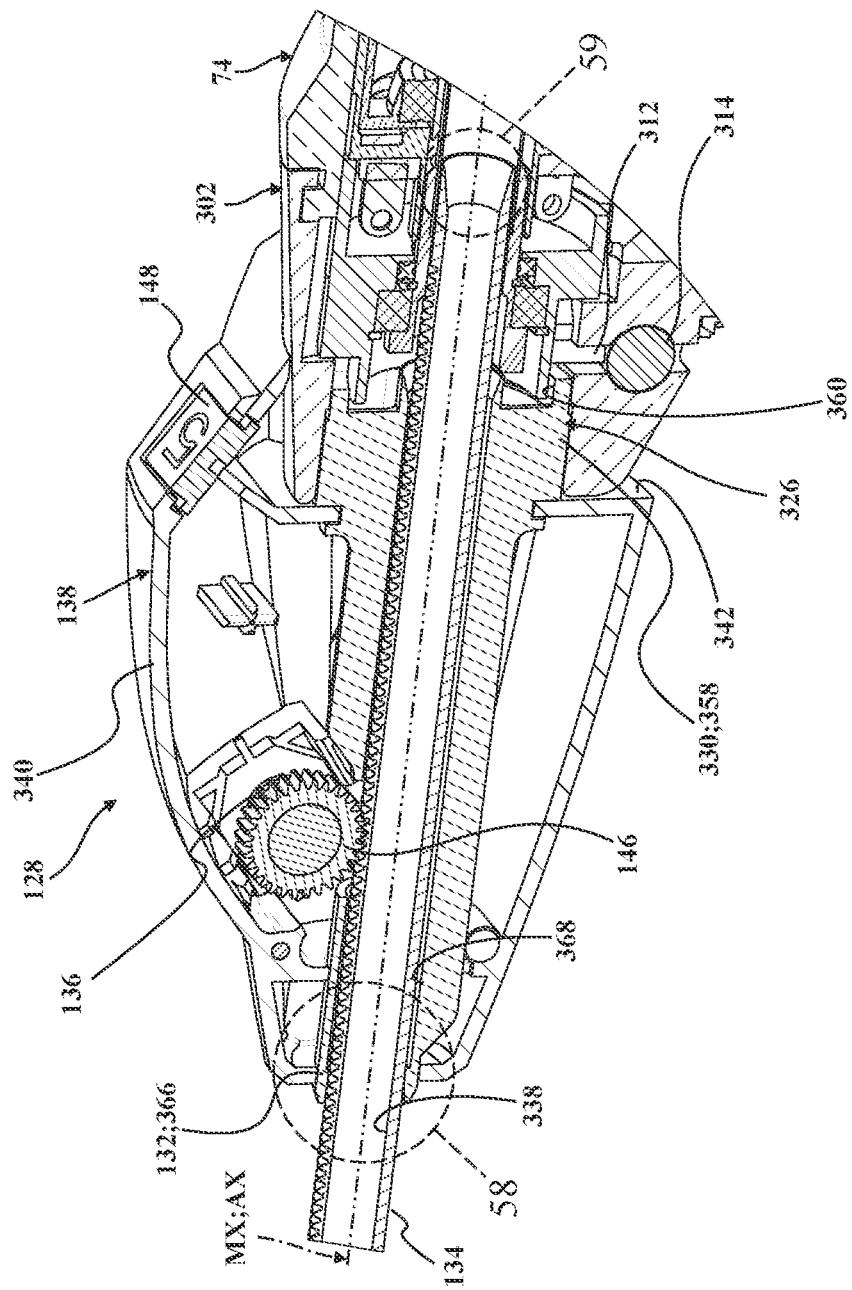
FIG. 57 is a partial isometric sectional view of the measurement module coupled to the surgical handpiece assembly of FIGS. 55-56 taken generally along a longitudinal axis.

As shown in FIG. 57, the measurement module 128 comprises the bushing 132 partially received in the measurement housing 138. The bushing 132 extends along the measurement axis MX between a proximal end protruding beyond the proximal surface 342 of the measurement housing 138 and a distal end opposite the proximal end. The bushing 132 comprises a proximal portion 358 adjacent the proximal end comprising a bore 360 having a first inner diameter. In the configuration shown in FIG. 57, the proximal portion 358 of the bushing 132 comprises the measurement coupler 326. As noted above and illustrated in the configuration shown in FIG. 57, the measurement coupler 326 may comprise the bayonet mount 330. The bayonet mount 330 comprises the "J-slot" 334 as described above and another slot 362 opposite the "J-slot" for receiving a projection 364 of the motor housing 85 (see FIG. 60) to assist in radial alignment relative to the handpiece coupler 302.

The proximal portion 358 of the bushing 132 is configured to abut the motor housing 85 (See FIGS. 50 and 51). The proximal portion 358 of the bushing 132 abuts the motor housing 85 to assist in alignment of the measurement axis MX to the handpiece axis AX. The alignment of the measurement axis MX to the axis AX of the handpiece mitigates binding that may otherwise occur between the depth cannula 134, the drive cannula 114, and the drill bit 66 when the measurement module 128 is coupled to the surgical handpiece assembly 62 and during axial movement of the depth cannula 134 during the surgical procedure. The bushing 132 also comprises a distal portion 366 between the proximal portion 358 and the distal end comprising a bore 368 in communication with the bore 360 of the proximal portion 358. The bore 368 of the distal portion 366 has a second inner diameter smaller than the first inner diameter. The bore 368 of the distal portion 366 is sized to approximate an outer diameter of the external surface of the depth cannula 134 to assist in keeping the depth cannula 114 concentric to the bushing 132 and the measurement axis MX.

Figure 60:
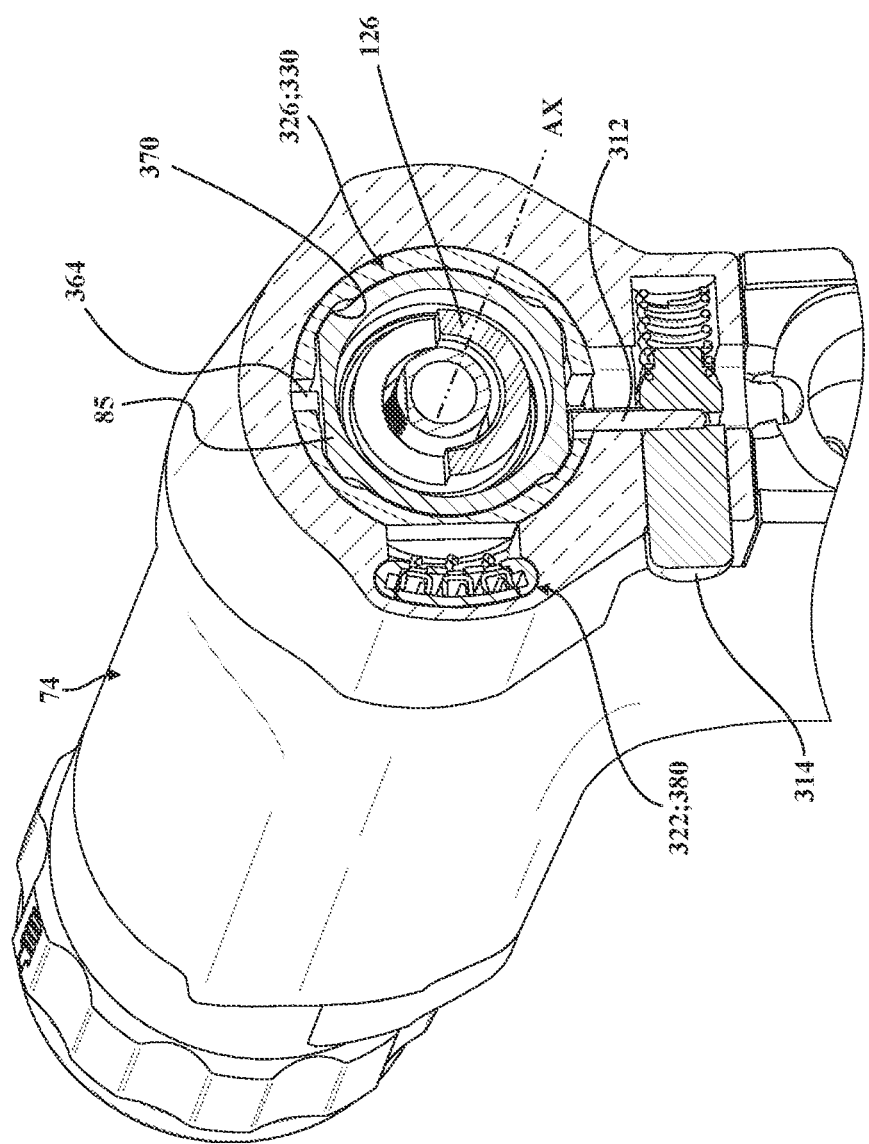
FIG. 60 is a partial isometric sectional view of the measurement module coupled to the surgical handpiece assembly of FIGS. 55-59 taken generally transverse to the longitudinal axis.
Figure 64:
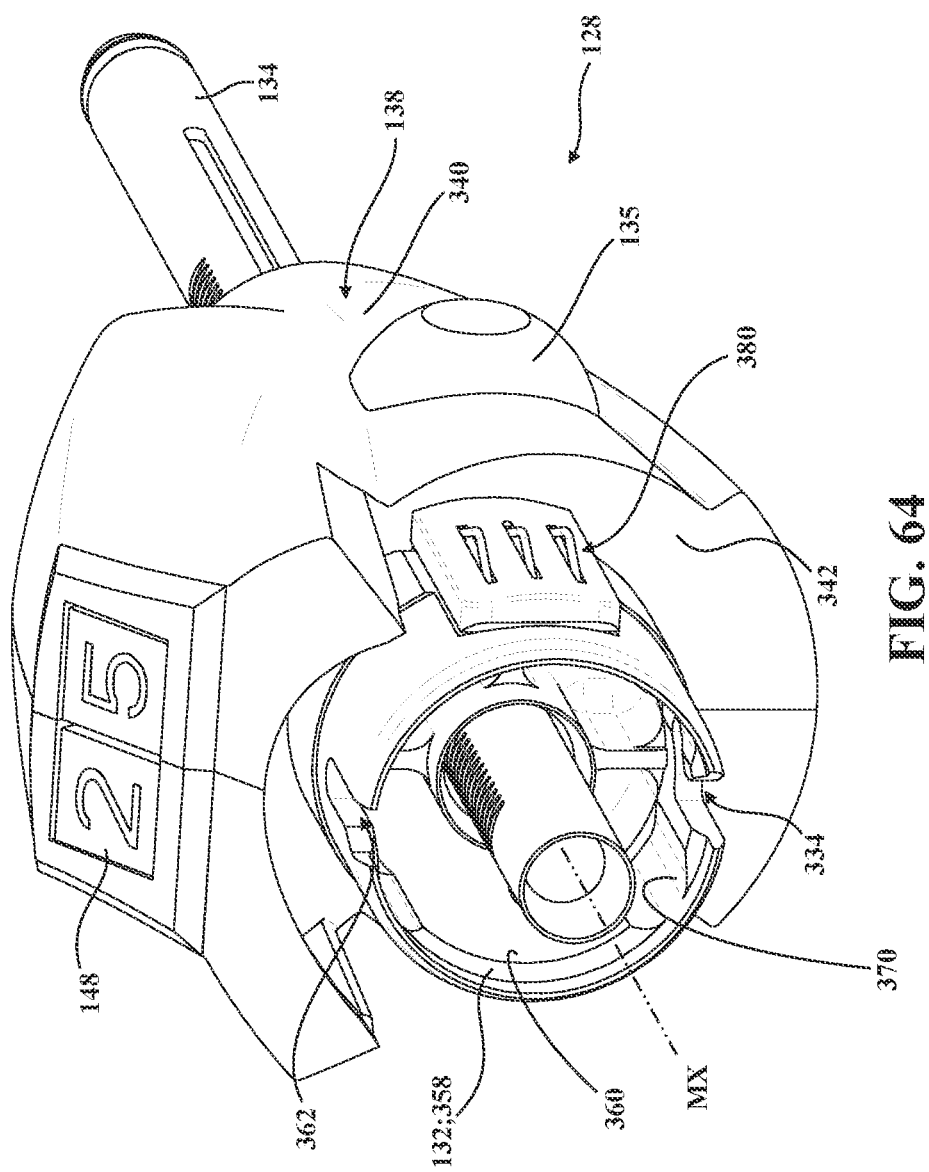
FIG. 64 is a perspective view of the measurement module of FIGS. 55-63.
Figure 65:
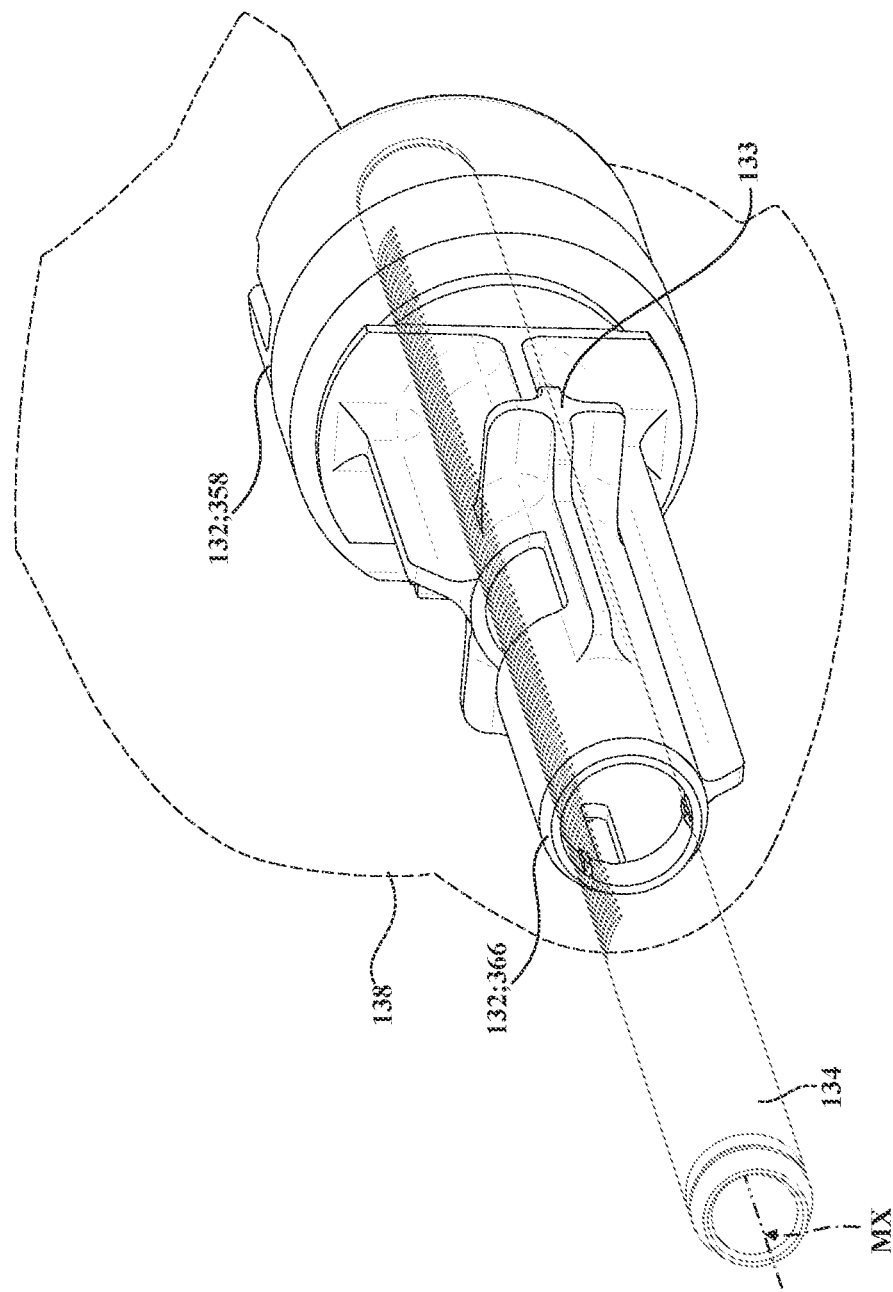
FIG. 65 is a perspective view of the measurement module of FIGS. 55-64 showing a bushing and showing the measurement housing and a depth cannula in phantom.

As best shown in FIGS. 60 and 64, the proximal portion 358 of the bushing 132 may define one or more recesses 370 in communication with the bore 360 of the proximal portion 358 of the bushing 132. The one or more recesses 370 are each configured to receive a portion of the motor housing 85 to assist in radially aligning the bushing 132 relative to the surgical handpiece assembly 62 and to ensure alignment of the measurement axis MX to the axis AX of the handpiece. In the illustrated configuration, the proximal portion 358 of the bushing 132 defines four recesses 370.

Figure 58:
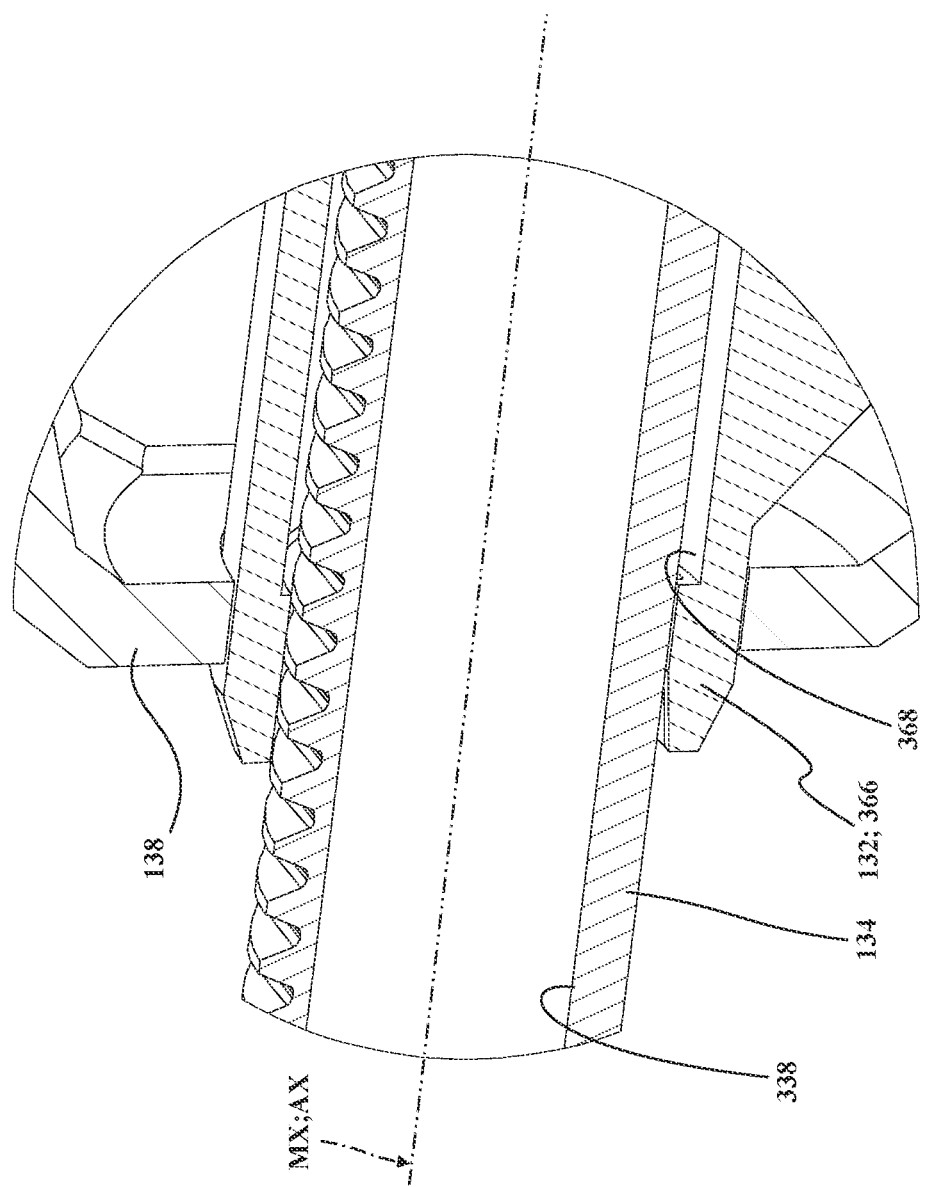
FIG. 58 is an enlarged detail view of the measurement module coupled to the surgical handpiece assembly of FIGS. 55-57, taken at indicia 58 in FIG. 57.
Figure 59:
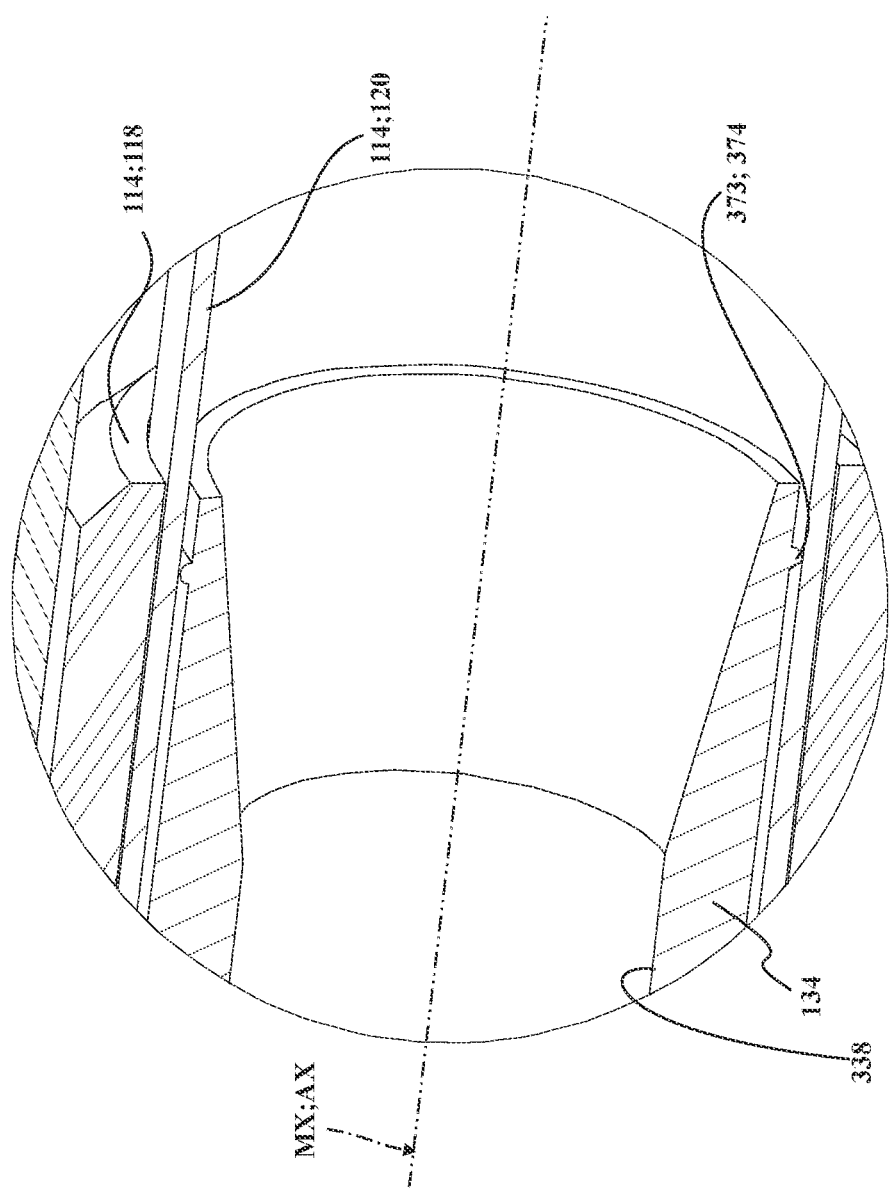
FIG. 59 is another enlarged detail view of the measurement module coupled to the surgical handpiece assembly of FIGS. 55-58, taken at indicia 59 in FIG. 57.

In one configuration shown in FIGS. 58, 59, and 66, at least one of the distal portion 366 of the bushing 132 and the depth cannula 134 comprises one or more protrusions extending toward the other of the distal portion 366 of the bushing 132 and the depth cannula 134. The one or more protrusions are configured to assist in centering the depth cannula 134 in the bore 368 of the distal portion 366 of the bushing 132 and within the bore 352 of the distal portion 118 of the drive cannula 114 of the surgical handpiece assembly 62. In some configurations, the one or more protrusions may each comprise an annular ring. In other configurations, the one or more protrusions 372 comprise individual protrusions 376 radially arranged about the bushing 132 (see FIG. 66). Although the one or more protrusions 372 are illustrated at the distal end portion of the bushing 132, it is contemplated that the one or more protrusions 372 may be arranged at another location along the bushing 132. For instance, the one or more protrusions 372 may be located directly beneath the gear 146 of the measurement module 128 to assist in retaining a consistent and tight meshing engagement of the gear 146 to the plurality of teeth of the depth cannula 134 when the depth cannula 134 moves along the measurement axis MX. The protrusions 372 may take the form of two, three or more axially extending ribs spaced apart in the bushing 132 to surround the depth cannula 134. In certain embodiments, the protrusions 372 on the bushing 132 are spaced such that they do not interact with the teeth of the depth cannula 134.

The depth cannula 134 may also comprise one or more protrusions 373 extending outwardly from the external surface of the depth cannula 134. The one or more protrusions 373 are configured to abut at least one of the bushing 132 and the drive cannula 114 to center the depth cannula 134 in the bores 360, 368 of the bushing 132, which results in the depth cannula 134 being centered in the bore 352 of the drive cannula 114. In one configuration shown in FIG. 59, the one or more protrusions 373 extending outwardly from the external surface of the depth cannula 134 comprises an annular ring 374. In the configuration illustrated in FIGS. 55-66, the one or more protrusions 373 extending outwardly from the external surface of the depth cannula 134 are configured to cooperate with the one or more protrusions 372 extending into the bore 368 of the bushing 132 to assist in centering the depth cannula 134 in the bore 368 of the bushing 132 and within the bore 352 of the drive cannula 114. Centering the depth cannula 134 in the bore 352 of the bushing 132 and the bore 352 of the drive cannula 114 assists in mitigating binding between the depth cannula 134, the drive cannula 114, and the drill bit 66 when the measurement coupler 326 is coupled to the handpiece housing assembly 74. It is particularly advantageous to use two sets of protrusions (a set of protrusions on the bushing 132 and a set of protrusions on the depth cannula 134) as described above to limit hinging that may occur with only one set of protrusions. The protrusions 372, 373 may have any suitable shape or size. The number of protrusions may vary, such as 1, 2, 3, 4 or more. The protrusions 372, 373 are sized and positioned such that the depth cannula 134 may move within the bore 368 of the bushing 132 without binding. In addition, it is contemplated that the depth cannula 134 may have two sets of protrusions, one set spaced apart axially from the other set. Similarly, it is contemplated that the bushing 132 may have two sets of protrusions, one set spaced apart axially from the other set.

Figure 62:
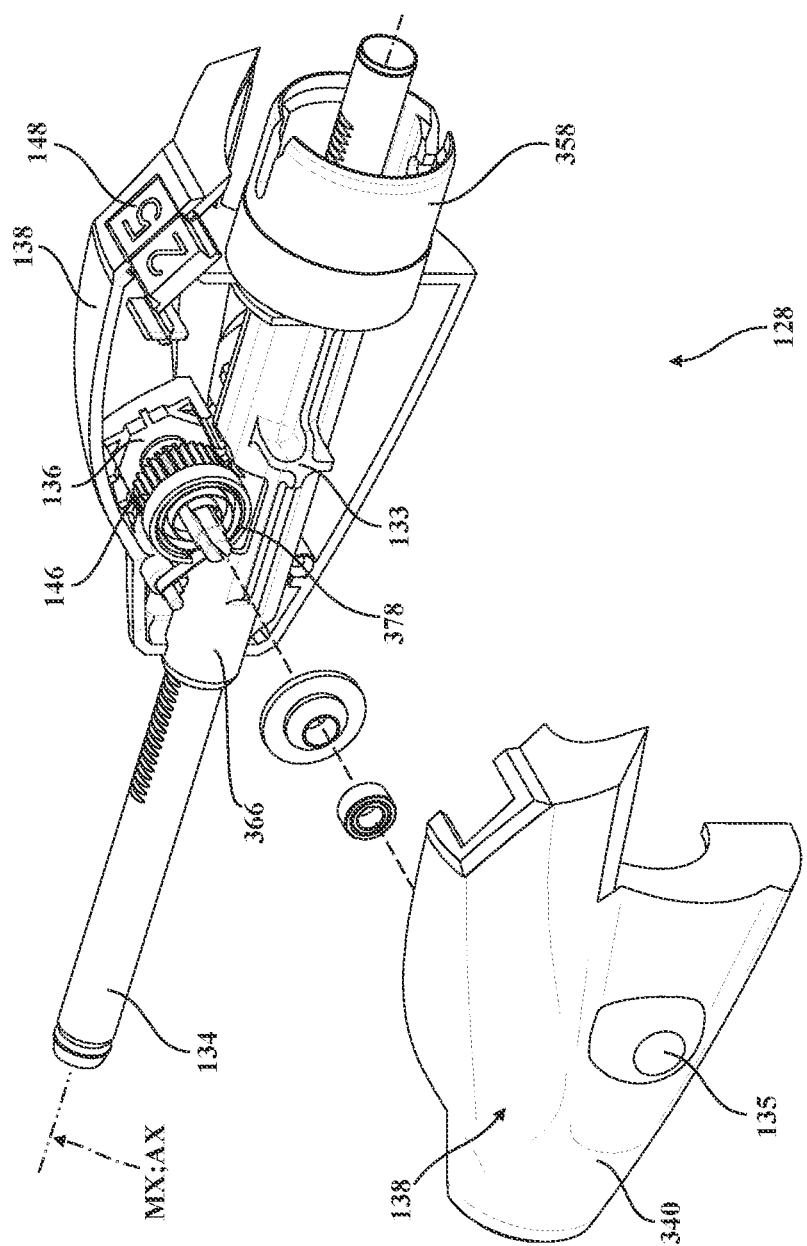
FIG. 62 is a partially-exploded view of the measurement module of FIGS. 55-61 showing a biasing mechanism disposed in an interior of a measurement housing.
Figure 63:
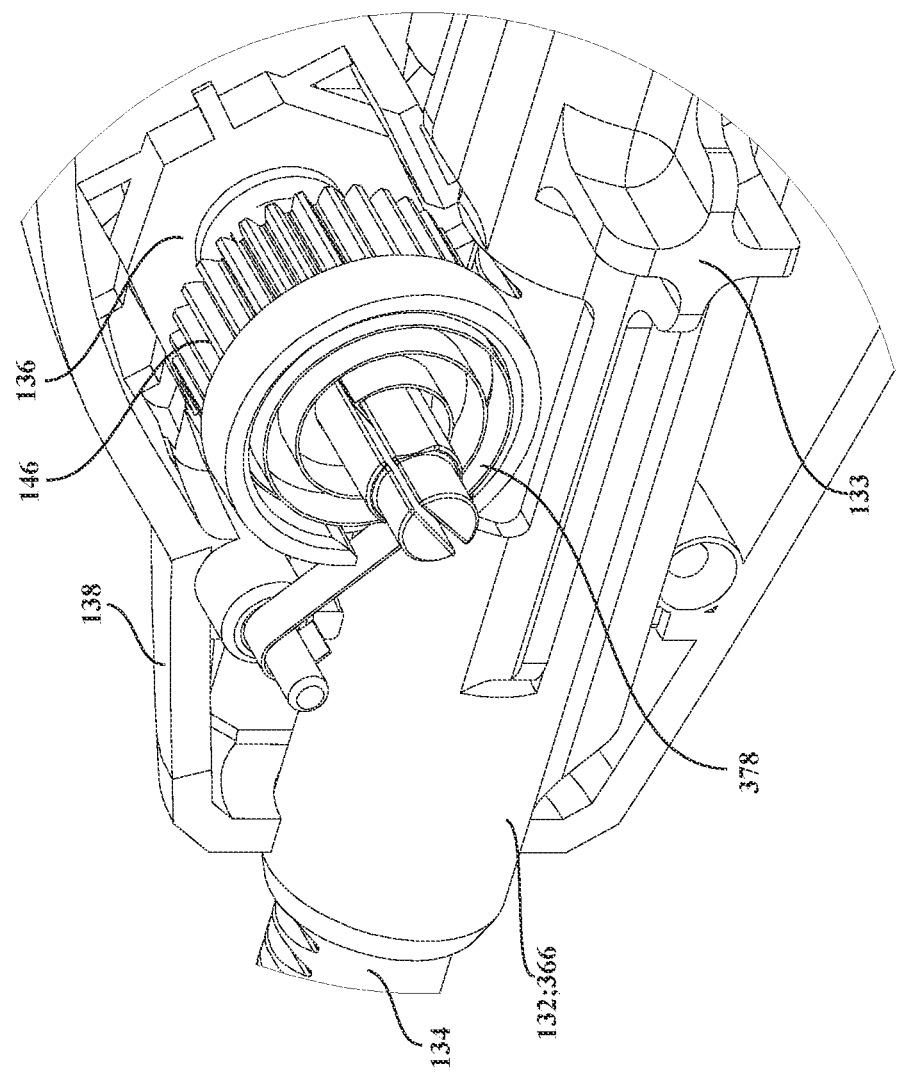
FIG. 63 is an enlarged view of the measurement module of FIGS. 55-62 showing the biasing mechanism disposed in the interior of the measurement housing.

As shown in FIGS. 62-63, the measurement module 128 comprises a biasing mechanism 378 coupled to the gear 146 and configured to bias the gear 146 to rotate in one direction such that the proximal end of the depth cannula 134 is biased to a biased position toward the distal end of the bushing 132. In the illustrated configuration, the biasing mechanism 378 comprises a torsion spring. The biasing mechanism 378 assists the displacement sensor assembly 136 to generate accurate signals for measurement functions associated with the depth cannula 134. Consistent and unrestricted (no binding) movement of the depth cannula 134 assists in proper operation of the biasing mechanism 378. More specifically, if the biasing mechanism 378 fails in properly returning the depth cannula 134 to the biased position of the depth cannula 134 during a surgical operation, the resulting signal may reflect an accurate position of the depth cannula 134, but the position of the depth cannula 134 may be in an incorrect position for the surgical operation as a result of binding.

It should be appreciated that the depth cannula 134, in certain embodiments, is freely movable relative to the measurement housing 138 and the surgical handpiece assembly 62 and does not act to limit the depth of drilling. In other words, the depth cannula 134 may not act as a drill stop and is not coupled to any actuator that positively controls how far the position of the depth cannula 134 is relative to the bone or plate. In other words, the depth cannula 134 may function solely to provide measurement functionality of the bore hole ultimately drilled, but not prevent the user from plunging too far.

Figure 61:
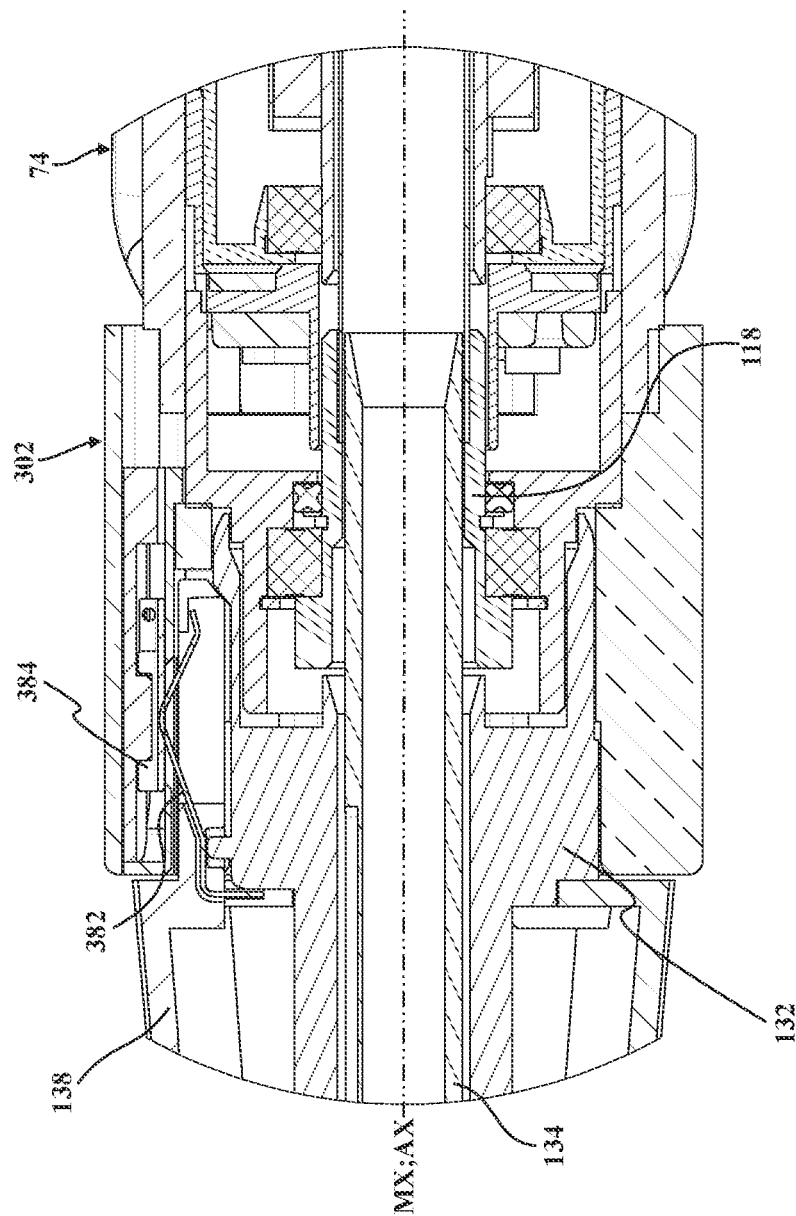
FIG. 61 is a sectional view of the measurement module coupled to the surgical handpiece assembly of FIGS. 55-60 taken generally along the longitudinal axis and transverse to the view of FIG. 57.

As shown in FIGS. 56, 61, and 64 the measurement housing 138 comprises an electrical connector 380 configured to engage the electrical connector 322 of the surgical handpiece assembly 62 (See FIGS. 55, 60, and 61) to transmit electrical power between the surgical handpiece assembly 62 and the measurement module 128 when the handpiece coupler 302 is coupled to the measurement coupler 326. In the configuration illustrated in FIGS. 56, 61, and 64, the electrical connector 380 of the measurement module 128 comprises three electrical terminals 382 and the electrical connector 322 of the surgical handpiece assembly 62 comprises three corresponding terminal contacts 384 configured to be in electrical contact when the measurement module 128 is coupled to the surgical handpiece assembly 62. In the illustrated configuration, the electrical terminals 382 are formed to be biased outwardly such that when the electrical terminals 382 engage (see FIG. 61) with the terminal contacts 384, the terminal contacts 384 apply force in opposition to the biased terminals 382 to assist in proper engagement of the terminals 382 to the terminal contacts 384. The three electrical terminals 382 extend from the proximal surface 342 of the body portion 340 of the measurement housing 138 and are spaced radially away from the bushing 132 relative to the measurement axis MX. More specifically, the group of three electrical terminals 382 is arranged to be spaced from the slots 334, 362 of the bayonet mount 330 at radially equal distances between the slots 334, 362. The three electrical terminals 382 comprise an electrical terminal for power, an electrical terminal for ground, and an electrical terminal for signal transfer. The electrical terminal for signal transfer may be used for communication and control between the measurement module 128 and the surgical handpiece assembly 62. In some configurations the measurement module 128 and the surgical handpiece assembly 62 comprise fewer than three terminals and terminal contacts, respectively. In other configurations, the measurement module 128 and surgical handpiece assembly 62 comprise more than three terminals and terminal contacts, respectively. The electrical connector 380 of the measurement housing 138 is configured to receive electrical power from the surgical handpiece assembly 62. The electrical connector of the measurement housing 138 is also coupled to the displacement sensor assembly 136 and the display 148 to supply electrical power to the displacement sensor assembly 136 and the display 148 when the measurement coupler 326 is coupled to the surgical handpiece assembly 62.

It should be appreciated that the protrusions, such as those described in FIGS. 58, 59, and 66, may be used with any of the other embodiments of the measurement module described. Additionally, it should be appreciated that any of the embodiments of the measurement module 128 may be used with any version of the surgical handpiece assembly 62 described throughout.

A method of reprocessing the depth measurement module for reuse is also contemplated. This method may include obtaining a measurement module that has previously been used. This use may include use during a surgical procedure such that the used measurement module previously contacted a patient. During use of the measurement module, one or more components of the measurement module may become soiled such that the used measurement module is no longer in a sterile condition. The term soiled relates to a component that has any residual biologic material disposed thereon. In certain embodiments, the gear and the plurality of teeth on the depth cannula may be soiled, i.e., have residual biologic material disposed thereon. The used measurement module may include any combination of components described above for the various embodiments of the measurement module described above. Any of the components of the measurement module may become soiled.

The method of reprocessing may further include dismantling at least two components of the measurement module from one another. The at least two components may be any component of the measurement module, such as the depth cannula, the gear, the measurement housing, the bushing, the display, etc. The step of dismantling may include separating the measurement housing from the depth cannula and the gear. The step of dismantling may include separating the depth cannula from the gear. The step of dismantling may include separating the bushing from the measurement housing. The step of dismantling may include breaking the measurement housing with a cutting step or breaking a joint step to separate the measurement housing into two components when the two components of the housing were secured to one another using welding or gluing. It should be appreciated that any of these dismantling steps may be performed alone or in combination, depending on the degree to which the measurement module is soiled.

Once the step of dismantling is complete, the method may include one or more cleaning steps. One potential cleaning step is to clean the soiled depth cannula. Another potential cleaning step is to clean the soiled gear. Another potential cleaning step is to clean the measurement housing. Yet another potential cleaning step is to clean the display. Additionally, the reprocessing method may include cleaning the bushing and/or the measurement coupler located on the measurement housing or the bushing. It should be appreciated one or more cleaning steps may also be performed before one or more steps of dismantling.

The type of cleaning for each component of the measurement module is not particularly limited, and may include mechanical cleaning steps and chemical cleaning steps. For example, the cleaning steps may include subjecting the component to be cleaned to an enzymatic cleaning process, an ultrasonic cleaning process, or a combination thereof. The depth cannula, bushing, and or the gear may be submerged during one or more cleaning steps. The step(s) of cleaning may comprise removing tissue from within the teeth of the depth cannula, from within teeth of the gear, or combinations thereof. Certain components may not be able to withstand aggressive cleaning steps, such as the display or the controller. For these components, the cleaning may include wiping the surface with a cleansing antibacterial wipe that may be alcohol-based. It should be appreciated that any of these steps may be performed alone or in combination, depending on the degree to which the measurement module is soiled.

The reprocessing method may further include a step of reassembling the measurement module. If one or more components of the used measurement module are not able to be effectively cleaned, are damaged during use, are damaged during one or more of the dismantling steps, or cannot be used for other reasons, the measurement module may be reassembled with one or more new components. The new components that can be used during the steps of reassembling are not particularly limited, exemplary new components may include a new depth cannula, a new gear, a new bushing, a new displacement sensor assembly, a new measurement housing, a new controller, a new display, or combinations thereof. In certain instances, one or more of the new components may be reassembled with one or more of the cleaned components.

For example, the step of reassembling may include reassembling the measurement module with one of the cleaned gear and the cleaned depth cannula. Alternatively, the step of reassembling the measurement module with both the cleaned depth measurement cannula and the cleaned gear. The step of reassembling may alternatively include reassembling the measurement module with a new measurement housing, such as with two or more components that cooperate to form the new measurement housing. The step of reassembling may further include reassembling the measurement module with the new display. The step of reassembling may alternatively include reassembling the measurement module with the cleaned bushing. The step of reassembling may alternatively include reassembling the measurement module with the new bushing. It is contemplated that during the step of reassembling that the new or cleaned depth cannula is placed into a meshing relationship with the new or used gear. It is also contemplated that the new or cleaned housing is reassembled such that the new or cleaned housing at least partially surrounds the new or cleaned gear and the new or cleaned depth cannula. The step of reassembling may include gluing or welding the components of the new or used measurement housing to one another. The step of reassembling may further include the step of securing the bushing to the measurement housing.

The method of reprocessing may further include the step of sterilizing the reassembled measurement module. The type of sterilization is not particularly limited, but in certain cases may include sterilizing the reassembled measurement module with the use of ethylene oxide gas. Other types of sterilizing may be used, such as autoclaving sterilization processes or gamma sterilization processes. While in certain embodiments, the measurement module is sterilized after it has been reassembled, it is contemplated that the components measurement module may be sterilized before reassembly as well.

It should be noted that in many of the figures described herein, certain components of the surgical handpiece system 60 have been removed for convenience of description and ease of illustration.

It should also be noted that while the surgical handpiece system is directed to surgical applications, the surgical handpiece system could be employed for non-surgical applications.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

I. A drill bit for releasably attaching to a drive assembly of a surgical instrument, the drill bit comprising:
 a shank extending along an axis between a proximal end and a distal end;
 a cutting tip portion adjacent to the distal end of the shank;
 an interface arranged between the proximal end and the distal end, the interface comprising an outermost drive portion spaced from the axis at a first interface distance, the outermost drive portion comprising an outer drive surface facing away from the axis;
 a resilient arm extending from the proximal end of the shank to an arm end, the resilient arm comprising an outer arm surface facing away from the axis, the resilient arm being movable relative to the axis between:
  a first position where the outer arm surface is spaced from the axis at a first arm distance greater than the first interface distance, and
  a second position where the outer arm surface is spaced from the axis at a second arm distance less than the first arm distance.

II. The drill bit as set forth in clause I, wherein the second arm distance is less than or equal to the first interface distance.

III. The drill bit as set forth in any one of clauses I-II, wherein the outer arm surface of the resilient arm and the outer drive surface of the outermost drive portion of the interface are each separately spaced from the axis at substantially the same distance when the resilient arm is in the second position.

IV. The drill bit as set forth in any one of clauses I-III, wherein the interface has a generally polygonal profile.

V. The drill bit as set forth in clause IV, wherein the interface has a rounded hexagonal profile.

VI. The drill bit as set forth in any one of clauses I-V, wherein the resilient arm further comprises an aligning element at the arm end configured to promote at least partial rotation of the drill bit about the axis as the resilient arm moves from the first position to the second position.

VII. The drill bit as set forth in clause VI, wherein the aligning element of the resilient arm at least partially comprises the outer arm surface.

VIII. The drill bit as set forth in any one of clauses VI-VII, wherein the aligning element of the resilient arm comprises a pair of planar arm surfaces adjacent to the outer arm surface;
 wherein the interface comprises a pair of planar surfaces; and
 wherein one of the planar arm surfaces is generally coplanar with one of the planar surfaces when the resilient arm is in the second position.

IX. An end effector assembly for releasably attaching to a drive assembly of a surgical instrument, the end effector assembly comprising:
 a drill bit extending along an axis between a cutting tip portion and an insertion portion; and
 a tip protector comprising a handle with a handle bore extending along a handle axis, and a receiver rotatably supported within the handle bore and constrained from translating along the handle axis relative to the handle, the receiver defining a receptacle capable of receiving the cutting tip portion of the drill bit;
 wherein the handle is adapted to be gripped by a user to facilitate attaching the drill bit to the surgical instrument such that the drill bit and the receiver rotate concurrently relative to the handle.

X. The end effector assembly as set forth in clause IX, wherein the insertion portion of the drill bit comprises:
 a shank extending along the axis between a proximal end and a distal end, with the cutting tip portion arranged adjacent to the distal end;
 an interface arranged between the proximal end and the distal end, the interface comprising an outermost drive portion spaced from the axis at a first interface distance; and
 a resilient arm extending from the proximal end of the shank to an arm end, the resilient arm comprising an outer arm surface facing away from the axis, the resilient arm being movable relative to the axis between:
  a first position where the outer arm surface is spaced from the axis at a first arm distance greater than the first interface distance, and
  a second position where the outer arm surface is spaced from the axis at a second arm distance less than the first arm distance; and
  wherein the resilient arm further comprises an aligning element at the arm end configured to promote at least partial rotation of the drill bit about the axis as the resilient arm moves from the first position to the second position in response to force applied to the handle as the drill bit end effector assembly is attached to the surgical instrument.

XI. The end effector assembly as set forth in any one of clauses IX-X, wherein at least a portion of the tip protector is resiliently deformable.

XII. The end effector assembly as set forth in any one of clauses IX-XI, wherein the receiver is configured to receive drill bit cutting tip portions of different sizes.

XIII The end effector assembly as set forth in any one of clauses IX-XII, wherein the drill bit is formed from a ferromagnetic material; and wherein the tip protector further comprises a magnet capable of holding the cutting tip portion of the drill bit within the receiver.

XIV. An end effector assembly for releasably attaching to a drive assembly of a surgical instrument, the end effector assembly comprising:
 a drill bit extending along an axis between a cutting tip portion and an insertion portion; and
 a tip protector removably coupled to the cutting tip portion of the drill bit for allowing a user to handle the drill bit without contacting the cutting tip portion.

XV. A method for mounting a drill bit on a surgical instrument having a drive assembly, the drill bit having an insertion portion and a cutting tip portion removably coupled to a tip protector, the method comprising:
 grasping the tip protector; and
 inserting the insertion portion of the drill bit into the surgical instrument such that the drill bit rotates relative to at least a portion of the tip protector when the drill bit is coupled to the drive assembly.

XVI. The method as set forth in clause XV, wherein the step of inserting the insertion portion of the drill bit into the surgical instrument comprises rotating a receiver of the tip protector holding the cutting tip portion of the drill bit relative to a handle of the tip protector.

XVII. The method as set forth in any one of clauses XV-XVI, further comprising axially constraining movement of the drill bit relative to the tip protector.

XVIII. A surgical instrument for use with a drill bit extending along an axis and having a retention surface movable from a first position toward the axis to a second position to facilitate releasably attaching the drill bit to the surgical instrument, the surgical instrument comprising:
   a handpiece body;
   a drive assembly supported within the handpiece body and comprising a driving cannula configured to axially and rotatably secure the drill bit to the surgical instrument; and
   a release mechanism configured to facilitate removal of the drill bit from the drive assembly.

XIX. The surgical instrument as set forth in clause XVIII, wherein the release mechanism comprises a slide element arranged for axial translation to facilitate removal of the drill bit from the drive assembly.

XX. The surgical instrument as set forth in clause XIX, wherein the slide element of the release mechanism further comprises an actuating element shaped to engage a resilient arm of the drill bit to urge the resilient arm at least partially toward the axis.

XXI. The surgical instrument as set forth in clause XX, wherein the slide element of the release mechanism further comprises a pocket; and
   wherein the release mechanism further comprises:
      a spherical guide supported within the pocket of the slide element;
      a release body comprising a helical slot extending helically about and along the axis; and
      a collar comprising a collar channel facing toward the axis; and
      wherein the spherical guide rides along the helical slot formed in the release body and translates along the collar channel formed in the collar to facilitate translation of the slide element along the axis in response to rotation of the collar about the axis to facilitate bringing the actuating element into engagement with the resilient arm of the drill bit such that the drill bit can be removed from the surgical instrument.

XXII. A drill bit comprising:
   a shank extending along an axis between a proximal end and a distal end;
      a cutting tip portion adjacent to the distal end of the shank;
      an interface arranged between the proximal end and the distal end, the interface comprising a first outermost drive portion and a second outermost drive portion spaced from one another to define a maximum drive dimension of the interface, with the first outermost drive portion spaced from the axis at a first interface distance and the second outermost drive portion spaced from the axis at a second interface distance; and
   a resilient arm extending from the proximal end of the shank to an arm end, the resilient arm comprising an outer arm surface facing away from the axis, and a retention surface facing toward the distal end of the shank and radially aligned about the axis with one of the first and second outermost drive portions, the resilient arm being movable relative to the axis between:
      a first position where the outer arm surface is spaced from the axis at a first arm distance, with the first arm distance greater than the first interface distance when the retention surface is radially aligned with the first outermost drive portion, and the first arm distance greater than the second interface distance when the retention surface is radially aligned with the second outermost drive portion, and
      a second position where the outer arm surface is spaced from the axis at a second arm distance less than the first arm distance, with the second arm distance less than or equal to the first interface distance when the retention surface is radially aligned with the first outermost drive portion, and the second arm distance less than or equal to the second interface distance when the retention surface is radially aligned with the second outermost drive portion.

XXIII The drill bit as set forth in clause XXII, wherein the first interface distance and the second interface distance comprise a common distance at which each of the first outermost drive portion and the second outermost drive portion is spaced from the axis.

XXIV. A drill bit comprising:
   a shank extending along an axis between a proximal end and a distal end;
      a cutting tip portion adjacent to the distal end of the shank;
      an interface arranged between the proximal end and the distal end, the interface comprising at least two outermost drive portions spaced from one another to define a maximum drive dimension of the interface with the two outermost drive portions each separately spaced at a first interface distance from the axis; and
   a resilient arm extending from the proximal end of the shank to an arm end, the resilient arm comprising an outer arm surface facing away from the axis, and a retention surface facing toward the distal end of the shank and radially aligned about the axis with one of the outermost drive portions, the resilient arm being movable relative to the axis between:
      a first position where the outer arm surface is spaced from the axis at a first arm distance greater than the first interface distance, and
      a second position where the outer arm surface is spaced from the axis at a second arm distance less than the first arm distance and less than or equal to the first interface distance.

XXV. The drill bit as set forth in clause XXIV, wherein the interface comprises at least four planar surfaces.

XXVI. The drill bit as set forth in clause XXV, wherein the interface comprises six planar surfaces.

XXVII. The drill bit as set forth in any one of clauses XXIV-XXVI, wherein the interface comprises at least four corners with two of the corners defining the outermost drive portions.

XXVIII. The drill bit as set forth in clause XXVII, wherein the interface comprises at least six corners.

XXIX. The drill bit as set forth in in any one of clauses XXIV-XXVIII, wherein the interface comprises a plurality of drive lobes with two of the drive lobes defining the outermost drive portions.

XXX. The drill bit as set forth in clause XXIX, wherein the plurality of drive lobes comprises four or more drive lobes.

XXXI. The drill bit as set forth in clause XXIX, wherein the resilient arm and one of the drive lobes comprise a common bisecting plane intersecting the axis to define two equal portions of the resilient arm and two equal portions of the outermost drive portion.

XXXII. The drill bit as set forth in any one of clauses XXIV-XXXI, wherein the resilient arm is further defined as a first resilient arm; and
   further comprising a second resilient arm extending from the proximal end of the shank to a second arm end, the second resilient arm comprising a second outer arm surface facing away from the axis, and a second retention surface facing toward the distal end of the shank and radially aligned about the axis with one of the outermost drive portions; and
      wherein the first and second resilient arms are each respectively movable relative to the axis between:

respective first positions where the respective outer arm surfaces are spaced from the axis at respective first arm distances greater than the first interface distance, and respective second positions where the respective outer arm surfaces are spaced from the axis at respective second arm distances less than the respective first arm distances and less than or equal to the first interface distance.

XXXIII The drill bit as set forth in any one of clauses XXIV-XXXII, wherein the resilient arm extends at least partially away from the axis from the proximal end of the shank to the arm end.

XXXIV. The drill bit as set forth in any one of clauses XXIV-XXXIII, wherein the resilient arm comprises a finger portion at the arm end, the finger portion providing the retention surface.

XXXV. The drill bit as set forth in clause XXXIV, wherein the finger portion forms a ramp surface configured to deflect the resilient arm toward the axis.

XXXVI. The drill bit as set forth in any one of clauses XXIV-XXXV, wherein the interface extends along the axis between a distal interface end and a proximal interface end, with an interface length defined between the distal interface end and the proximal interface end; and wherein the retention surface is spaced from the proximal interface end at a retention distance greater than or equal to the interface length.

XXXVII. The drill bit as set forth in any one of clauses XXIV-XXXVI, wherein the interface extends along the axis between a distal interface end and a proximal interface end, with an interface length defined between the distal interface end and the proximal interface end; and wherein the shank has a shank length defined between the distal end and the proximal end, with the shank length being greater than or equal to three times the interface length.

XXXVIII. The drill bit as set forth in any one of clauses XXIV-XXXII, wherein the drill bit is cannulated.

XXXIX. The drill bit as set forth in any one of clauses XXIV-XXXVIII, wherein the drill bit is a twist drill bit.

XXXX. The drill bit as set forth in any one of clauses XXIV-XXXIX, wherein the resilient arm and one of the outermost drive portions are radially positioned within fifteen degrees of one another relative to the axis.

XXXXI. The drill bit as set forth in any one of clauses XXIV-XXXXI, wherein the retention surface and one of the outermost drive portions comprise a common bisecting plane intersecting the axis to define two equal portions of the resilient arm and two equal portions of the outermost drive portion.

XXXXII. A drill bit comprising:

a shank extending along an axis between a proximal end and a distal end;

a cutting tip portion adjacent to the distal end of the shank;

an interface arranged between the proximal end and the distal end, the interface comprising at least two outermost drive portions spaced from one another to define a maximum drive dimension of the interface with the two outermost drive portions each separately spaced at a first interface distance from the axis; and a resilient arm extending from the proximal end of the shank to an arm end, the resilient arm comprising an outer arm surface facing away from the axis, and a retention surface facing toward the distal end of the shank, the resilient arm being movable relative to the axis between:

a first position where the outer arm surface is spaced from the axis at a first arm distance greater than the first interface distance, and a second position where the outer arm surface is spaced from the axis at a second arm distance less than the first arm distance and less than or equal to the first interface distance;

wherein the retention surface comprises a first bisecting plane that intersects the axis to define two equal portions of the retention surface;

wherein one of the outermost drive portions comprises a second bisecting plane that intersects the axis to define two equal portions of the outermost drive portion; and wherein the second bisecting plane is radially spaced approximately 60 degrees from the first bisecting plane about the axis.

XXXXIII A drill bit comprising:

a shank extending along an axis between a proximal end and a distal end;

a cutting tip portion adjacent to the distal end of the shank;

an interface arranged between the proximal end and the distal end, the interface comprising at least two outermost drive portions spaced from one another to define a maximum drive dimension of the interface with the two outermost drive portions each separately spaced at a first interface distance from the axis, and the interface further comprising at least two outer non-drive portions spaced diametrically from one another relative to the axis to define a minimum interface dimension, the two outer non-drive portions being radially spaced from the two outermost drive portions about the axis;

a resilient arm extending from the proximal end of the shank to an arm end, the resilient arm comprising an outer arm surface facing away from the axis, and a retention surface facing toward the distal end of the shank and radially aligned about the axis with one of the outermost drive portions, the resilient arm being movable relative to the axis between:

a first position where the outer arm surface is spaced from the axis at a first arm distance greater than the first interface distance, and a second position where the outer arm surface is spaced from the axis at a second arm distance less than the first arm distance and less than or equal to the first interface distance.

XXXXIV. The drill bit as set forth in clause XXXXIII, wherein the interface comprises at least four planar surfaces.

XXXXV. The drill bit as set forth in any one of clauses XXXXIII-XXXXIV, wherein the interface comprises at least four corners with two of the corners defining the outermost drive portions.

XXXXVI. The drill bit as set forth in any one of clauses XXXXIII-XXXXV, wherein the interface comprises a plurality of drive lobes with two of the drive lobes defining the outermost drive portions.

XXXXVII. The drill bit as set forth in clause XXXXVI, wherein the plurality of drive lobes comprises four or more drive lobes.

XXXXVIII. The drill bit as set forth in any one of clauses XXXXIII-XXXXVII, wherein the resilient arm is further defined as a first resilient arm; and further comprising a second resilient arm extending from the proximal end of the shank to a second arm end, the second resilient arm comprising a second outer arm surface facing away from the axis, and a second retention surface facing toward the distal end of the shank and radially aligned about the axis with one of the outermost drive portions; and wherein the first and second resilient arms are each respectively movable relative to the axis between:

respective first positions where the respective outer arm surfaces are spaced from the axis at respective first arm distances greater than the first interface distance, and respective second positions where the respective outer arm surfaces are spaced from the axis at respective second arm distances less than the respective first arm distances and less than or equal to the first interface distance.

XXXXIX. The drill bit as set forth in any one of clauses XXXXIII-XXXXVIII, wherein the resilient arm extends at least partially away from the axis from the proximal end of the shank to the arm end.

L. The drill bit as set forth in clause XXXXIX, wherein the resilient arm comprises a finger portion at the arm end, the finger portion providing the retention surface.

LI. The drill bit as set forth in clause L, wherein the finger portion forms a ramp surface configured to deflect the resilient arm toward the axis.

LII. A drill bit comprising:
a shank extending along an axis between a proximal end and a distal end;
a cutting tip portion adjacent to the distal end of the shank;
an interface arranged between the proximal end and the distal end, the interface comprising at least one outermost drive portion spaced at a first interface distance from the axis; and
a resilient arm extending from the proximal end of the shank to an arm end, the resilient arm comprising an outer arm surface facing away from the axis, and a retention surface facing toward the distal end of the shank and radially aligned about the axis with respect to the outermost drive portion at an angle of approximately 0-degrees, 60-degrees, 120-degrees, or 180-degrees, the resilient arm being movable relative to the axis between:
a first position where the outer arm surface is spaced from the axis at a first arm distance greater than the first interface distance, and
a second position where the outer arm surface is spaced from the axis at a second arm distance less than the first arm distance and less than or equal to the first interface distance.

LIII. A method of preparing a depth sensing measurement module for reuse, said method comprising:
obtaining a measurement module that has been previously been used, the measurement module including:
a measurement housing;
a depth cannula movably coupled to said measurement housing, the depth cannula comprising a plurality of teeth disposed linearly along at least a partial length of the depth cannula;
a gear rotatably coupled to the measurement housing, the gear is disposed in a meshing relationship with the plurality of teeth such that rotation of the gear and movement of the depth cannula are directly proportional;
a displacement sensor assembly configured to generate a signal responsive to movement of the gear; and
a display coupled to the measurement housing;
wherein a residual biologic material is disposed on one or more of the plurality of teeth and the gear which results in the depth cannula and the gear being soiled;
dismantling at least two components of the measurement module from one another;
cleaning at least one of the soiled depth cannula and the soiled gear;
reassembling the measurement module with one of the cleaned gear and the cleaned depth cannula; and
sterilizing the reassembled measurement module.

LIV. The method of clause LIII, further comprising cleaning both the soiled depth cannula and the soiled gear;
reassembling the measurement module with both the cleaned depth measurement cannula and the cleaned gear; and
sterilizing the reassembled measurement module.

LV. The method of any one of clauses LIII-LIV, wherein the step of dismantling the measurement module comprises separating the measurement housing from the soiled depth cannula and the soiled gear.

LVI. The method of any one of clauses LIII-LV, further comprising providing a new depth measurement cannula, and wherein the step of reassembling the measurement module comprises reassembling the measurement module with the cleaned gear and the new depth measurement cannula.

LVII. The method in any one of clauses LIII-LVI, further comprising providing a new measurement housing, and wherein the step of reassembling the measurement module comprises reassembling the measurement module with the new measurement housing.

LVIII. The method in any one of clauses LIII-LVII, further comprising providing a new display, and wherein the step of reassembling the measurement module comprises reassembling the measurement module with the new display.

LIX. The method in any one of clauses LIII-LVIII, wherein the step of cleaning comprises removing tissue from within the teeth of the depth cannula, from within teeth of the gear, or combinations thereof.

LX. The method in any one of clauses LIII-LIX, wherein the measurement module that has been previously been used comprises a bushing that at least partially surrounds the used depth cannula, said method further comprising cleaning the bushing; and wherein the step of reassembling further comprises reassembling the measurement module with the cleaned bushing.

LXI. The method in any one of clauses LIII-LX, wherein the measurement module that has been previously been used comprises a bushing that at least partially surrounds the used depth cannula, said method further comprising providing a new bushing; and wherein the step of reassembling further comprises reassembling the measurement module with the new bushing.

LXII. The method in any one of clauses LIII-LXI, wherein the step of sterilizing includes subjecting the reassembled measurement module to ethylene oxide gas.

LXIII. The method in any one of clauses LIII-LXII, wherein the step of cleaning includes subjecting one of the soiled depth cannula and the soiled gear to an enzymatic cleaning process, an ultrasonic cleaning process, or a combination thereof.

LXIV. The method in any one of clauses LIII-LXIII, wherein the measurement module that has been previously used comprises a measurement coupler, said method further comprises cleaning the measurement coupler.

LXV. A method of preparing a depth sensing measurement module for reuse, said method comprising:
obtaining a measurement module that has been previously been used, the measurement module including:
a measurement housing;
a depth cannula movably coupled to said measurement housing, the depth cannula comprising a plurality of teeth disposed linearly along at least a partial length of the depth cannula;

a gear rotatably coupled to the measurement housing, the gear is disposed in a meshing relationship with the plurality of teeth such that rotation of the gear and movement of the depth cannula are directly proportional;

a displacement sensor assembly configured to generate a signal responsive to movement of the gear;

a display coupled to the measurement housing;

wherein a residual biologic material is disposed on one or more of the plurality of teeth and the gear which results in the depth cannula and the gear being soiled;

dismantling at least two components of the measurement module from one another;

disengaging the teeth of the soiled depth cannula from the soiled gear;

reassembling the measurement module with a new depth cannula; and sterilizing the reassembled measurement module.

LXVI. A measurement module for facilitating alignment to a surgical handpiece assembly having a handpiece housing assembly supporting a drive cannula and a drill bit, each rotatable about a handpiece axis, with the drill bit extending along the handpiece axis disposed within a bore of the drive cannula, the measurement module comprising:

a measurement housing comprising a proximal region and a distal region, with the proximal region comprising a proximal surface;

a depth cannula movably coupled to the measurement housing, the depth cannula comprising a proximal end, a distal end, and a length therebetween disposed along a measurement axis, the depth cannula configured to move along the measurement axis relative to the measurement housing through the proximal and distal regions, and the depth cannula comprising, a bore extending through the proximal and distal ends configured to receive the drill bit, a bushing partially received in the measurement housing and extending along the measurement axis between a proximal end protruding through the proximal surface of the measurement housing and a distal end adjacent the distal region of the measurement housing, and the bushing comprising, a bore configured to receive the depth cannula, and one or more protrusions extending into the bore of the bushing;

a bayonet coupler configured to be removably coupleable to the handpiece housing assembly;

one or more electrical terminals extending from the proximal surface of the measurement housing and spaced from the bushing.

a displacement sensor assembly configured to generate a signal responsive to movement of the depth cannula; and a display coupled to the measurement housing;

LXVII. A measurement module for attachment to a handheld surgical instrument to provide measurement functionality to the handheld surgical instrument, the measurement module comprising:

a mechanical assembly comprising a detection element configured to move a distance during use of the surgical instrument, the distance being indicative of a procedural parameter; and a sensor assembly removably coupleable to the mechanical assembly and operatively engageable with the detection element of the mechanical assembly such that the sensor assembly is configured to sense the distance moved by the detection element of the mechanical assembly when the sensor assembly is coupled to the mechanical assembly, wherein the mechanical assembly is capable of withstanding autoclave exposure, and the sensor assembly is incapable of withstanding autoclave exposure.

LXVIII. The measurement module of clause LXXVIII, wherein the sensor assembly comprises an unsealed electrical component.

LXIX. The measurement module of clause LXXVIII, wherein the mechanical assembly is free of electrical components.

LXX. The measurement module of clause LXXVIII, wherein the mechanical assembly comprises a first casing, and the detection element is a probe movably disposed at least partially within the first casing, and the probe is configured to be linearly displaced relative to the first casing.

LXXI. The measurement module of clause LXX, wherein the sensor assembly comprises a second casing, the second casing being removably coupleable to the first casing of the mechanical assembly.

LXXII. The measurement module of clause LXXI, wherein the detection element comprises:

a cannula movably coupled to the first casing; and a gear movably coupled to the cannula and configured to rotate in response to the cannula being linearly displaced, wherein the sensor assembly is engaged with the gear to detect a characteristic of rotation of the gear when the first casing is coupled to the second casing.

LXXIII. The measurement module in any one of clauses LXXI-LXXII, wherein the sensor assembly comprises a sensor, wherein the sensor is secured to the second casing such that the sensor is positioned to operatively engage the detection element when the second casing is coupled to the first casing.

LXXIV. The measurement module of clause LXXIII, wherein the sensor assembly comprises a circuit and a sensor coupled to the circuit, the sensor is configured to provide an input signal based on the distance moved by the detection element, and the circuit is configured to determine the distance moved by the detection element based on the input signal and generate a notification signal to notify a user based on the distance moved by the detection element.

LXXV. The measurement module of clause LXXIV, wherein the sensor assembly further comprises a visual indicator electrically coupled to the circuit and configured to receive the notification signal from the circuit to display an indicator of the distance moved by the detection element based on the notification signal.

LXXVI. The measurement module of clause LXXIV, wherein the sensor comprises an electrical sensor.

LXXVII. The measurement module in any one of clauses LXXIII-LXXVI, wherein the sensor assembly further comprises a power receiver, the power receiver is configured to receive power from the handheld surgical instrument when the measurement module is coupled to the handheld surgical instrument.

LXXVIII. A handheld surgical instrument comprising:

a housing comprising a distal region, a proximal region, and a barrel extending from the distal region towards the proximal region; and a drive system comprising a rear drive point positioned within the proximal region of the housing and a forward drive point positioned within the distal region of the housing, the forward drive point and the rear drive point each capable of driving a respective one of an attachment or a surgical end effector coupled thereto.

LXXIX. The handheld surgical instrument of clause LXXVIII, further comprising a measurement module configured to be removably coupled to the distal region of the housing of the surgical instrument when the surgical end effector is removably coupled to the rear drive point.

LXXX. The handheld surgical system of clause LXXIX, further comprising an attachment removably coupleable to the forward drive point of the drive system when the distal region of the housing of the surgical instrument is free of the measurement module.

LXXXI. The handheld surgical instrument of clause LXXX, wherein the drive system comprises:
 a driving cannula comprising a length terminating at one end portion with the rear drive point integrated therein and an opposing end portion with the forward drive point integrated therein, and the driving cannula is rotatably disposed within the housing;
 a motor providing a torque; and
 a gear train configured to increase the torque provided by the motor and transmit the torque to the driving cannula.

LXXXII. The handheld surgical instrument in any one of clauses LXXIX-LXXXI, wherein the measurement module comprises a casing, a circuit disposed within the casing, and a power receiver coupled to the circuit,
 wherein the housing comprises a power supply configured to supply power to the power receiver for the measurement module when the measurement module is coupled to the housing.

LXXXIII. A method for using a measurement module with a handheld surgical instrument having a proximal region and a distal region to provide measurement functionality to the handheld surgical instrument, the measurement module comprising a mechanical assembly that comprises a detection element and a sensor assembly removably coupleable to the mechanical assembly and operatively engageable with the detection element of the mechanical assembly, the method comprising:
 coupling the measurement module to a first handheld surgical instrument;
 using the first handheld surgical instrument during a first surgical session in a manner that causes the detection element to move a distance indicative of a procedural parameter;
 sensing the distance moved by the detection element with the sensor assembly;
 decoupling the sensor assembly from the mechanical assembly of the measurement module;
 discarding the sensor assembly of the measurement module after the first surgical session; and
 reusing the mechanical assembly of the measurement module during a second surgical session with the first handheld surgical instrument or a second handheld surgical instrument different from the first handheld surgical instrument.

LXXXIV. The method of clause LXXXIII, further comprising sterilizing the mechanical assembly after the first surgical session.

LXXXV. The method in any one of clauses clause LXXXIII-LXXXIV, further comprising coupling the mechanical assembly of the measurement module with a second sensor assembly to provide measurement functionality during the second surgical session.

LXXXVI. The method of any one of clauses LXXXIII-LXXXV, further comprising coupling a surgical end effector to the proximal region of the handheld surgical instrument when the measurement module is coupled to the first handheld surgical instrument.

LXXXVII. The method of clause LXXXVI, further comprising coupling an attachment to the distal region of the handheld surgical instrument when the first handheld surgical instrument is free of the measurement module.

LXXXVIII. A modular surgical system comprising:
 a handheld surgical instrument comprising a housing and a drive system;
 an attachment removably coupleable to the handheld surgical instrument, the attachment capable of performing an operational function; and
 a measurement module removably coupleable to the handheld surgical instrument, the measurement module capable of performing a measurement function associated with the operational function.

LXXXIX. The modular surgical system of clause LXXXVIII wherein the housing of the handheld surgical instrument comprises a first coupler, and the measurement module comprises a second coupler removably coupleable to the first coupler of the handheld surgical instrument, and the attachment comprises a third coupler removably coupleable to the first coupler of the handheld surgical instrument.

XC. The modular surgical system any one of clauses LXXXVIII-LXXXIX wherein the measurement module is configured to receive only electrical energy from the handheld surgical instrument in order to perform the measurement function.

XCI. The modular surgical system of clause LXXXVIII wherein the attachment is configured to receive only mechanical energy from the drive system in order to perform the operational function.

XCII. A surgical handpiece assembly for operating a drill bit having one or more resilient arms to engage the surgical handpiece, the surgical handpiece assembly comprising:
 a housing assembly comprising a proximal region and a distal region;
 a drive element rotatably coupled to the housing assembly and configured to receive torque from and rotate in response to a motor, the drive element comprising a driving portion configured to transmit torque to the drill bit;
 a retention surface adjacent the proximal end of the drive element configured to assist the one or more resilient arms of the drill bit to retain an axial position of the drill bit relative to the drive cannula; and
 a release assembly proximal the proximal end of the drive element, the release assembly comprising a release member moveable relative to the retention surface to a first position and a second position, the release member configured to operatively disengage the one or more resilient arms of the drill bit from engagement with the retention surface to permit the drill bit to move axially relative to the drive element in response to the release member moving from the first position to the second position.

XCIII. A surgical handpiece system for performing measurement functions and surgical operations, the surgical handpiece system comprising:
 a handpiece assembly comprising,
  a handpiece housing assembly comprising a proximal region and a distal region, and the handpiece housing assembly comprising a handpiece coupler adjacent the distal region, and a drive element rotatably coupled to the handpiece housing assembly, the drive cannula extending along a longitudinal axis and being configured to receive torque from a motor;

a surgical attachment module removably coupleable to the handpiece housing assembly adjacent the distal region, the surgical attachment module comprising, a surgical attachment housing comprising a surgical attachment coupler adapted to cooperate with the handpiece coupler to removably couple the surgical attachment housing to the handpiece housing assembly adjacent the distal region, and a drive shaft rotatably coupled to the surgical attachment housing and configured to receive torque from the drive element to operate an end effector; and a measurement module removably coupleable to the handpiece housing assembly adjacent the distal region, the measurement module being configured to perform measurement functions associated with operation of the handpiece assembly, and the measurement module comprising a measurement housing and a measurement coupler, wherein the measurement coupler is configured to cooperate with the handpiece coupler to removably couple the measurement housing to the handpiece housing assembly adjacent the distal region.

What is claimed is:

1. A surgical handpiece system for performing measurement functions and surgical operations, the surgical handpiece system comprising:

a surgical handpiece assembly comprising, a handpiece housing assembly comprising a proximal region and a distal region, and the handpiece housing assembly comprising a handpiece coupler adjacent the distal region, and a drive cannula rotatably coupled to the handpiece housing assembly, the drive cannula extending along a longitudinal axis and being configured to receive torque from a motor;

a surgical attachment module removably coupleable to the handpiece housing assembly adjacent the distal region, the surgical attachment module comprising, a surgical attachment housing comprising a surgical attachment coupler adapted to cooperate with the handpiece coupler to removably couple the surgical attachment housing to the handpiece housing assembly adjacent the distal region, and a drive shaft rotatably coupled to the surgical attachment housing and configured to receive torque from the drive cannula to operate an attachment module end effector; and a measurement module removably coupleable to the handpiece housing assembly adjacent the distal region, the measurement module being configured to perform measurement functions associated with operation of the surgical handpiece assembly, and the measurement module comprising a measurement housing and a measurement coupler, wherein the measurement coupler is configured to cooperate with the handpiece coupler to removably couple the measurement housing to the handpiece housing assembly adjacent the distal region.

2. The surgical handpiece system of claim 1, wherein the handpiece housing assembly comprises a first electrical connector, and wherein the measurement housing comprises a second electrical connector configured to engage the first electrical connector to transmit electrical power between the handpiece housing assembly and the measurement housing when the handpiece coupler is coupled to the measurement coupler.

3. The surgical handpiece system of claim 1, wherein the drive cannula comprises an external surface, with the external surface defining a driven portion adjacent a proximal end of the drive cannula, the driven portion configured to receive torque from the motor, and wherein the drive cannula comprises an internal surface defining a bore that extends along the longitudinal axis, and with the internal surface comprising a first driving portion adjacent the proximal end of the drive cannula, and wherein the drive cannula comprises a distal protrusion adjacent a distal end of the drive cannula comprising a second driving portion configured to transmit torque to the surgical attachment module, the first driving portion and the second driving portion being geometrically different from one another.

4. The surgical handpiece system of claim 3, wherein the drive shaft comprises a coupler configured to be removably coupleable to the second driving portion to transmit torque between the surgical handpiece assembly and the surgical attachment module when the handpiece coupler is coupled to the surgical attachment coupler.

5. The surgical handpiece system of claim 3, further comprising a surgical end effector moveable to an engaged position wherein the surgical end effector is at least partially received in the bore of the drive cannula such that a proximal end of the surgical end effector is positioned to receive torque from the first driving portion and a distal end of the surgical end effector extends from the handpiece housing assembly.

6. The surgical handpiece system of claim 5, wherein the measurement module comprises a depth cannula being slidably coupled to the measurement housing.

7. The surgical handpiece system of claim 6, wherein the depth cannula comprises an internal surface defining a bore sized to at least partially receive the surgical end effector, and wherein the depth cannula is configured to slide relative to the surgical end effector.

8. The surgical handpiece system of claim 7, wherein the drive cannula, the depth cannula, and the surgical end effector are arranged to be concentric when the surgical end effector is in the engaged position and the measurement housing is coupled to the handpiece housing assembly.

9. The surgical handpiece system of claim 6, wherein the drive cannula is sized to at least partially receive the depth cannula within the bore of the drive cannula.

10. The surgical handpiece system of claim 5, further comprising a release assembly disposed proximally of the drive cannula, the release assembly configured to disengage the surgical end effector from the drive cannula to permit the surgical end effector to move axially from the engaged position.

11. The surgical handpiece system of claim 10, wherein the release assembly comprises a release member moveable relative to the drive cannula to a first position and a second position, the release member configured to operatively disengage the surgical end effector from the drive cannula to permit the surgical end effector to move axially from the engaged position in response to the release member moving from the first position to the second position where the release member abuts the surgical end effector.

12. The surgical handpiece system of claim 1, wherein the measurement coupler comprises a bayonet mount.

13. A surgical handpiece system comprising:
a handpiece assembly comprising,
- a handpiece housing assembly having a proximal region and a distal region, and
- a drive cannula rotatably coupled to the handpiece housing assembly and configured to receive torque from a motor and rotate in response thereto, the drive cannula extending along a longitudinal axis between a proximal end and a distal end, and the drive cannula comprising,
  - an external surface comprising a driven portion adjacent the proximal end configured to receive torque from the motor,
  - an internal surface defining a bore that extends along the longitudinal axis, the internal surface comprising a first driving portion adjacent the proximal end, and
  - a distal protrusion adjacent the distal end comprising a second driving portion;
a surgical end effector moveable to an engaged position wherein the surgical end effector is at least partially received in the bore of the drive cannula such that a proximal end of the surgical end effector is positioned to receive torque from the first driving portion and a distal end of the surgical end effector extends from the handpiece housing assembly; and
a surgical attachment module having a drive shaft, the surgical attachment module configured to be coupled to the handpiece housing assembly adjacent the distal region such that the drive shaft of the surgical attachment module is coupled to the distal protrusion and the surgical attachment module is configured to receive torque from the second driving portion, wherein the first driving portion is geometrically different from the second driving portion.

14. The surgical handpiece system of claim 13, wherein the surgical attachment module comprises one of a sagittal saw assembly, a reciprocating saw assembly, a drill chuck assembly, a reamer assembly, a wire driving assembly, and a burring assembly.

15. The surgical handpiece system of claim 13, further comprising a measurement module removably coupleable to the handpiece housing assembly adjacent the distal region of the handpiece housing assembly, the measurement module being configured to perform measurement functions associated with the surgical end effector when the surgical end effector is in the engaged position, and the measurement module comprises a measurement housing and a depth cannula being slidably coupled to the measurement housing.

16. The surgical handpiece system of claim 15, wherein the depth cannula comprises an internal surface defining a bore, with the bore of the depth cannula sized to at least partially receive the surgical end effector, and the depth cannula configured to slide relative to the surgical end effector.

17. The surgical handpiece system of claim 13, wherein the drive cannula comprises a body section extending from the proximal end toward the distal end and the distal protrusion extends distally and generally parallel to the longitudinal axis from the body section to the distal end to form a drive dog configured to transmit torque via coupling to the surgical attachment module.

18. The surgical handpiece system of claim 13, wherein the surgical attachment module comprises a surgical attachment housing, the drive shaft being rotatably coupled to the surgical attachment housing and configured to receive torque from the drive cannula via coupling with the distal protrusion, and wherein the surgical attachment module comprises an output member configured to drive an attachment module end effector, and wherein the surgical attachment module comprises at least one of a linkage and a gear train coupled to the drive shaft and the output member, and wherein the at least one of the linkage and the gear train is configured to convert torque received from the drive cannula and available at the drive shaft to mechanical power available at the output member for driving the attachment module end effector.

19. The surgical handpiece system of claim 13, further comprising a release assembly disposed proximally of the drive cannula, the release assembly configured to disengage the surgical end effector from the drive cannula to permit the surgical end effector to move axially from the engaged position.

20. The surgical handpiece system of claim 19, wherein the release assembly comprises a release member moveable relative to the drive cannula to a first position and a second position, the release member configured to operatively disengage the surgical end effector from the drive cannula to permit the surgical end effector to move axially from the engaged position in response to the release member moving from the first position to the second position where the release member abuts the surgical end effector.

* * * * *